US009285297B2

(12) United States Patent
Schroeder et al.

(10) Patent No.: US 9,285,297 B2
(45) Date of Patent: Mar. 15, 2016

(54) DEVICE, SYSTEM, AND METHOD FOR DEPOSITING PROCESSED IMMISCIBLE-FLUID-DISCRETE-VOLUMES

(75) Inventors: Benjamin G. Schroeder, San Mateo, CA (US); David M. Cox, Foster City, CA (US); Mark F. Oldham, Los Gatos, CA (US); Richard T. Reel, Hayward, CA (US); Willy Wiyatno, Union City, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 948 days.

(21) Appl. No.: 11/507,733

(22) Filed: Aug. 22, 2006

(65) Prior Publication Data

US 2007/0039866 A1     Feb. 22, 2007

Related U.S. Application Data

(60) Provisional application No. 60/710,167, filed on Aug. 22, 2005, provisional application No. 60/731,133, filed on Oct. 28, 2005, provisional application No. 60/818,197, filed on Jun. 30, 2006.

(51) Int. Cl.

| | |
|---|---|
| *C12Q 1/68* | (2006.01) |
| *C12P 19/34* | (2006.01) |
| *G01N 1/14* | (2006.01) |
| *B01L 3/00* | (2006.01) |
| *F15C 5/00* | (2006.01) |
| *F16K 99/00* | (2006.01) |
| *G01N 35/08* | (2006.01) |
| *B01L 3/02* | (2006.01) |
| *B01L 7/00* | (2006.01) |

(52) U.S. Cl.
CPC ............ *G01N 1/14* (2013.01); *B01L 3/502715* (2013.01); *B01L 3/502784* (2013.01); *C12Q 1/6869* (2013.01); *F15C 5/00* (2013.01); *F16K 99/0001* (2013.01); *F16K 99/0011* (2013.01); *F16K 99/0013* (2013.01); *G01N 35/08* (2013.01); *B01J 2219/0036* (2013.01); *B01J 2219/0061* (2013.01); *B01J 2219/00353* (2013.01); *B01J 2219/00364* (2013.01); *B01J 2219/00608* (2013.01); *B01J 2219/00612* (2013.01); *B01J 2219/00619* (2013.01); *B01J 2219/00626* (2013.01); *B01J 2219/00637* (2013.01); *B01J 2219/00653* (2013.01); *B01J 2219/00657* (2013.01); *B01J 2219/00659* (2013.01); *B01L 3/0293* (2013.01); *B01L 7/52* (2013.01); *B01L 2200/0673* (2013.01); *B01L 2200/10* (2013.01); *B01L 2300/0864* (2013.01); *B01L 2300/0867* (2013.01); *B01L 2400/0421* (2013.01); *B01L 2400/0487* (2013.01); *F16K 2099/0084* (2013.01); *Y10T 137/0318* (2015.04); *Y10T 137/4259* (2015.04); *Y10T 137/85978* (2015.04); *Y10T 137/85986* (2015.04); *Y10T 137/86863* (2015.04); *Y10T 436/2575* (2015.01)

(58) Field of Classification Search
USPC ............... 435/6.12, 91.2; 210/265; 204/182.8
See application file for complete search history.

(56) References Cited

U.S. PATENT DOCUMENTS

| | | | |
|---|---|---|---|
| 2,933,293 | A | 4/1960 | Ferrari, Jr. |
| 3,524,366 | A | 8/1970 | Hrdina |
| 3,768,496 | A | 10/1973 | Hills et al. |
| 4,028,056 | A | 6/1977 | Snyder et al. |
| 4,253,846 | A | 3/1981 | Smythe et al. |
| 4,399,102 | A | 8/1983 | Karlberg et al. |
| 4,834,877 | A | 5/1989 | Peters et al. |
| 4,908,112 | A | 3/1990 | Pace |
| 5,092,972 | A | 3/1992 | Ghowsi |
| 5,134,079 | A | 7/1992 | Cusack et al. |
| 5,270,183 | A | 12/1993 | Corbett et al. |
| 5,405,746 | A | 4/1995 | Uhlen |
| 5,645,930 | A | 7/1997 | Tsou |
| 5,720,923 | A | 2/1998 | Haff et al. |
| 5,779,977 | A | 7/1998 | Haff et al. |
| 5,800,996 | A | 9/1998 | Lee et al. |

(Continued)

FOREIGN PATENT DOCUMENTS

| | | | | |
|---|---|---|---|---|
| EP | 1 259 316 B1 | 9/2001 | | |
| EP | 1 114 316 B1 * | 2/2003 | ........... | G01N 21/447 |

(Continued)

OTHER PUBLICATIONS

Selvaganapathy et al., Recent Progress in Microfluidic Devices for Nucleic Acid and Antibody Assays, Proceedings of the IEEE, vol. 91, No. 6, Jun. 2003, pp. 954-975.*

(Continued)

*Primary Examiner* — Kenneth R. Horlick
*Assistant Examiner* — Joyce Tung

(57) ABSTRACT

Various embodiments relate to systems and/or methods for sample preparation that can be used for biochemical and/or molecular biology procedures involving small volumes, for example, micro volumes or smaller. Methods and systems that can reduce sample size requirements and increase the number of samples on a substrate are provided. Samples can be applied to a plate or other appropriate substrate and can be used for, inter alia, sequencing reactions. In some embodiments, apparatuses, systems, and/or methods for charged analyte collection are provided. Charged analytes in a sample can be electrokinetically collected or extracted from a conduit through a hole formed in a sidewall of the conduit, by application of an electric field that causes the charged analytes to migrate in a direction that is transverse to the conduit.

37 Claims, 31 Drawing Sheets

(56) References Cited

U.S. PATENT DOCUMENTS

| | | |
|---|---|---|
| 5,827,480 A | 10/1998 | Haff et al. |
| 5,843,767 A | 12/1998 | Beattie |
| 5,846,727 A | 12/1998 | Soper et al. |
| 5,942,433 A | 8/1999 | Vinson et al. |
| 5,942,443 A | 8/1999 | Parce et al. |
| 5,961,800 A | 10/1999 | McBride et al. |
| 6,033,880 A | 3/2000 | Haff et al. |
| 6,046,056 A | 4/2000 | Parce et al. |
| 6,057,100 A | 5/2000 | Heyneker |
| 6,132,996 A | 10/2000 | Hunicke-Smith |
| 6,143,496 A | 11/2000 | Brown et al. |
| 6,154,707 A | 11/2000 | Livak et al. |
| 6,255,083 B1 | 7/2001 | Williams |
| 6,348,354 B1 | 2/2002 | Adolfsen et al. |
| 6,406,893 B1 | 6/2002 | Knapp et al. |
| 6,447,661 B1 | 9/2002 | Chow et al. |
| 6,479,299 B1 | 11/2002 | Parce et al. |
| 6,485,905 B2* | 11/2002 | Hefti .................. 435/6 |
| 6,508,273 B1 | 1/2003 | Van Den Berg |
| 6,524,456 B1 | 2/2003 | Ramsey et al. |
| 6,569,305 B1 | 5/2003 | Palmer et al. |
| 6,605,451 B1 | 8/2003 | Marmaro et al. |
| 6,610,499 B1 | 8/2003 | Fulwyler et al. |
| 6,626,416 B2 | 9/2003 | Sharma et al. |
| 6,719,535 B2 | 4/2004 | Rakestraw et al. |
| 6,814,934 B1 | 11/2004 | Higuchi |
| 6,843,963 B1 | 1/2005 | Jennissen et al. |
| 6,872,571 B1 | 3/2005 | Adolfsen et al. |
| 6,875,619 B2 | 4/2005 | Blackburn |
| 6,908,770 B1 | 6/2005 | McDevitt et al. |
| 6,911,132 B2 | 6/2005 | Pamula et al. |
| 6,925,856 B1 | 8/2005 | Williams |
| 7,041,481 B2* | 5/2006 | Anderson et al. ............ 435/91.2 |
| 7,077,152 B2 | 7/2006 | Karp |
| 7,081,227 B2 | 7/2006 | Clague et al. |
| 7,955,864 B2 | 6/2011 | Cox et al. |
| 2001/0036672 A1 | 11/2001 | Anderson et al. |
| 2001/0049148 A1* | 12/2001 | Wolk et al. .................... 436/180 |
| 2003/0006140 A1 | 1/2003 | Vacca et al. |
| 2003/0096310 A1 | 5/2003 | Hansen et al. |
| 2003/0145894 A1 | 8/2003 | Burns |
| 2003/0148535 A1 | 8/2003 | Colin |
| 2003/0162213 A1* | 8/2003 | Fuller et al. .................. 435/6 |
| 2003/0194709 A1* | 10/2003 | Yang .................. 435/6 |
| 2004/0007463 A1 | 1/2004 | Ramsey et al. |
| 2004/0022686 A1 | 2/2004 | Charles et al. |
| 2004/0058450 A1 | 3/2004 | Pamula et al. |
| 2004/0180346 A1 | 9/2004 | Anderson et al. |
| 2004/0185484 A1 | 9/2004 | Costa et al. |
| 2004/0188254 A1 | 9/2004 | Spaid |
| 2004/0241693 A1* | 12/2004 | Ricoul et al. .................. 435/6 |
| 2004/0241721 A1* | 12/2004 | Gjerde et al. .................. 435/6 |
| 2004/0248144 A1* | 12/2004 | Mir .................. 435/6 |
| 2004/0259268 A1 | 12/2004 | Jacobs et al. |
| 2005/0042648 A1 | 2/2005 | Griffiths et al. |
| 2005/0048481 A1 | 3/2005 | Komori et al. |
| 2005/0048561 A1 | 3/2005 | Fulwyler et al. |
| 2005/0087122 A1 | 4/2005 | Ismagilov et al. |
| 2005/0112591 A1 | 5/2005 | Dimsoski et al. |
| 2005/0130173 A1* | 6/2005 | Leamon et al. .................. 435/6 |
| 2005/0172476 A1 | 8/2005 | Stone et al. |
| 2005/0227264 A1 | 10/2005 | Nobile et al. |
| 2005/0260640 A1 | 11/2005 | Andersen et al. |
| 2005/0272071 A1 | 12/2005 | Lao et al. |
| 2005/0282206 A1 | 12/2005 | Corbett et al. |
| 2006/0003439 A1 | 1/2006 | Ismagilov et al. |
| 2006/0037657 A1 | 2/2006 | Shibata et al. |
| 2006/0040297 A1 | 2/2006 | Leamon et al. |
| 2006/0068390 A1 | 3/2006 | Tillett et al. |
| 2006/0078888 A1 | 4/2006 | Griffiths et al. |
| 2006/0094119 A1 | 5/2006 | Ismagilov et al. |
| 2006/0110831 A1 | 5/2006 | Kijlstra et al. |
| 2007/0039866 A1 | 2/2007 | Schroeder |
| 2007/0068573 A1 | 3/2007 | Cox |
| 2007/0141593 A1 | 6/2007 | Lee |
| 2008/0023330 A1 | 1/2008 | Viovy et al. |
| 2010/0209916 A1 | 8/2010 | Zon |

FOREIGN PATENT DOCUMENTS

| | | |
|---|---|---|
| WO | WO 2004/051218 A2 | 6/2004 |
| WO | WO 2004/070007 A2 | 8/2004 |
| WO | WO 2005/003375 A2 | 1/2005 |

OTHER PUBLICATIONS

Shultz-Lockyear et al., Effects of injector geometry and sample matrix on injection and sample loading in integrated capillary electrophoresis devices, Electrophoresis 1999, 20, 529-538.*

McGall et al., Light-directed synthesis of high-density oligonucleotide arrays using semiconductor photoresists, Proc. Natl. Acad. Sci. USA vol. 93, pp. 13555-13560, Nov. 1996, Applied Physical Sciences.*

Cheng et al., Development of a Multichannel Microfluidic Analysis System Employing Affinity Capillary Electrophoresis for Immunoassay, Anal. Chem. 2001, 73, 1472-1479.*

Obeid et al., Microfabricated Systems for Nucleic Acid Analysis, Critical Reviews in Clinical Laboratory Sciences, 41(5-6):429-465 (2004).*

Marras et al., Multiplex detection of single-nucleotide variations using molecular beacons, Genetic Analysis: Biomolecular Engineering 14 (1999) 151-156.*

Schneegass et al., Flow-through polymerase chain reactions in chip thermocyclers, Reviews in Molecular Biotechnology 82Ž, 2001, pp. 101_121.*

Lichtenberg et al., Review, Sample pretreatment on microfabricated devices, Talanta 56 (2002) 233-266.*

Heller et al, Active microelentronic chip devices . . . , Electrophoresis, 2000, vol. 21, pp. 157-164.*

Johanson, Platinum, p. 2, book published 2006.*

Tice et al., Formation of Droplets and Mixing in Multiphase Microfluidics at Low Values of the Reynolds and the Capillary Numbers, Langmuir 2003, 19, 9127-9133.*

Notification of Transmittal dated Mar. 6, 2008, from PCT Application No. PCT/US2006/032602.

International Preliminary Report on Patentability date Feb. 26, 2008, from PCT Application No. PCT/US2006/032602.

Written Opinion of International Searching Authority dated Aug. 27, 2007, from PCT Application No. PCT/US2006/032602.

Notification of Transmittal dated Aug. 27, 2007, from PCT Application No. PCT/US06/32602.

International Search Report dated Aug. 27, 2007, from PCT Application No. PCT/US06/32602.

Written Opinion of International Searching Authority dated Aug. 27, 2007, from PCT Application No. PCT/US06/32602.

Lagally, E.T. et al., "Single-Molecule DNA Amplification and Analysis in an Integrated Microfluidic Device", Anal. Chem., Feb. 1, 2001, vol. 1, No. 73, pp. 565-570, Abstract.

Pang, Ho-Ming et al., "Automated One-Step DNA Sequencing Based on Nanoliter Reaction Volumes and Capillary Electrophoresis", Nucleic Acids Research, 2000, vol. 28, No. 15, pp. i-viii.

Burns, J.R. et al., "The Intensification of Rapid Reactions in Multiphase Systems Using Slug Flow Capillaries", Lab on a Chip, 2001, vol. 1, pp. 10-15.

Hashimoto, Masahiko, et al., "On-Line Integration of PCR and Cycle Sequencing in Capillaries: from Human Genomic DNA Directly to Called Bases", Nucleic Acids Research, vol. 31, No. 8, 2003, pp. 1-17.

Gallentine, Tamara A., et al., "The Technicon Auto Analyzer II", Research Paper, New Mexico State University, pp. 1-6.

Application No. 06802016.3, Extended European Search Report mailed on Nov. 3, 2010.

Auroux, Pierre-Alain et al., "Miniaturised nucleic acid analysis", *Lab on a Chip, Royal Society of Chemistry*, Cambridge, vol. 4, 2004, 534-546.

Chiou, J. et al., "A Closed-Cycle Capillary Polymerase Chain Reaction Machine", *Analytical Chemistry, American Chemical Society*, vol. 73, No. 9, 2001, 2018-2021.

(56) References Cited

OTHER PUBLICATIONS

Curcio, Mario et al., "Continuous segmented-Flow Polymerase Chain Reaction for High-Throughput Miniaturized DNA Amplification", *Anal. Chem*, vol. 75(1), American Chemical Society, 2003, 1-7.

Obied, P.J. et al., "Microfabricated systems for nucleic acid analysis", *Critical Reviews in Clinical Laboratory Sciences*, CRC Press, Boca Raton, FL, vol. 41, No. 5-6, Jan. 1, 2004, 429-465.

Schneegass, et al., "Miniaturized flow-through PCR with different template types in a silicon chip thermocycler", *Lab on a Chip*; vol. 1, 2001, 42-49.

Waters, L.C. et al., "Microchip Device for Cell Lysis, Multiplex PCR Amplification, and Electrophoretic Sizing", *Analytical Chemistry*, vol. 70, No. 1, American Chemical Society, Columbus, US, 1998, 158-162.

* cited by examiner

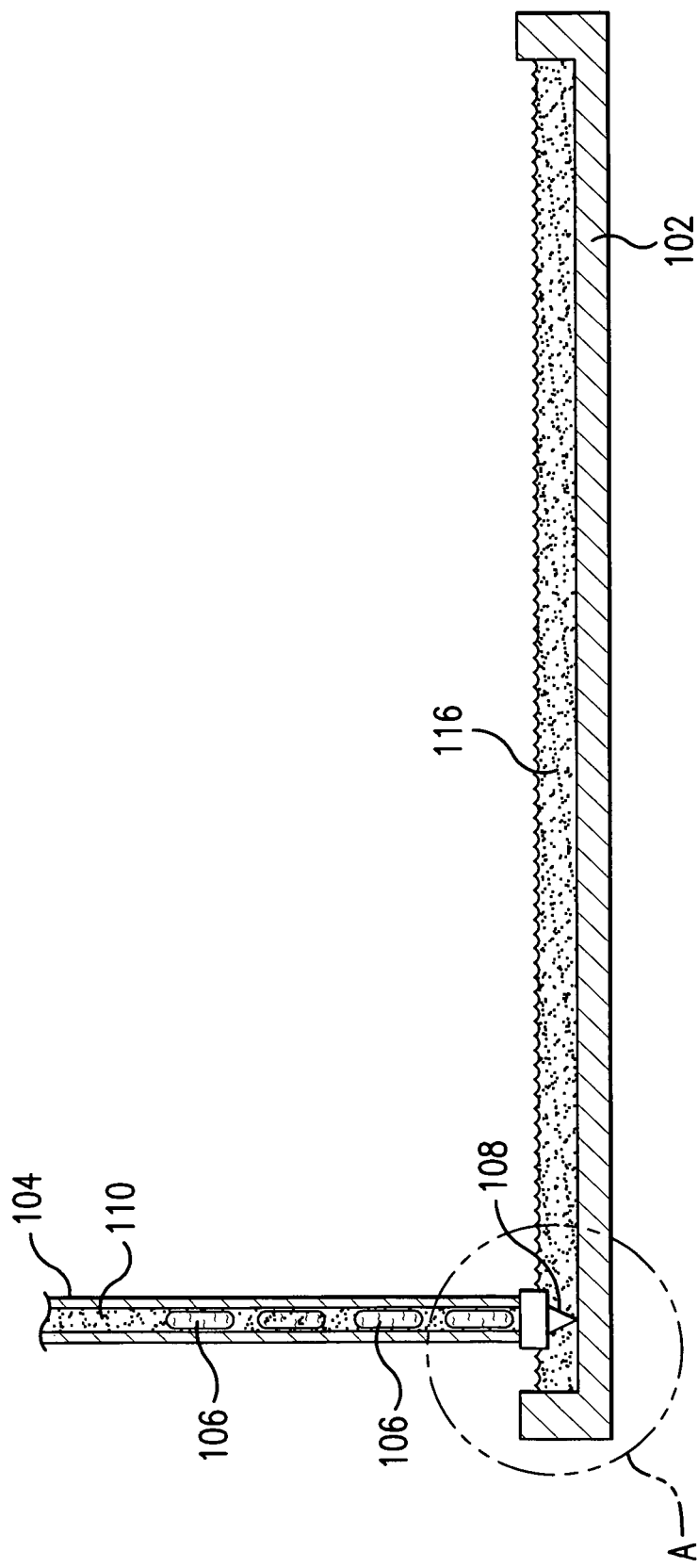

DEVICE, SYSTEM, AND METHOD FOR DEPOSITING PROCESSED IMMISCIBLE-FLUID-DISCRETE-VOLUMES

CROSS-REFERENCE TO RELATED APPLICATIONS

The present application claims the benefit of earlier filed U.S. Provisional Patent Application No. 60/710,167, filed Aug. 22, 2005, U.S. Provisional Patent Application No. 60/731,133, filed Oct. 28, 2005, and U.S. Provisional Patent Application No. 60/818,197, filed Jun. 30, 2006, which are incorporated herein in their entireties by reference.

INTRODUCTION

The section headings used herein are solely for organization purposes and are not to be construed as limiting the subject matter described in any way.

Large scale sequencing projects can involve cloning DNA fragments in bacteria, picking and amplifying those fragments, and performing individual sequencing reactions on each clone. Standard sequencing reactions can often be performed in 5 µl to 20 µl reaction volumes, even though only a small fraction of the sequencing product can be analyzed. Such cloning and sequencing protocols can be time consuming and can use relatively large sample and reagent volumes. The relatively large volumes can be wasteful in terms of expensive consumable reagents, and input sample quantity.

SUMMARY

Various embodiments of the present teachings relate to systems, apparatus, and/or methods for sample preparation that can be used for biochemical or molecular biology procedures involving different volumes, for example, small volumes such as micro-liter sized volumes or smaller.

According to the present teachings, the system can comprise an apparatus for generating discrete volumes of at least a first fluid in contact with a second fluid, wherein the first and second fluids are immiscible with each other, for example, discrete volumes of an aqueous liquid (herein "aqueous immiscible-fluid-discrete-volumes"), spaced-apart from one another by a spacing fluid that is immiscible with the immiscible-fluid-discrete-volumes. An immiscible-fluid-discrete-volume can be a partitioned segment in which molecular biology procedures can be performed. As used herein, an immiscible-fluid-discrete-volume can be one of many structures, three of which are: a fluid segment, a slug, and an emulsified droplet. In some embodiments, immiscible-fluid-discrete-conduits are formed and/or processed in a conduit.

This paragraph defines a conduit as it is used herein. A conduit can be any device in which an immiscible-fluid-discrete-volume can be generated, conveyed, and/or flowed. For example, a conduit as defined herein can comprise any of a duct, a tube, a pipe, a channel, an open top channel, a closed channel, a capillary, a hole or another passageway in a solid structure, or a combination of two or more of these, as long as the spaces defined by the respective solid structures are in fluid communication with one another. A conduit can comprise two or more tubes or other passageways connected together, or an entire system of different passageways connected together. An exemplary conduit can comprise an immiscible-fluid-discrete-volume-forming tube, thermal spirals, valve passageways, a processing conduit, junctions, and the like components all connected together to form one or more fluid communications therethrough, which system is also referred to herein as a main processing conduit. Examples of solid structures with holes or passageways therein that can function as conduits are manifolds, T-junctions, Y-junctions, rotary valves, and other valves. Thus, when connected to conduits, such structures can be considered part of a conduit as defined herein.

This paragraph defines a fluid segment, as it is used herein. A fluid segment is a discrete volume that has significant contact with one or more conduit wall(s), such that a cross-sectional area of the fluid segment is the same size and shape as the cross-sectional area of the conduit it contacts. At least a portion of a fluid segment fully fills the cross-sectional area of the conduit, such that the immiscible fluid adjacent it in the conduit can not flow past the fluid segment. The entire longitudinal length of the fluid segment may not contact the conduit walls.

This paragraph defines a slug as used herein. A slug is a discrete volume that has at least a portion of which has approximately the same cross-sectional shape as the conduit in which it exists, but a smaller size. The smaller size is due to the insignificant contact, if any, of the slug with the conduit wall(s). A slug can have a cross-sectional dimension between approximately 0.5 and approximately 1.0 times the maximum dimension of a cross sectional area of the conduit. If the conduit has a circular cross section, the cross-sectional area of a slug can be concentric with the conduit's cross-sectional area, but it does not have to be, such as, for example, when the conduit is horizontal and, due to different specific gravities, one fluid rises toward the top of the cross-sectional area of the conduit under the influence of gravity. A slug can be free of contact with the conduit walls. When not moving relative to the conduit, a slug can have "feet" that appear as nibs or bumps along an otherwise smoothly appearing round surface. It is theorized that the feet at the bottom of the slug may have contact with the conduit wall. In contrast to a fluid segment, the contact a slug can have with the conduit wall(s) still permits the immiscible fluid adjacent it in the conduit to flow past the slug.

The "slugs" formed by the teachings herein, separated by spacing fluid, can merge together to form larger slugs of liquid, if contacted together. The ability of the slugs, for example, aqueous slugs, described and taught herein, to merge together with each other, facilitates the downstream addition of aqueous reagents to the slugs.

This paragraph defines an emulsified droplet, as used herein. An emulsified droplet is a discrete volume that has no contact with the walls of the conduit. The size of an emulsified droplet is not necessarily constrained by the conduit, and examples of emulsified droplets described in the prior art range in size from about 1 femtoliter to about 1 nanoliter. The shape of an emulsified droplet is not constrained by the conduit, and due to the difference in surface-energies between it and the continuous phase liquid in which it is dispersed, it is generally spherical. It can have a maximum dimension that is not equal to, nor approximately equal to, but much less than the maximum dimension of the cross-sectional area of the conduit, for example, 20%, 10%, 5% or less. As described in the prior art, emulsified droplets typically range in volume from about 1 femtoliter to about 1 nanoliter. An emulsified droplet will not merge upon contact with another emulsified droplet to form a single, larger discrete volume, without external control. Put another way, an emulsified droplet is a stable discontinuous phase in a continuous phase.

A conduit can contain more than one emulsified droplet, but not more than one slug or fluid segment, at any cross-sectional location. Thus, a first emulsified droplet may not necessarily impede the movement of a second emulsified droplet past it, where as a fluid segment and a slug necessarily do not permit the passage of another fluid segment or slug past them, respectively. If two fluid segments are separated by a fluid with which the first and second of the two fluids is each immiscible, then the immiscible fluid also forms a discrete volume. It is likely that it has significant contact with the conduit walls and thus is another fluid segment.

Whether two immiscible fluids, when present in a conduit, form fluid segments of the first and second of the two immiscible fluids, slugs of the first immiscible fluid, or emulsified droplets of the first immiscible fluid depends on at least the method of introduction of each fluid into the conduit, the relative surface energies of the first immiscible fluid, the second immiscible fluid, and the conduit material, and the contact angle each forms with the other two materials, respectively, and the volume of the first immiscible fluid. Thus, it is recognized that these definitions are merely reference points on a continuum, the continuum of the shape and size of discrete volumes of a first immiscible fluid in a conduit, and discrete volumes will exist that, when described, fall between these definitions.

The molecular biology procedures can, for example, utilize proteins or nucleic acids. Procedures with nucleic acids can comprise, for example, a PCR amplification and/or nucleic acid analysis of an amplification product. The PCR amplification and/or nucleic acid analysis of an amplification product can comprise an integrated DNA amplification/DNA sequencing method.

Using the apparatus, methods, and/or systems provided in this application, a polymerase chain reaction (PCR) amplification of single DNA molecules can be performed, for example, to obtain amplicons. The amplified DNA or amplicons can then be used in a sequencing reaction and then be sequenced in small volumes. Other manipulations of nucleic acids or proteins can also be accomplished, for example, DNA hybridization reactions or antibody-antigen binding assays.

The apparatus, system and/or methods described herein can also be used in conjunction with U.S. Provisional Patent Application No. 60/710,167 entitled "Sample Preparation for Sequencing" to Lee et al., filed Aug. 22, 2005, U.S. Provisional Patent Application No. 60/731,133 entitled "Method and System for Spot Loading a Sample" to Schroeder et al., filed Oct. 28, 2005, and systems described in U.S. Provisional Patent Application No. 60/818,197 filed Jun. 30, 2006, each of which are incorporated herein in their entireties by reference.

An exemplary type of sample preparation can be used for genotyping, gene-expression, methylation analysis, and/or directed medical sequencing (VariantSEQr™, for example) that requires multiple liquids to be brought together in an aqueous discrete volume. For example, in a gene-expression application, each aqueous discrete volume can contain individual primer sets. The sample to be analyzed, for example, complementary DNA (cDNA), can be added to each aqueous discrete volume. In the VariantSEQr™ application, for example, an aqueous discrete volume can comprise a primer set and genomic DNA can be added to that discrete volume. According to various embodiments, a system and method are provided that are able to process discrete volumes with unique content. According to various embodiments of the present teachings, spitting, dropping, or other techniques to discharge immiscible-liquid, discrete volumes can be used. According to various embodiments, an immiscible-liquid, discrete volume of at least an aqueous sample fluid can be discharged from a tube.

According to various embodiments, a system is provided comprising: at least one conduit; a substrate separate from and spaced from the at least one conduit, the substrate comprising an electrically conductive surface; and an apparatus for moving in a predetermined pattern relative to one another, the substrate and the at least one conduit.

According to various embodiments, a system is provided comprising: an aqueous sample injection unit in fluid communication with at least one conduit comprising a maximum inner cross-sectional dimension; a spacing fluid injection unit in fluid communication with the at least one conduit, the aqueous sample injection unit and the spacing fluid injection unit comprising separate units each in fluid communication with the at least one conduit; a control unit adapted to flow an aqueous sample and a spacing fluid from the aqueous sample injection unit and the spacing fluid injection unit, respectively, and adapted to inject volumes of aqueous sample and spacing fluid that respectively form slugs in the at least one conduit wherein each slug has an outer dimension that is equal to the maximum inner cross-sectional dimension of the at least one conduit; an electrically conductive substrate; and a capillary electrophoretic sequencer adapted to inject a sample component when a sample component is disposed on the electrically conductive surface.

According to various embodiments, a method is provided comprising: forming a plurality of aqueous sample slugs spaced apart from one another by slugs of spacing fluid in a conduit, at least one of the aqueous sample slugs comprising at least one target analyte; and dispensing the aqueous sample slugs one-at-a-time from the conduit onto a substrate to form a pattern of spaced apart aqueous samples on the substrate, the substrate comprising an electrically conductive surface.

According to various embodiments, a method is provided comprising: forming in a conduit a plurality of aqueous sample slugs, at least one of the aqueous sample slugs comprising at least one target analyte comprising at least one respective linkage group; and dispensing the aqueous sample slugs one-at-a-time from the conduit onto a substrate to form a pattern of aqueous samples on the substrate, the substrate comprising an electrically conductive surface adapted to bind the at least one respective linkage group to form an attached analyte.

According to various embodiments, a method is provided comprising: amplifying DNA in a plurality of aqueous sample slugs in a conduit to form amplicons, each aqueous slug separated from an adjacent aqueous slug by at least one oil slug; moving or rastering the conduit comprising the amplicons over a substrate and depositing the amplicons from the conduit onto the substrate, the substrate comprising an electrically conductive surface; attaching the amplicons to the electrically conductive surface; contacting the substrate with a sequencing reaction mixture to form at least one dye-labeled spot; positioning a capillary of a capillary electrophoretic analyzer over the at least one dye-labeled spot; electrically contacting the dye-labeled spot with the capillary; and injecting one or more components from the dye-labeled spot into the capillary.

According to various embodiments, a method is provided comprising: dispensing DNA into a plurality of aqueous sample slugs in a conduit, each aqueous slug separated from an adjacent aqueous slug by at least one non-aqueous slug; moving or rastering the conduit comprising the DNA over a substrate and depositing the DNA from the conduit onto the substrate, the substrate comprising an electrically conductive surface; attaching the DNA to the electrically conductive surface; contacting the electrically conductive surface with a reaction mixture; positioning a capillary tube over the attached DNA; electrically contacting the DNA with the capillary tube; and injecting the DNA into the capillary tube.

According to various embodiments, the present teachings provide a system comprising at least one transport conduit, the at least one transport conduit comprising at least one sidewall. In some embodiments, the system can comprise a through hole formed through the at least one sidewall. In some embodiments, the system can comprise a charged analyte collection chamber in fluid communication with the through hole. In some embodiments, the system can comprise a positive electrode. In some embodiments, the system can comprise negative electrode. In some embodiments, the system can comprise a power source, wherein the positive electrode, the negative electrode, and the power source are connected together and configured to form an electric field extending from the transport conduit, through the through hole, and to the charged analyte collection chamber, and of sufficient strength to cause a charged analyte in the transport conduit to electrokinetically migrate through the through hole toward the charged analyte collection chamber.

According to various embodiments, the present teachings provide a method comprising moving a sample comprising a charged analyte through a transport conduit and into alignment with a portion of the transport conduit comprising a through hole formed in a sidewall thereof. In some embodiments, the method can comprise generating an electric field that extends through the through hole. In some embodiments, the method can comprise electrokinetically migrating the charged analyte from the transport conduit and through the through hole.

According to various embodiments, the present teachings provide a system comprising an immersion plate, and a layer of a first fluid retained by the immersion plate. In some embodiments, the system can comprise a conduit comprising a tip and an interior, the interior comprising a plurality of immiscible-fluid-discrete-volumes of a second fluid, spaced apart by a spacing fluid that is immiscible with each of the immiscible-fluid-discrete-volumes, disposed in the interior, wherein the tip is positioned such that when the immiscible-fluid-discrete-volumes exit the tip, the immiscible-fluid-discrete-volumes contact the first fluid retained by the immersion plate, and the second fluid has a different density than the first fluid.

According to various embodiments, the present teachings provide a method comprising discharging immiscible-fluid-discrete-volumes from inside a conduit having a discharge tip, through the discharge tip, and into a first fluid retained by an immersion plate, wherein the first fluid is immiscible with the immiscible-fluid-discrete-volumes and the density of the first fluid is different than the densities of each of the immiscible-fluid-discrete-volumes.

According to various embodiments, the present teachings provide a system comprising a dispensing conduit comprising a discharge tip. In some embodiments, the system can comprise a set of immiscible-fluid-discrete-volumes spaced-apart from one another by a spacing fluid that is immiscible with the immiscible-fluid-discrete-volumes, disposed in the conduit. In some embodiments, the system can comprise a negative pressure source disposed adjacent the discharge tip.

According to various embodiments, the present teachings provide a method of dispensing immiscible-fluid-discrete-volumes, comprising providing a dispensing conduit comprising a dispensing tip, and a set of immiscible-fluid-discrete-volumes spaced-apart from one another by a spacing fluid that is immiscible with the immiscible-fluid-discrete-volumes. In some embodiments, the method can comprise providing a waste removal conduit adjacent the dispensing tip. In some embodiments, the method can comprise applying a vacuum to the waste removal conduit. In some embodiments, the method can comprise detecting a first immiscible-fluid-discrete-volume, that contains an analyte of interest, from the set of immiscible-fluid-discrete-volumes. In some embodiments, the method can comprise removing the vacuum. In some embodiments, the method can comprise dispensing the first immiscible-fluid-discrete-volume.

According to various embodiments, the present teachings provide a system comprising a conduit comprising a tip. In some embodiments, the system can comprise a plurality of immiscible-fluid-discrete-volumes disposed in the conduit and spaced apart from one another by a spacing fluid that is immiscible with each of the plurality of immiscible-fluid-discrete-volumes. In some embodiments, the system can comprise a capillary electrophoresis capillary, positioned adjacent to the tip of the conduit, the capillary electrophoresis capillary having an injection tip, wherein the capillary electrophoresis capillary and the conduit are axially aligned with one another.

According to various embodiments, the present teachings provide a method comprising discharging immiscible-fluid-discrete-volumes from a tip of a conduit directly into a capillary electrophoresis capillary, the conduit comprising a plurality of immiscible-fluid-discrete volumes spaced apart from one another by a spacing fluid that is immiscible with each of the immiscible-fluid-discrete-volumes.

According to various embodiments, the present teachings provide a method comprising discharging immiscible-fluid-discrete-volumes from conduit and into an injector of a capillary electrophoresis apparatus, wherein at an interface between the conduit and the injector one or more components in the immiscible-fluid-discrete-volumes is concentrated by dielectrophoresis before entering the injector.

The molecular biology procedures that can be performed on the various discrete volumes described herein, prior to out-processing as described herein, can, for example, utilize proteins or nucleic acids. Procedures with nucleic acids can comprise, for example, a PCR amplification and/or nucleic acid analysis of an amplification product. The PCR amplification and/or nucleic acid analysis of an amplification product can comprise an integrated DNA amplification/DNA sequencing method.

Using the apparatus, methods, and/or systems provided in this application, a polymerase chain reaction (PCR) amplification of single DNA molecules can be performed, for example, to obtain amplicons. The amplified DNA or amplicons can then be used in a sequencing reaction and then be sequenced in small volumes. Other manipulations of nucleic acids or proteins can also be accomplished, for example, DNA hybridization reactions or antibody-antigen binding assays.

The apparatus, system and/or methods described herein can also be used in conjunction with U.S. Provisional Patent Application No. 60/710,167 entitled "Sample Preparation for Sequencing" to Lee et al., filed Aug. 22, 2005, U.S. Provisional Patent Application No. 60/731,133 entitled "Method and System for Spot Loading a Sample" to Schroeder et al., filed Oct. 28, 2005, and systems described in U.S. Provisional Patent Application No. 60/818,197 filed Jun. 30, 2006, which are incorporated herein in their entireties by reference.

An exemplary type of sample preparation can be used for genotyping, gene-expression, methylation analysis, and/or directed medical sequencing (VARIANTSEQR™, for example) that requires multiple liquids to be brought together in an aqueous discrete volume. For example, in a gene-expression application, each aqueous discrete volume can contain individual primer sets. The sample to be analyzed, for example, complementary DNA (cDNA), can be added to each aqueous discrete volume. In the VARIANTSEQR™ application, for example, an aqueous discrete volume can comprise a primer set and genomic DNA can be added to that discrete volume.

In some embodiments, a first conduit can have an inner diameter, and the inner diameter can be from about 10 microns to about 2000 microns. A second conduit can have an inner diameter, and the inner diameter can be from about 20 microns to about 5000 microns, and can be large enough to accommodate the outer periphery of the first conduit.

Various embodiments of the present teachings relate to an apparatus, system, or method for sample preparation and/or sample deposition. The sample preparation can be used for biochemical or molecular biology procedures involving small volumes, for example, microliter-sized volumes or smaller. The system can comprise an apparatus comprising at least two coaxially arranged tubes in fluid communication with pump(s) for providing immiscible-fluid-discrete-volumes of a first liquid separated by a second fluid, for example, immiscible-fluid-discrete-volumes of water or an aqueous-based liquid, separated by oil. The immiscible-fluid-discrete-volumes can form small partitioned segments to be used in molecular biology procedures. The molecular biology procedures can comprise, for example, a PCR amplification and/or nucleic acid analysis of the amplification product. The PCR amplification and/or nucleic acid analysis of the amplification product can comprise an integrated DNA amplification/DNA sequencing method.

Using the apparatus, methods, and/or systems provided in this application processes can be performed on the immiscible-fluid-discrete-volumes. These downstream processes can include, for example, electrophoretic separation, fluorescent detection, and the like. Other manipulations of nucleic acids or proteins can also be accomplished, for example, DNA hybridization reactions or antibody-antigen binding assays.

An apparatus is provided that can be used for different types of sample preparation and sample processing. For example, the apparatus can be used 1) to prepare spaced-apart aqueous immiscible-fluid-discrete-volumes separated by an immiscible spacing fluid, for example, oil, for carrying out reactions in microliter-sized or smaller volumes, 2) for manipulating samples of interest in immiscible-fluid-discrete-volumes and then depositing them into sample wells, or 3) for rinsing a conduit tip between depositing a first volume and depositing a second volume, to avoid contamination of the second volume with the first volume.

According to various embodiments, flow rates for preparing aqueous immiscible-fluid-discrete-volumes can comprise rates of from about 1 picoliter/sec. to about 200 microliters/sec., and can be selected based on the inner diameter of the conduits through which the liquids are to be pumped. Tubing that can be used with this flow rate can comprise an inner diameter of from about 250 microns to about 1000 microns. In other embodiments, the inner diameter of the inner tube can be from about 10 microns to about 2000 microns, while the inner diameter of the outer tube can be from about 20 microns to about 5000 microns, for example, from about 35 microns to about 500 microns. Other diameters, however, can be used based on the characteristics of the immiscible-fluid-discrete-volume formation or rinsing system desired. In some embodiments, a tube having a 10 micron inner diameter is used with a flow rate of from about 8 to about 10 picoliters/second. In some embodiments, a tube having a 5000 micron inner diameter is used with a flow rate of from about 25 to about 200 microliters/second. In some embodiments, a tube having a 500 micron inner diameter is used with a flow rate of from about 0.25 to about 2.0 microliters/second.

In other embodiments, for example, when an apparatus of the present teachings is used in a triage function for rinsing the tip of, for example, the inner tube of an apparatus, the flow rate can comprise a rate from about 0.1 microliter/sec. to about 1.0 microliter/sec.

According to various embodiments, a method is provided that uses an apparatus comprising coaxially arranged tubes. The method comprises contacting an aqueous sample liquid with a non-aqueous spacing fluid that is immiscible with the aqueous sample to form a plurality of isolated portions of the aqueous sample in a capillary channel separated from one another by the non-aqueous spacing fluid. The aqueous sample liquid can comprise a plurality of target nucleic acid sequences, wherein at least one of the isolated portions comprises at least one target nucleic acid sequence. In some embodiments, at least 50% of the plurality of the isolated portions in the inner conduit can each comprise a single target nucleic acid sequence. In various other embodiments, less than about 50% of the plurality of isolated portions in the capillary channel can each comprise a single target nucleic acid sequence. In other embodiments, at least 1% or more, 5% or more, 10% or more, or 20% or more can have a single target nucleic acid sequence, for example, upon formation of the isolated portions.

According to various embodiments, each of the plurality of isolated immiscible-fluid-discrete-volumes in the inner conduit can comprise one or more respective oligonucleotide primers. Oligonucleotide primers can be chosen as determined by one of skill in the art to accomplish the desired objective, for example, universal primers can be used.

In some embodiments, out-putting immiscible-fluid-discrete-volumes that have been subjected to upstream processing, can be integrated with the system. Such upstream processing can include amplifying the at least one target nucleic acid sequence in the first isolated portion in the capillary channel to form an amplicon, and thereafter subjecting the amplicon to a nucleic acid sequencing reaction. For such purposes, and in some embodiments, the isolated portions or immiscible-fluid-discrete-volumes can comprise reaction components, for example, oligonucleotide primers. Various embodiments of processing can include universal PCR that can comprise up-front multiplexed PCR followed by decoding, for example, see WO 2004/051218 to Andersen et al., U.S. Pat. No. 6,605,451 to Marmaro et al., U.S. patent application Ser. No. 11/090,830 to Andersen et al., and U.S. patent application Ser. No. 11/090,468 to Lao et al., all of which are incorporated herein in their entireties by reference. Details of real time PCR can be found in Higuchi et al., U.S. Pat. No. 6,814,934 B1, which is incorporated herein by reference in its entirety.

According to various embodiments, once the steps of a desired protocol, for example, a PCR, PCR clean-up, and sequencing reaction protocol, have been completed, a sample can be removed or injected from a processing conduit, for example, using an electrical field applied across a channel and extending into a charged analyte collection chamber or compartment, or by using another electrokinetic sample movement technique. The collected or extracted charged analytes removed from the sample can then be used for DNA sequencing or other procedures. The DNA sequencing can use capillary electrophoresis instruments, for example, a commercially available AB 3730xl DNA Analyzer (Applera Corporation, Foster City, Calif.), that can process samples in 96- or 384-well plate formats. In various embodiments, the sample can be removed, injected, or recovered from the processing conduit into one or more wells of a microtiter plate, for example, through a pathway that comprises a loading channel or tube.

Further devices, systems, and methods that can be used with or otherwise implement the present teachings include those described, for example, in U.S. Patent Application Publication No. 2007/0141593 A1, U.S. Patent Application Publication No. 2007/0062583 A1, and U.S. Patent Application Publication No. 2007/0068573 A1, which are herein incorporated in their entireties by reference.

DRAWINGS

The skilled artisan will understand that the drawings described below, are for illustration purposes only. The drawings are not intended to limit the scope of the present teachings in any way. In the drawings:

FIG. 2 is a cross-sectional side view of an immiscible-fluid-discrete-volume collection system comprising an immersion plate, according to various embodiments;

Figure 10A:
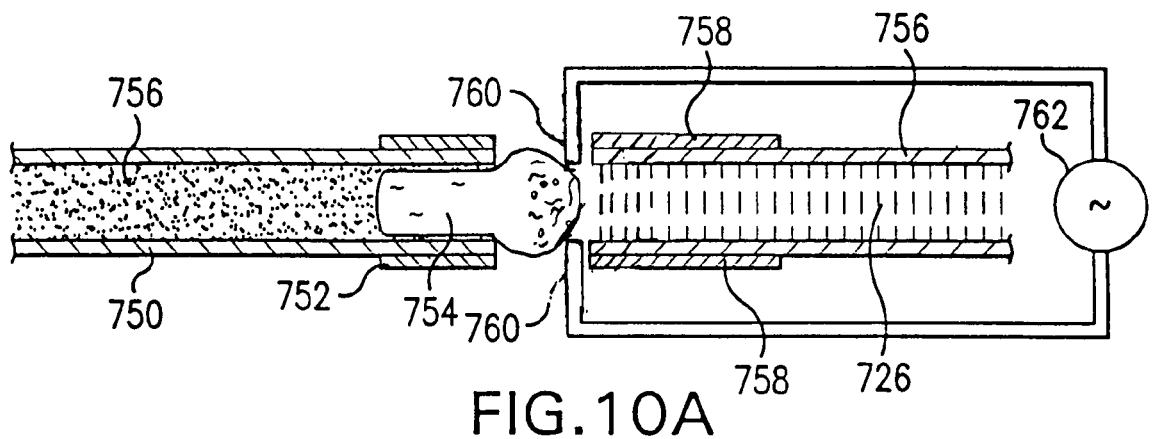
Figure 10B:
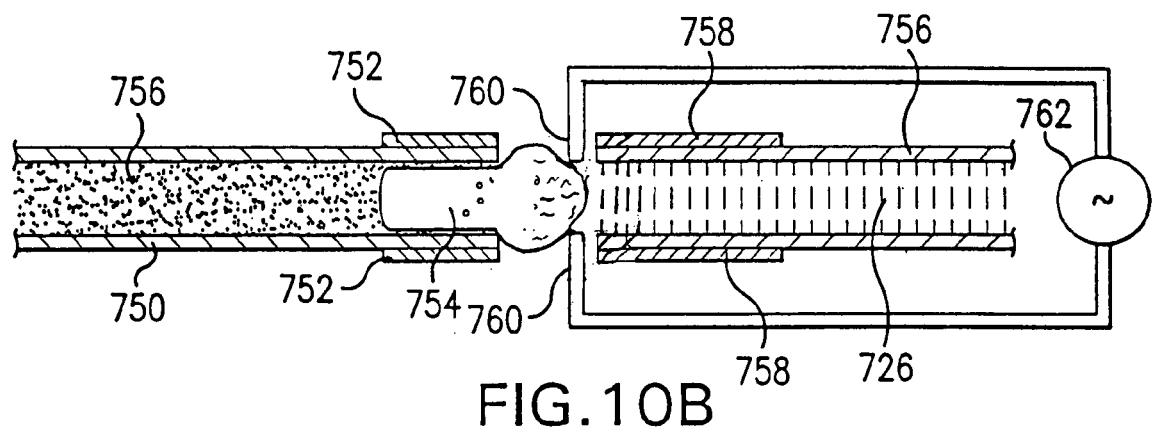
Figure 10C:
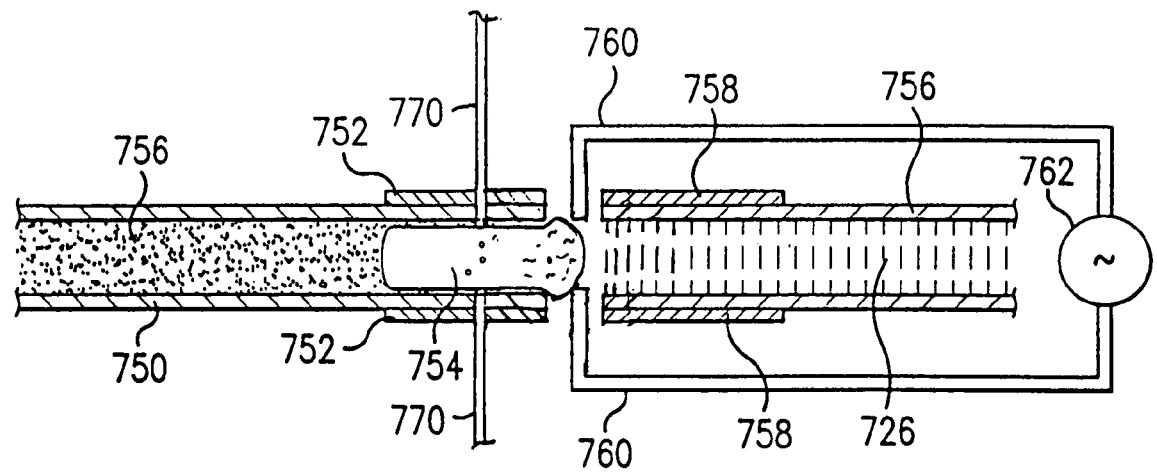
Figure 11:
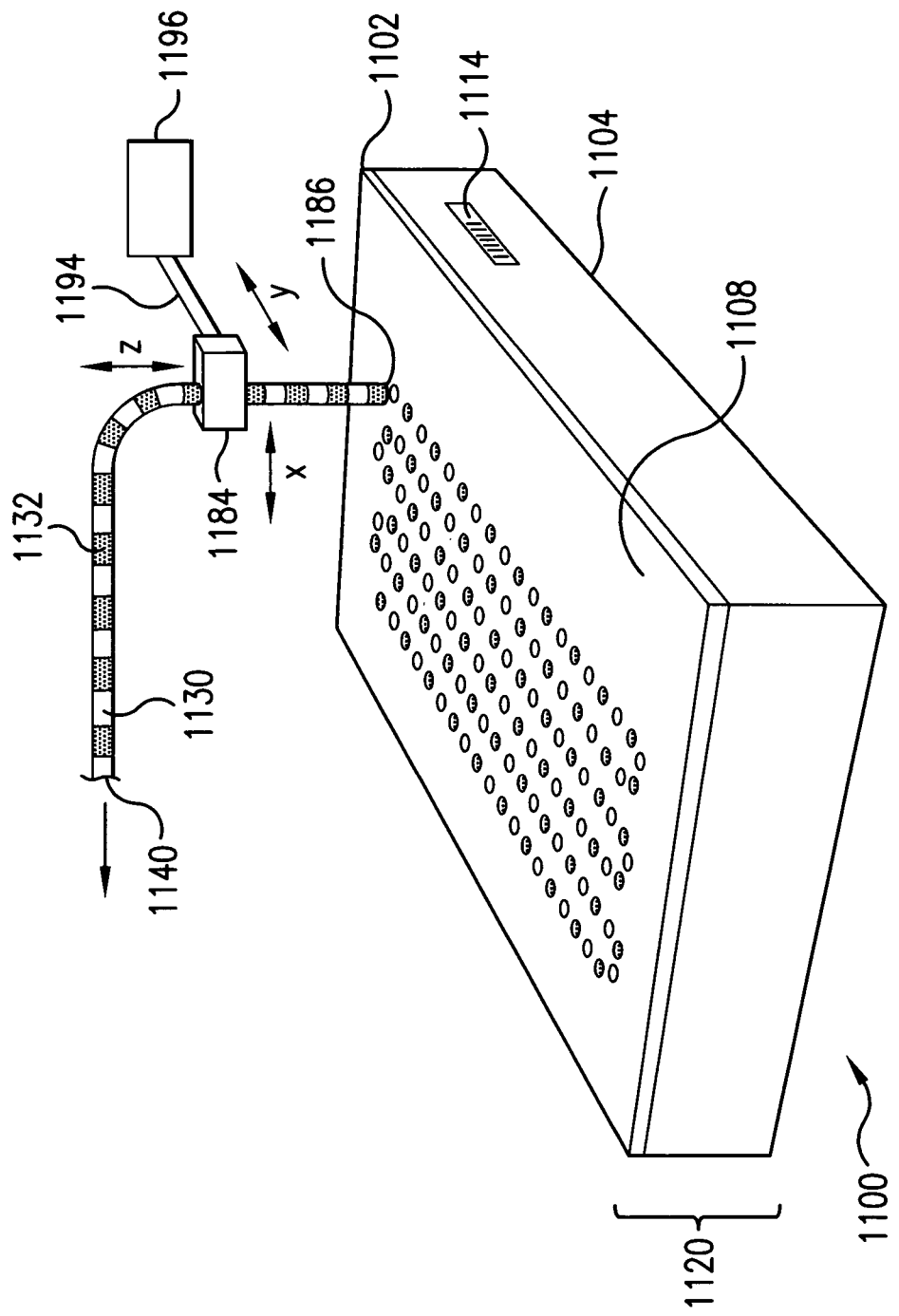
Figure 12:
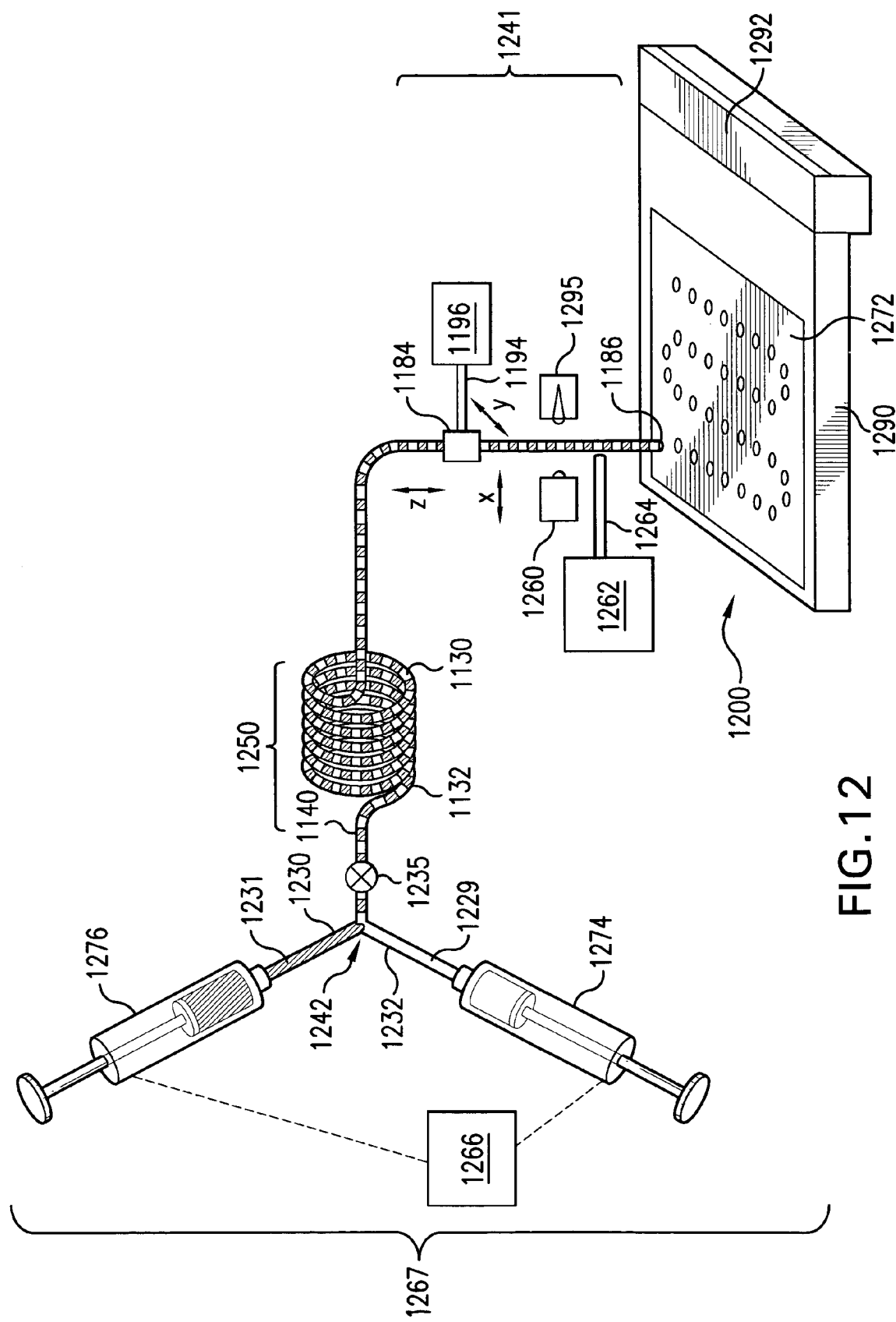

FIGS. 10A, 10B, and 10C are cross-sectional side views of various systems each comprising the discharge tip of an immiscible-fluid-discrete-volume-containing conduit axially aligned with and adjacent a dielectrophoresis device and arranged for processing of a discrete volume with the dielectrophoresis device, according to various embodiments;

FIG. 11 is a perspective view of a system for applying samples in a raster pattern to an electrically conductive substrate;

FIG. 12 is a perspective view of a system comprising an electrically conductive surface receiving samples that have been amplified by PCR reaction.

Figure 13:
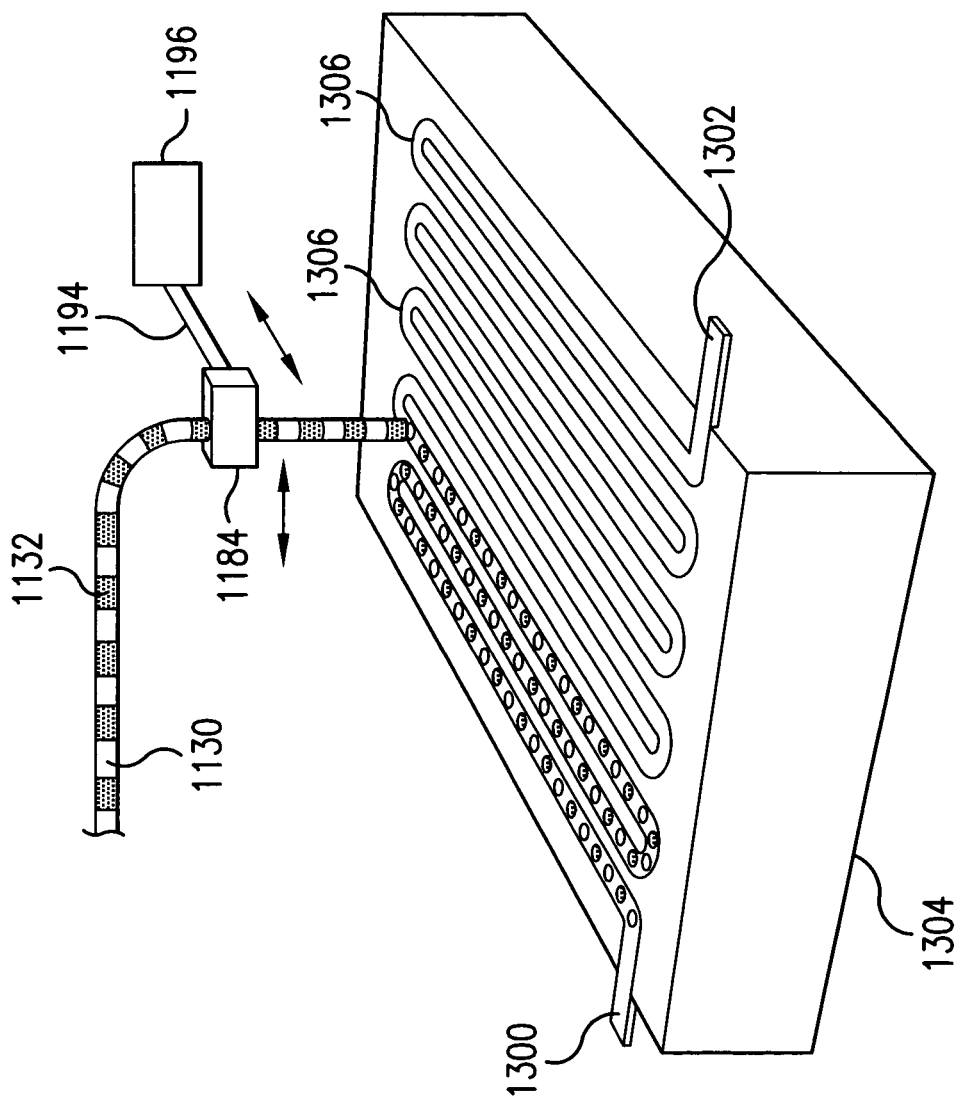

FIG. 13 is a perspective view of a system comprising a substrate having a zig-zag channel for receiving samples.

Figure 14:
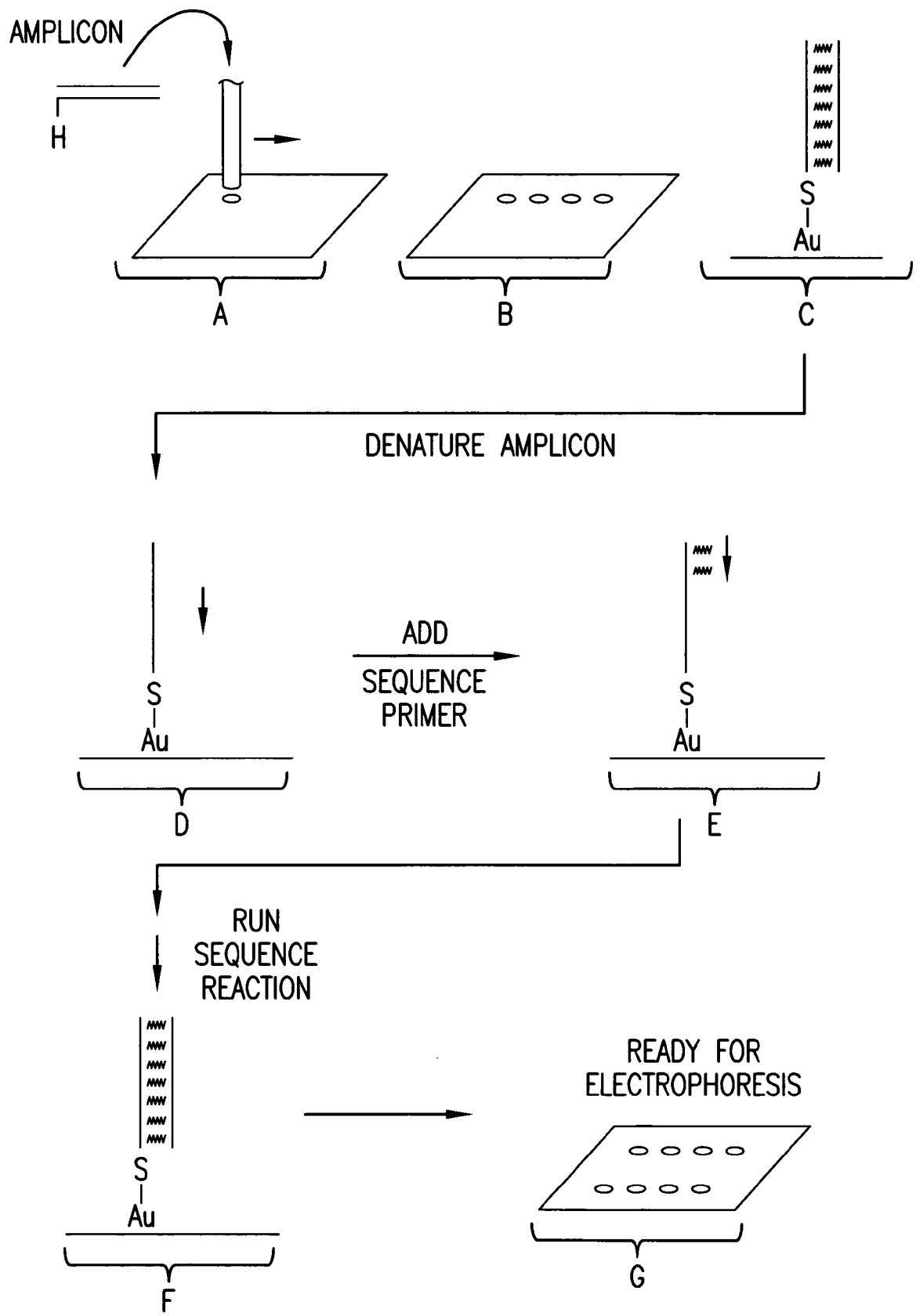

FIG. 14 illustrates a simplified protocol for sequencing products being applied to an electrically conductive surface and then being electroinjected into capillaries.

Figure 15:
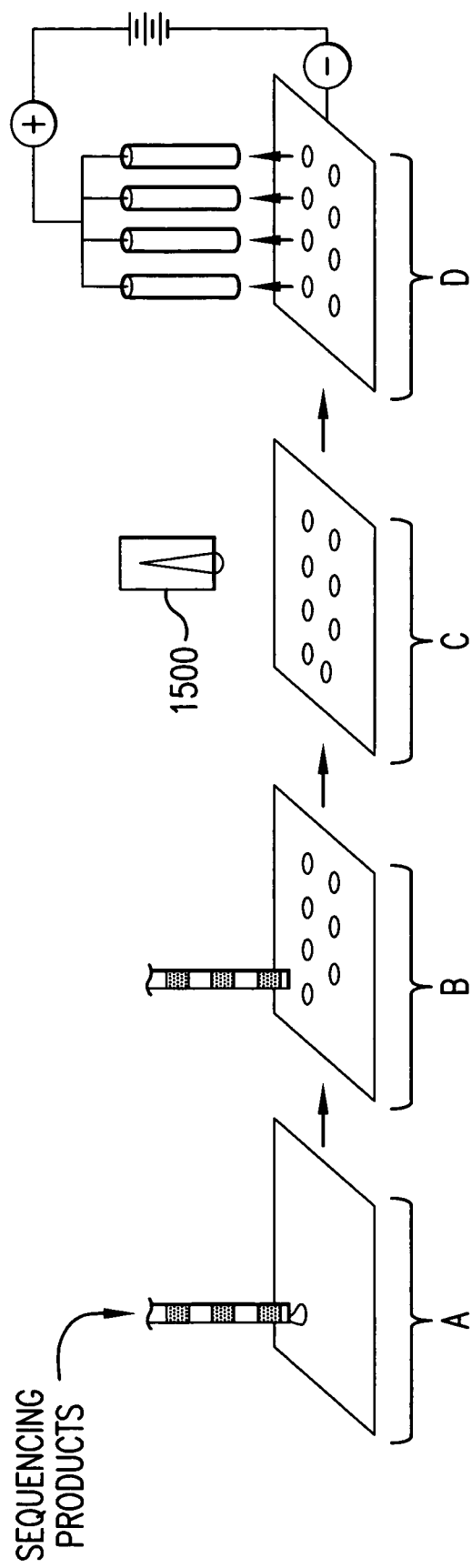
Figure 16:
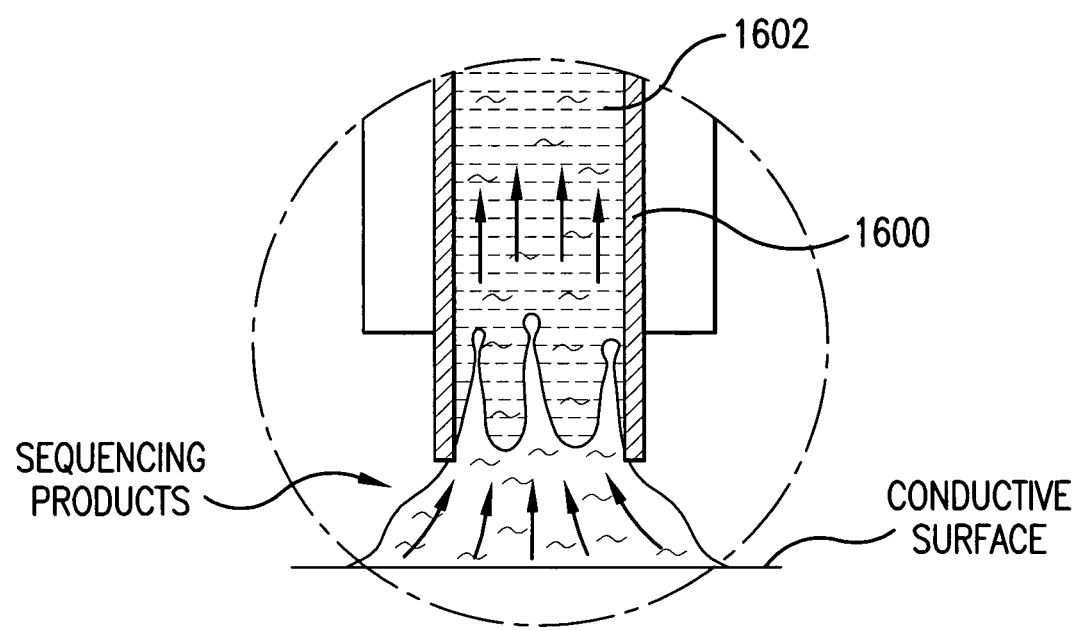

FIG. 15 illustrates a method of DNA analysis with subsequent deposition onto a substrate in preparation for injection and further analysis;

FIG. 16 provides an enlargement of part of FIG. 15 showing sample migration, for example, electrokinetically injected sample, moving into capillary tubes.

Figure 17:
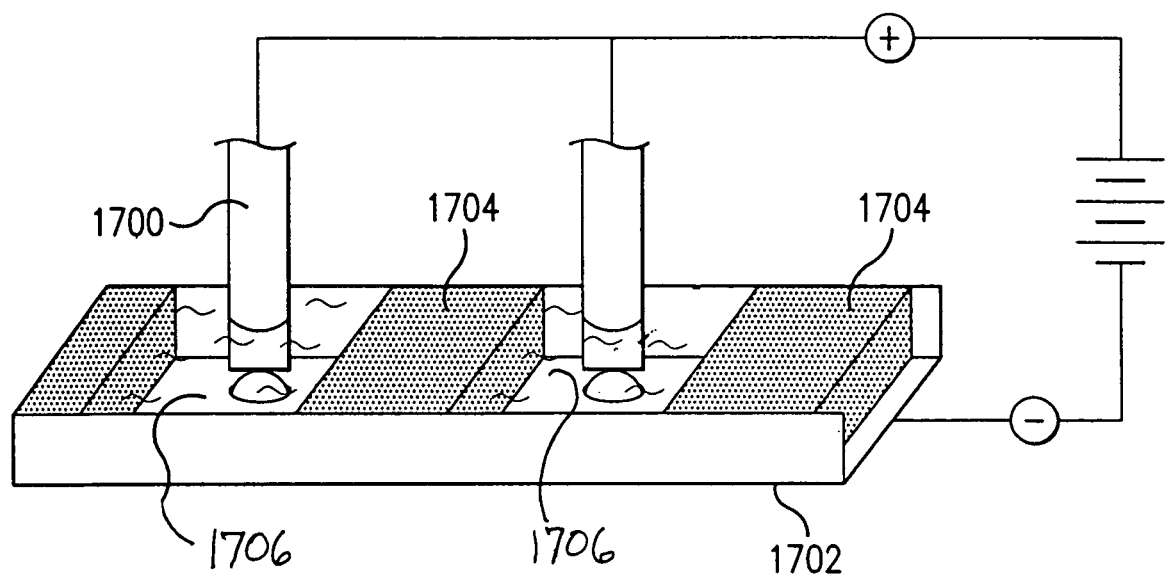
Figure 18:
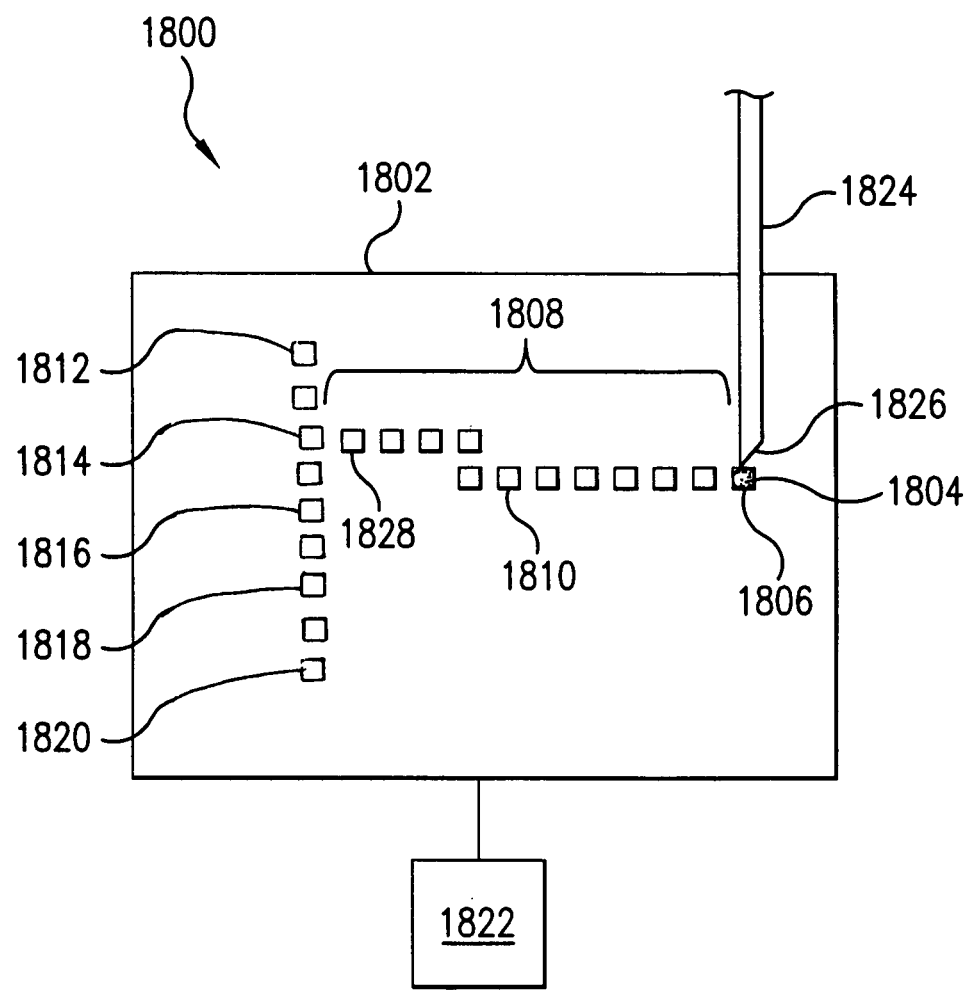
Figure 19:
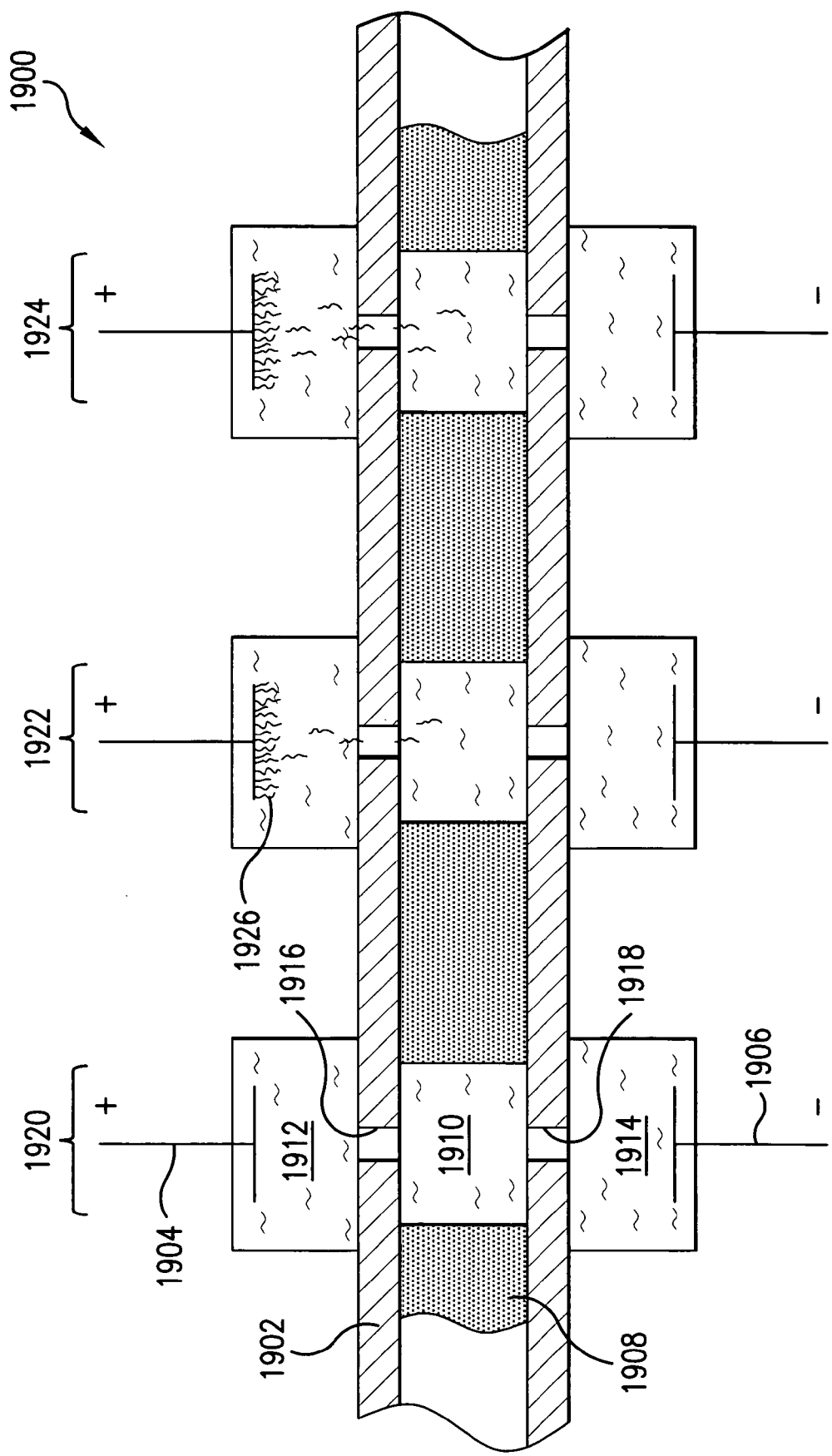
Figure 20:
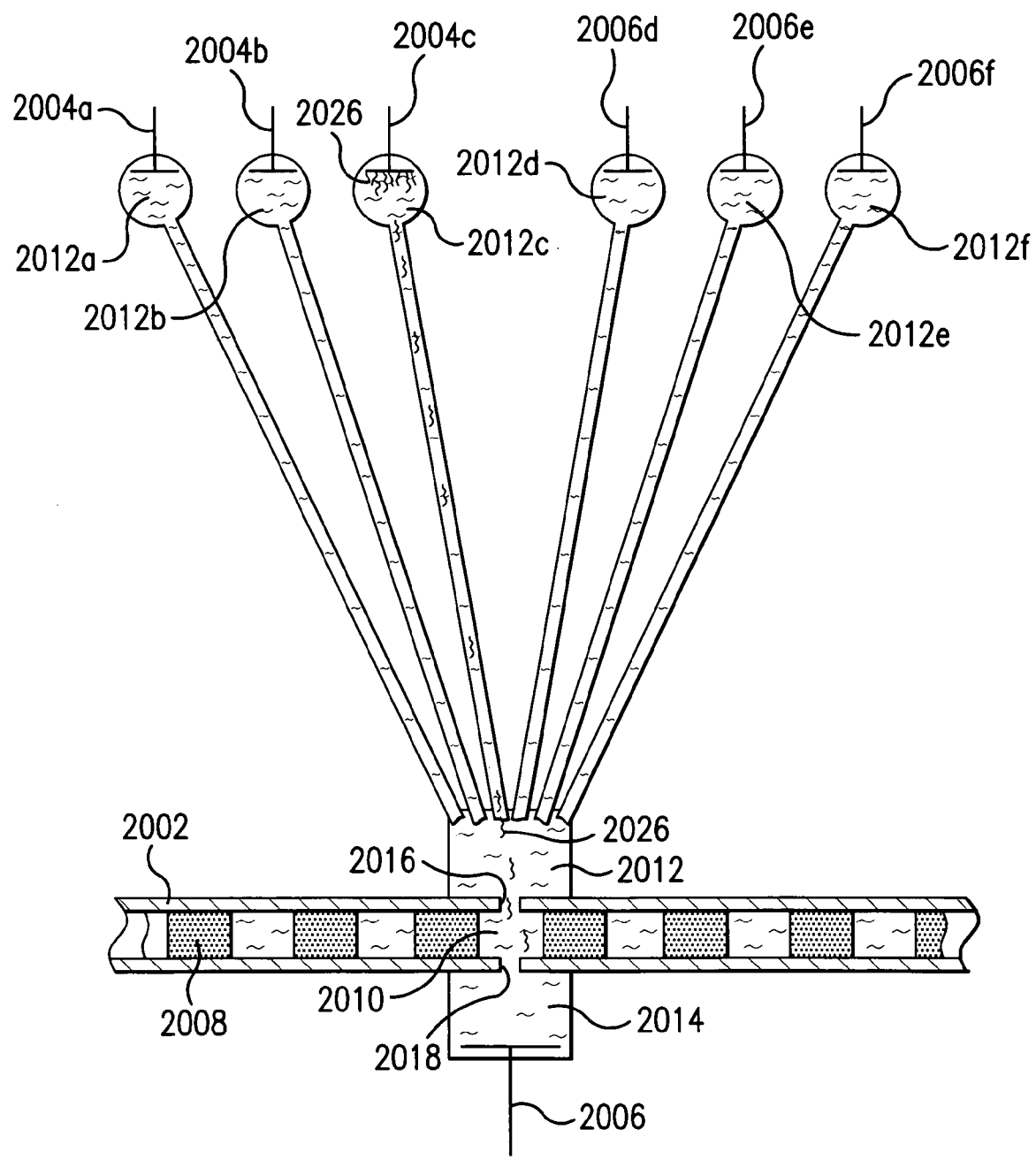
Figure 21:
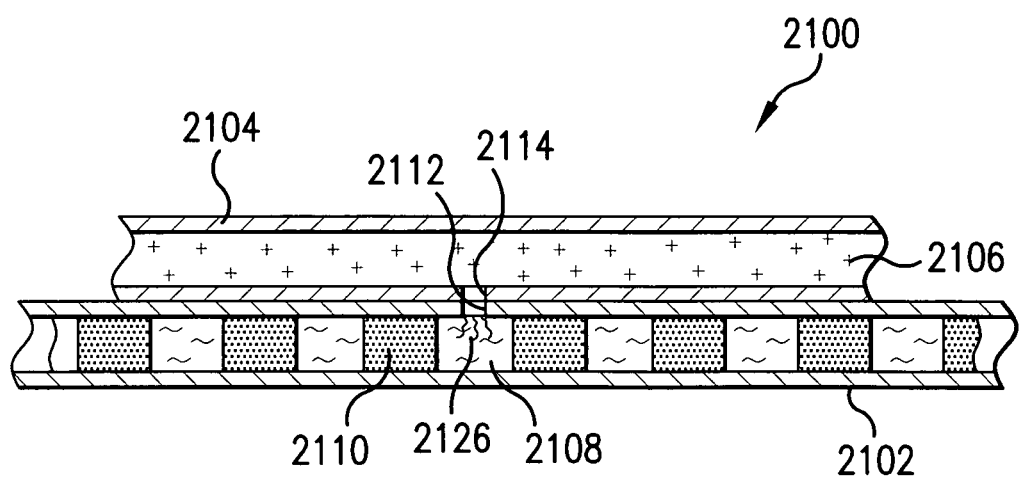
Figure 22A:
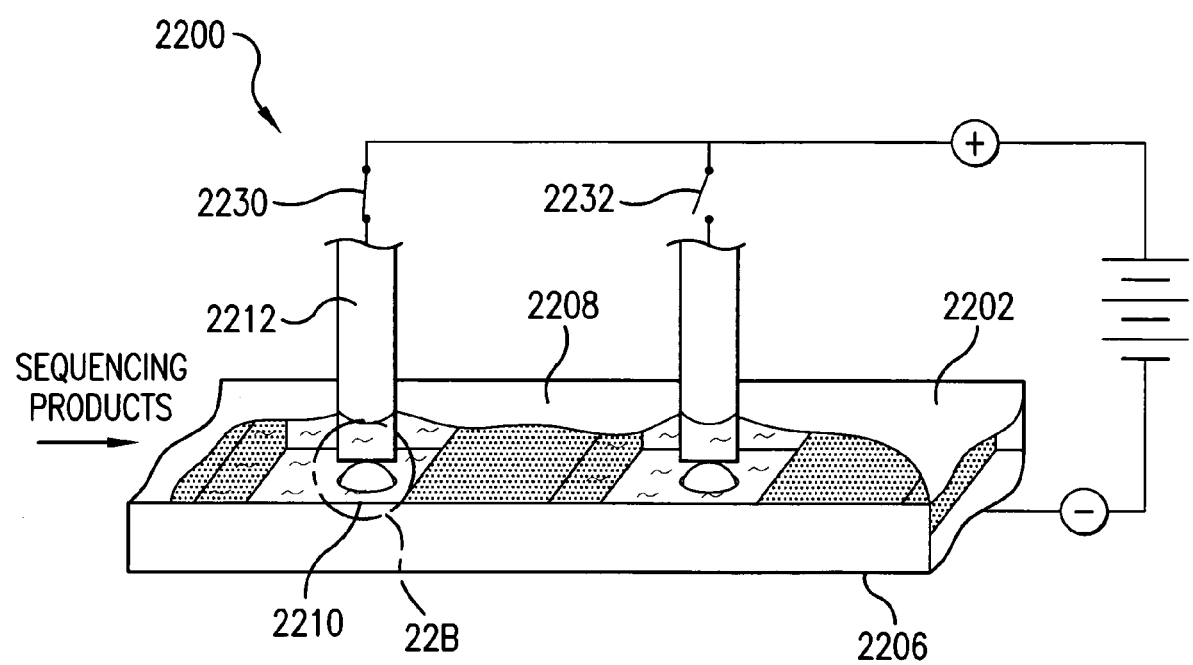
Figure 22B:
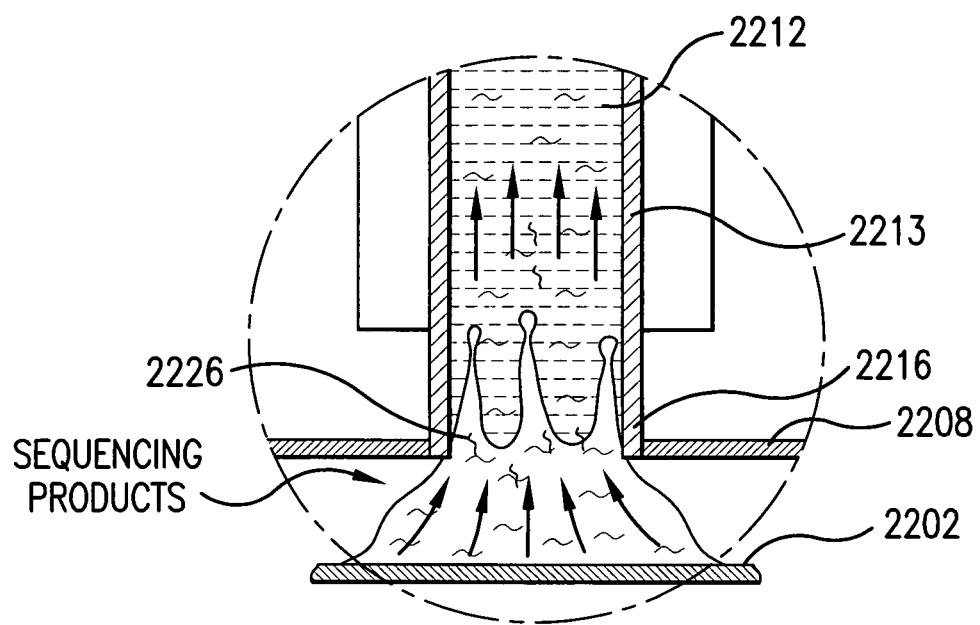

FIG. 17 illustrates injection of sample portions into capillary electrophoresis channels;

FIG. 18 illustrates a perspective view of a system for moving discrete volumes of fluid along electro-wetting pathways to an intake location adjacent a tip of a fluid processing conduit, such as an injector of a capillary electrophoretic injector;

FIG. 19 illustrates electrokinetic sample collection from a slug in a channel wherein an opening in a tubular wall can allow electrical current to pass through a slug, causing negatively charged molecules to migrate toward a positively charged electrode, and positively charged molecules to migrate toward a negatively charged electrode;

FIG. 20 illustrates a multiplexing scheme for electrokinetic sample collection from slugs in a channel;

FIG. 21 illustrates electrokinetic sample collection from slugs in one channel into another channel;

FIG. 22A illustrates a system for electrokinetic sample collection according to various embodiments, in which DNA or other analytes are driven into collection tubes by an electric field applied across a transport channel;

FIG. 22B illustrates an enlarged view of section 22B shown in FIG. 22A.

Figure 29:
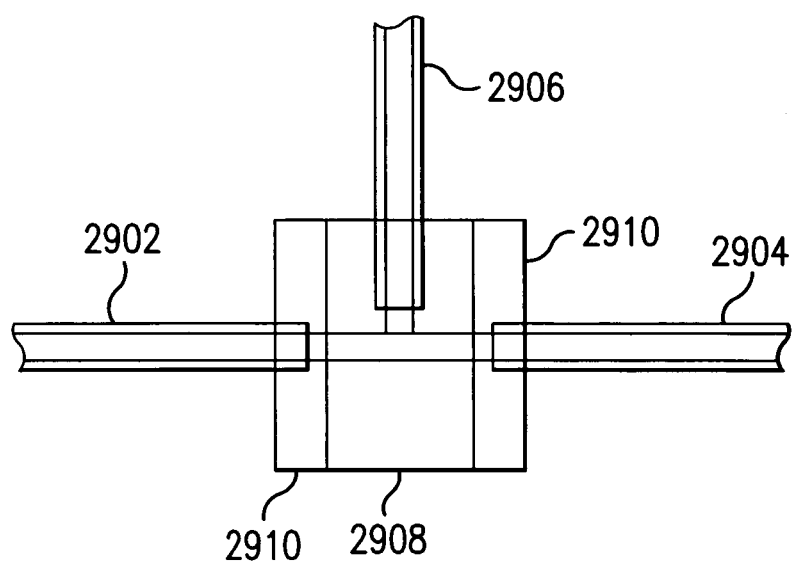
Figure 30:
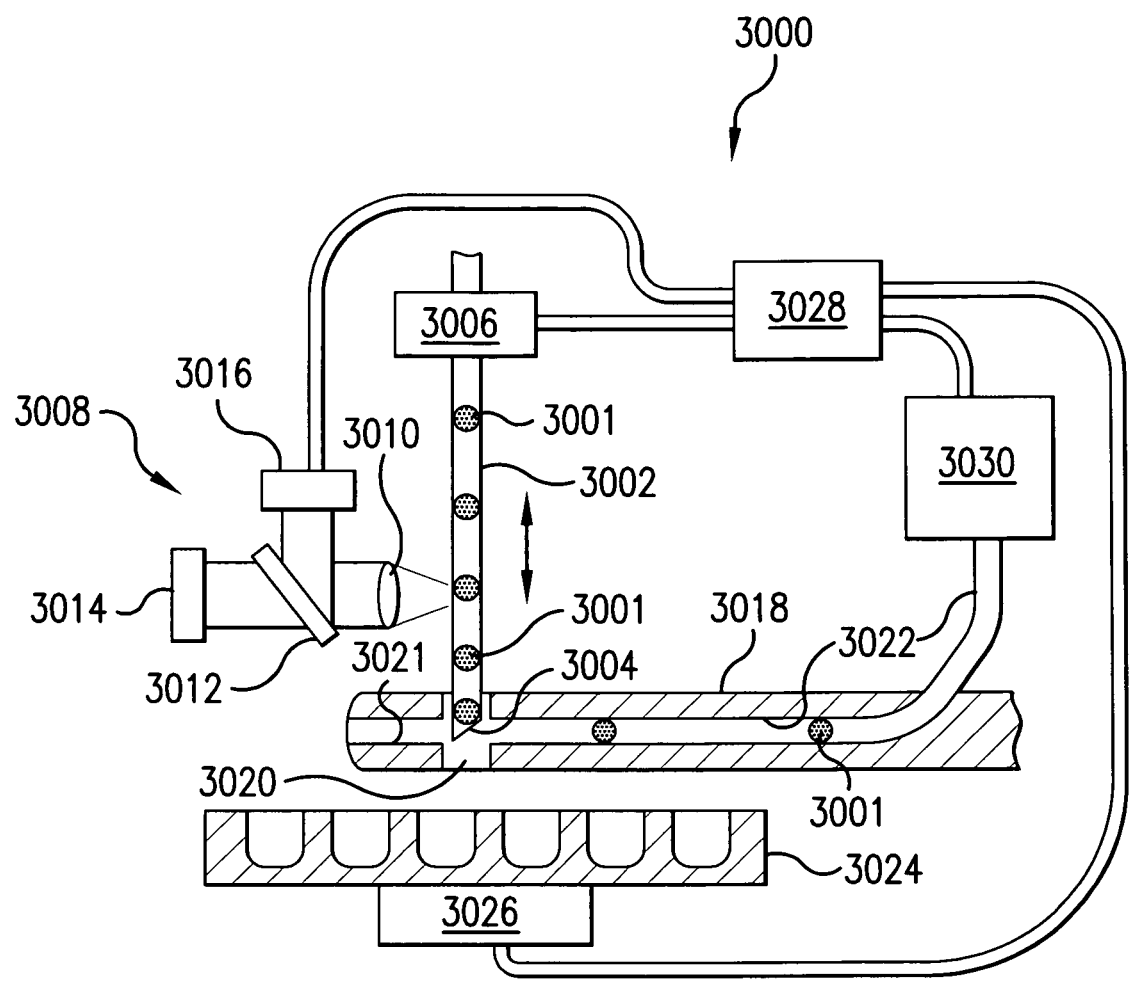
Figure 31:
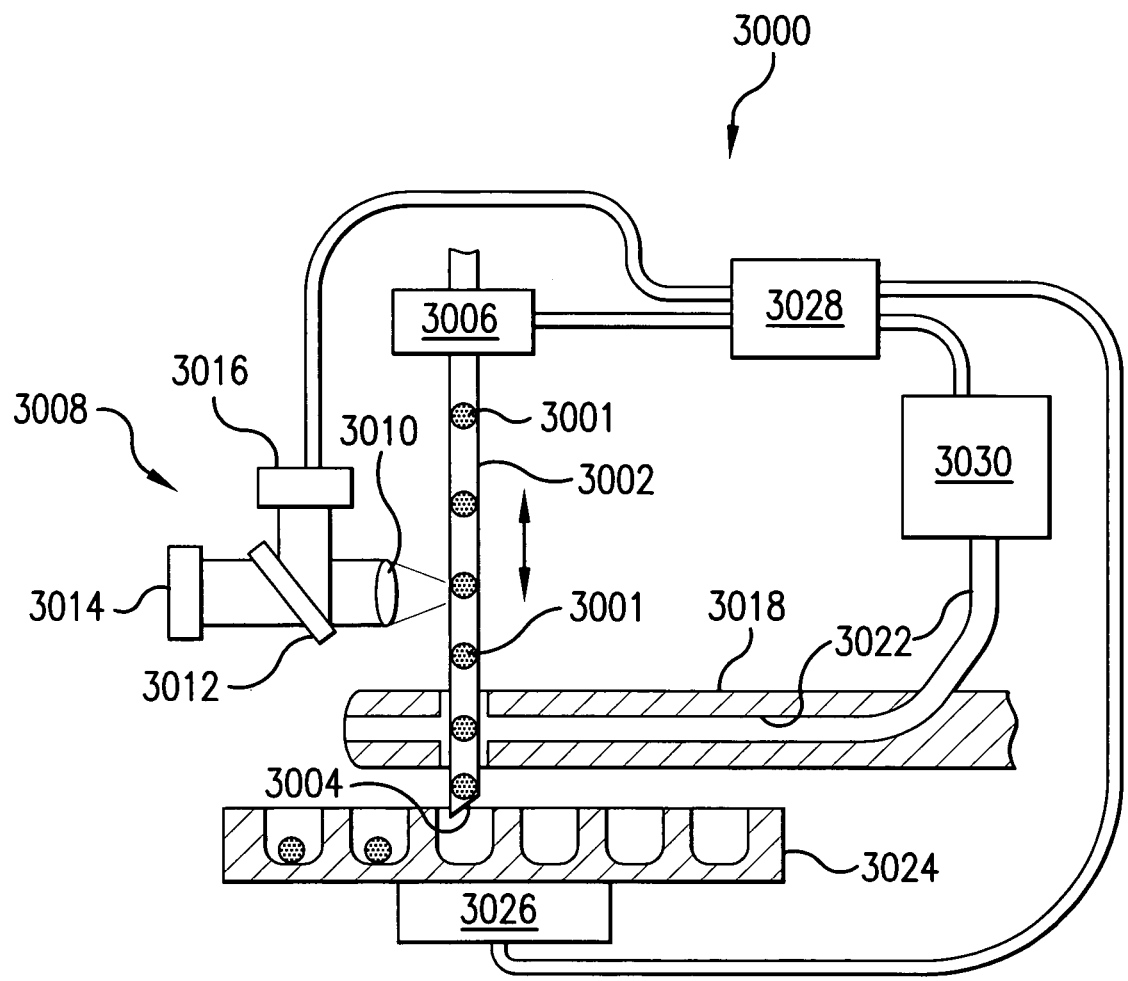

FIGS. 23-28 are top views of various stator and rotor valve systems according to various embodiments;

FIG. 29 is a top view of a slider-in-housing valve that can form or interrupt a three-way fluid communication, according to various embodiments; and FIGS. 30 and 31 are perspective views of a system for depositing aqueous discrete volumes in a sample tray and removing waste.

DESCRIPTION OF VARIOUS EMBODIMENTS

It is to be understood that the following descriptions are exemplary and explanatory only. The accompanying drawings are incorporated in and constitute a part of this application and illustrate several exemplary embodiments with the description. Reference will now be made to various embodiments, examples of which are illustrated in the accompanying drawings. Wherever possible, the same reference numbers are used in the drawings and the description to refer to the same or like parts.

Throughout the application, descriptions of various embodiments use "comprising" language, however, it will be understood by one of skill in the art, that in some specific instances, an embodiment can alternatively be described using the language "consisting essentially of" or "consisting of."

For purposes of better understanding the present teachings and in no way limiting the scope of the teachings, it will be clear to one of skill in the art that the use of the singular includes the plural unless specifically stated otherwise. Therefore, the terms "a," "an" and "at least one" are used interchangeably in this application.

Unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. In some instances, "about" can be understood to mean a given value ±5%. Therefore, for example, about 100 nl, could mean 95-105 nl. At the very least, each numerical parameter should at least be construed in light of the number of reported significant digits and by applying ordinary rounding techniques.

The term "coaxially arranged" should be understood to mean at least two conduits are arranged one inside the other, for example, such that they have a common axis. An example of a coaxial arrangement can comprise a smaller diameter tube within a larger diameter tube.

Reference to "nucleotide" should be understood to mean a phosphate ester of a nucleotide, as a monomer unit or within a nucleic acid. Nucleotides are sometimes denoted as "NTP", or "dNTP" and "ddNTP" to particularly point out the structural features of the ribose sugar. "Nucleotide 5'-triphosphate" can refer to a nucleotide with a triphosphate ester group at the 5' position. The triphosphate ester group can include sulfur substitutions for the various oxygens, for example, α-thio-nucleotide 5'-triphosphates. Nucleotides can comprise a moiety of substitutes, for example, see, U.S. Pat. No. 6,525,183 B2 to Vinayak et al., incorporated herein by reference in its entirety.

The terms "polynucleotide" or "oligonucleotide" or "nucleic acid" can be used interchangeably and includes single-stranded or double-stranded polymers of nucleotide monomers, including 2'-deoxyribonucleotides (DNA) and ribonucleotides (RNA) linked by internucleotide phosphodiester bond linkages, or internucleotide analogs, and associated counter ions, for example, $H^+$, $NH_4^+$, trialkylammonium, $Mg^{2+}$, $Na^+$ and the like. A poly nucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, for example, 5-40 when they are frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted. A labeled polynucleotide can comprise modification at the 5' terminus, 3' terminus, a nucleobase, an internucleotide linkage, a sugar, amino, sulfide, hydroxyl, or carboxyl. See, for example, U.S. Pat. No. 6,316,610 B2 to Lee et al. which is incorporated herein by reference. Similarly, other modifications can be made at the indicated sites as deemed appropriate.

The term "reagent," should be understood to mean any reaction component that in any way affects how a desired reaction can proceed or be analyzed. The reagent can comprise a reactive or non-reactive component. It is not necessary for the reagent to participate in the reaction. The reagent can be a recoverable component comprising for example, a solvent and/or a catalyst. The reagent can comprise a promoter, accelerant, or retardant that is not necessary for a reaction but affects the reaction, for example, affects the rate of the reaction. A reagent can comprise, for example, one member of a binding pair, a buffer, or a DNA that hybridizes to another DNA. The term "reagent" is used synonymously with the term "reaction component."

According to various embodiments, two immiscible fluids can form small volume slugs of one of the fluids in which biochemical reactions and/or analyses can occur. As opposed to reactions in slugs, reactions in partitioned sections have been discussed in U.S. Patent Publication 2004/0180346 to Anderson et al., which is incorporated herein by reference in its entirety. Often, the partitioned sections can be found as microdroplets or globules or spheres in a non-constrained volume. Such partitioned sections have been used in various biochemical and molecular biology procedures. Ghadessy et al., *Nature Biotech.* 22: 755-759 (2004), Dressman et al., *Proc. Natl. Acad Sci. USA* 100:8817-8822 (2003), and Utada et al., *Science* 308:537-541 (2005), all of which are incorporated herein by reference in their entireties.

Methods, apparatuses and systems described herein can use fluids immiscible in each other. Fluids can be said to be immiscible in each other when they can be maintained as separate fluid phases under conditions being used. Immiscible fluids can also be said to be incapable of mixing with each other or attaining a solution with each other. An aqueous liquid and a non-aqueous liquid such as oil can be said to be immiscible with each other. Throughout the specification, reference is made to aqueous slugs. This is merely exemplary and does not necessarily preclude the use or manufacture of non-aqueous liquid slugs in combination with an immiscible liquid.

Figure 3:
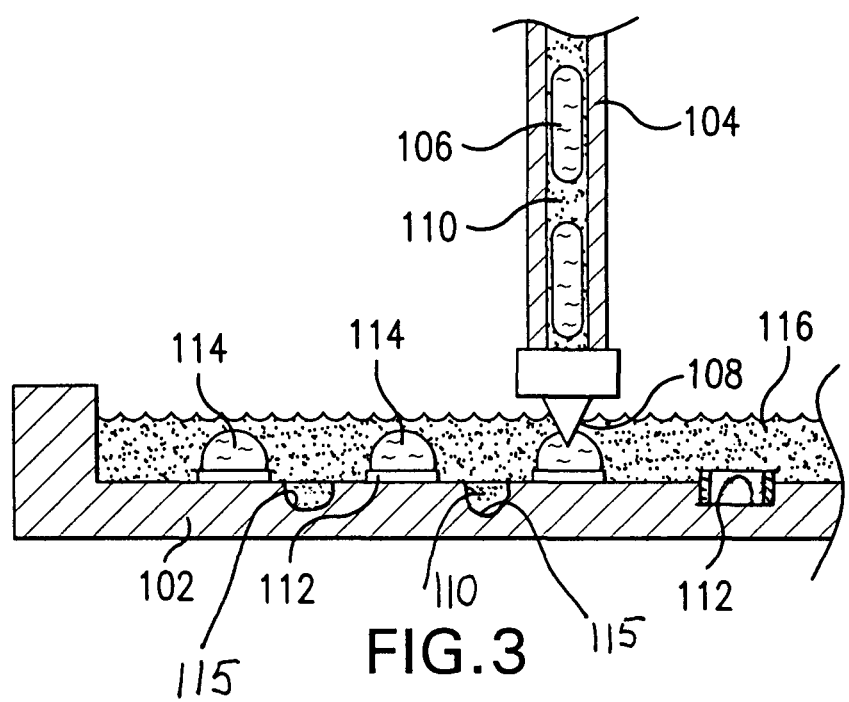
FIG. 3 is an enlarged cross-sectional side view of section A taken from FIG. 2.

While oil and aqueous liquids are immiscible in each other, such a combination does not necessarily form aqueous immiscible-fluid-discrete-volumes in the oil when the two liquids are mixed or placed together. For example, oil can form the disperse phase in a continuous aqueous liquid in a larger volume, as it does in certain salad dressings. For another example, oil and aqueous liquids can merely form aqueous droplets or microdroplets in a larger volume of oil, but not necessarily aqueous immiscible-fluid-discrete-volumes. Aqueous immiscible-fluid-discrete-volumes can form, however, using an apparatus such as, for example, apparatus 100 as shown in FIGS. 2A, 2B, and 3.

Aqueous solutions and oil from separate sources can be combined to form a continuous flowing liquid stream comprising aqueous in immiscible-fluid-discrete-volumes separated from one another by the oil. Because the aqueous immiscible-fluid-discrete-volumes entirely or almost entirely fill the cross-sectional area of the conduit or tube in which they are formed, the resulting stream of aqueous immiscible-fluid-discrete-volumes in oil can exhibit a banded appearance. According to various embodiments, such a pattern can be exhibited by combining any two immiscible fluids with one another. The pattern can be formed throughout the length of the conduit. In various embodiments, a first aqueous immiscible-fluid-discrete-volume can contain different reagents than a second aqueous immiscible-fluid-discrete-volume. In other words, not all aqueous immiscible-fluid-discrete-volumes throughout the conduit need to contain the same reagents.

An aqueous immiscible-fluid-discrete-volume can form a distinct segment bounded by oil and the oil can space the contents of the aqueous immiscible-fluid-discrete-volume from an adjacent aqueous immiscible-fluid-discrete-volume. In various embodiments, liquids other than oil can act as a spacing fluid, provided that the spacing fluid and aqueous fluid are immiscible with respect to each other and provided that they can form individual aqueous immiscible-fluid-discrete-volumes spaced apart from one another by the spacing fluid. In various embodiments, gas can be used as a spacing fluid.

According to various embodiments, methods are provided that refer to processes or actions involved in sample preparation and analysis. It will be understood that in various embodiments a method can be performed in the order of processes as presented, however, in related embodiments, the order can be altered as deemed appropriate by one of skill in the art in order to accomplish a desired objective.

According to various embodiments, a system is provided that can be used as a front-end sample preparation device for high-throughput sequencing, or other applications requiring preparation and/or processing of a plurality of small samples. The samples can comprise, for example, nucleic acids or proteins. The system can be integrated and/or adapted to function with other pieces of equipment adapted for further processing of samples, for example, an ABI 310, ABI 3130, ABI 3130xl, ABI 3700, ABI 3730, or ABI 3730xl capillary electrophoretic analyzer (available from Applied Biosystems, Foster City, Calif.) that can be used for sequencing According to various embodiments, a system is provided that can comprise at least one capillary channel, a substrate separate from and spaced apart from the at least one capillary channel, and an apparatus for moving in a predetermined pattern, relative to one another, the substrate and/or the at least one capillary channel. In various embodiments, the capillary channel can comprise a capillary tube. The substrate can comprise an electrically-conductive surface. In various embodiments, the substrate can comprise linker moieties adapted to bind to a nucleic acid. In other embodiments, the substrate does not necessarily comprise linker moieties.

According to various embodiments, a sample to be deposited on the substrate can comprise the linker moieties, while in other embodiments, the sample can comprise a binding partner for the linker moiety that is already attached to the substrate. Examples of linker moieties and their binding partners can comprise, for example, biotin/streptavidin or streptavidin/biotin combinations.

According to various embodiments, the system can comprise an apparatus for detecting a sample bound to the substrate. The sample can be bound to the substrate through at least one of the linker moieties. A linker moiety can comprise, for example, a thiol group. The at least one linker moiety can comprise a plurality of the same linker moieties or a plurality of different linker moieties, that can comprise, for example, steptavidin moieties or biotin moieties. The electrically-conductive surface can comprise, for example, a gold surface or a gold coating on a base structure. The predetermined pattern for moving an apparatus can be, for example, a raster pattern. In various embodiments, other electrically conductive substrates or coatings on a base structure can be used, for example, platinum substrates or coatings, palladium substrates or coatings, alloy substrates or coatings, and the like. The coating can be segmented into several different sections, as might be desirable when interfacing to a system with a smaller number of capillaries than the number of samples spotted, as when interfacing a four channel capillary system to a 384 position surface. These sections can correspond to the areas useful for performing a single injection with a desired instrument. In some embodiments, the entire coating can be flooded with a sample to be processed.

According to various embodiments, the at least one capillary channel can comprise an inner surface having a maximum inner cross-sectional dimension, that can be, for example, a diameter. The capillary channel can comprise a capillary tube. The capillary tube can have an inner diameter of about 0.5 microns or less, about 1 micron or less, about 10 microns or less, about 50 microns or less, about 100 microns or less, about 300 microns or less, or about 1000 microns or less, or greater than about 1000 microns. In various embodiments, the above dimensions can refer to the maximal cross-sectional dimension of a capillary channel that is not a capillary tube. Such a capillary channel can be rectangular in shape or have another shaped deemed appropriate by one of skill in the art. Various systems and apparati are provided that can include such a capillary channel.

According to various embodiments, the system can comprise at least one capillary channel having a maximum inner cross-sectional dimension and a sample preparation device. The sample preparation device can comprise, an aqueous sample injection unit in fluid communication with the at least one capillary channel, and a spacing fluid injection unit in fluid communication with the at least one capillary channel. The aqueous sample injection unit and the spacing fluid injection unit can comprise separate units each in fluid communication with the at least one capillary channel, and a control unit adapted to flow an aqueous sample and a spacing fluid from the aqueous sample injection unit and the spacing fluid injection unit, respectively, and adapted to inject volumes of aqueous sample and spacing fluid that can respectively form slugs in the at least one capillary channel wherein each slug can have an outer dimension that is equal to the maximum inner cross-sectional dimension. In various embodiments, the sample injection unit and the spacing fluid injection unit can comprise a single unit in communication with the at least one capillary channel. In various embodiments, the system can comprise a non-aqueous liquid source in fluid communication with the spacing fluid injection unit and an aqueous sample source in fluid communication with the aqueous sample injection unit.

According to various embodiments, the system can comprise a detection device adapted to detect a component of the aqueous sample source or a reaction product thereof. The detection device can comprise, for example, a spectrophotometer or a fluorometer. Other detection devices, for example, a photomultiplier tube (PMT), photodiode, or charge-coupled device (CCD) can also be used.

According to various embodiments, the system can comprise at least one capillary channel comprising an inner surface. The inner surface of the at least one capillary channel can comprise linker moieties. The linker moieties can comprise at least one of steptavidin moieties or biotin moieties. In various embodiments, the capillary channel can be a capillary tube.

According to various embodiments, the system can comprise a capillary electrophoretic sequencer adapted to inject a sample component when a sample component is disposed on the electrically conductive surface. The sample component, however, can be injected into a device other than an electrophoretic sequencer, as deemed appropriate by one of skill in the art, or transferred into another system for further processing.

According to various embodiments, the electrically conductive surface can comprise channels. The channels can comprise linker moieties adapted to bind to a nucleic acid.

According to various embodiments, the electrically conductive surface can comprise linker moieties adapted to bind to a nucleic acid. The linker moieties can comprise a plurality of the same linker moiety.

According to various embodiments a system is provided that can comprise an aqueous sample injection unit in fluid communication with at least one capillary channel having a maximum inner cross-sectional dimension, a spacing fluid injection unit in fluid communication with the at least one capillary channel, the aqueous sample injection unit and the spacing fluid injection unit can comprise separate units each in fluid communication with the at least one capillary channel. The system can comprise an electrically conductive substrate and a capillary electrophoresis sequencer. In various embodiments, the system can comprise, a control unit adapted to flow an aqueous sample and a spacing fluid from the aqueous sample injection unit and the spacing fluid injection unit, respectively. The aqueous sample injection unit and the spacing fluid injection unit can be adapted to inject volumes of aqueous sample and spacing fluid to form slugs in the at least one capillary channel wherein each slug has an outer dimension that is about equal to the maximum inner cross-sectional dimension. In various embodiments, the system can comprise an electrically conductive substrate that can comprise at least one channel and a capillary electrophoretic sequencer adapted to inject a sample component from the substrate when a sample component is disposed on the electrically-conductive surface. The electrically conductive surface can comprise linker moieties adapted to bind to a nucleic acid. The linker moieties can comprise a plurality of the same linker moiety.

According to various embodiments, a method is provided. The method can comprise, forming in a capillary channel a plurality of aqueous sample slugs spaced apart from one another by slugs of spacing fluid, at least one of the aqueous sample slugs comprising at least one target analyte, and dispensing the aqueous sample slugs one-at-a-time from the capillary channel onto a substrate to form a pattern of spaced apart aqueous samples on the substrate, the substrate comprising at least one electrically conductive surface that comprises at least one linker moiety bound thereto, wherein the at least one linker moiety is adapted to capture the at least one target analyte.

According to various embodiments, partitioned aqueous compartments can be prepared for dispensing onto a substrate by methods other than preparing slugs in a capillary channel. Examples of preparations of partitioned sample can comprise forming aqueous compartmentalized sample in a non-constrained volume such as would be found in a capillary channel or capillary tube. The compartments can be formed as a result of emulsification as described, for example, by Ghadessy, et al., *Proc. Natl. Acad. Sci. USA* 98:4522-4557 (2001), which is incorporated in its entirety herein by reference.

According to various embodiments, the method can comprise capturing the at least one target analyte with the at least one linker moiety to form at least one captured target analyte. In various embodiments, the method can comprise contacting the electrically conductive surface with a mixture of sequencing reaction components after capturing the at least one target analyte.

According to various embodiments, the at least one electrically conductive surface of the substrate can comprise a gold-coated surface or other metal-coated surfaces. In various embodiments, the at least one target analyte can comprise at least one target nucleic acid sequence.

According to various embodiments, the method can comprise reacting the at least one captured target analyte with a reagent mixture to form at least one target analyte product. In various embodiments, the method can comprise positioning a collection device adjacent the at least one target analyte product and injecting at least a portion of the at least one target analyte product into the collection device. The collection device can comprise a capillary of a capillary electrophoretic analyzer.

According to various embodiments, injecting in the method can comprise applying a potential to the at least one electrically conductive surface.

According to various embodiments, forming the pattern of spaced apart aqueous samples can comprise forming a plurality of rows of aqueous samples.

According to various embodiments, a method is provided that can comprise migrating components in a sample on a substrate surface into a capillary channel, for example, a capillary tube. The components can be injected, for example, by electrokinetic force. Migration of the charged components can be accomplished by creating an electric field in a device or system. The system can comprise an electric field generator for producing electrokinetic force. Conditions that can affect electrokinetic injection of DNA samples, can comprise, sample ionic strength, buffering capacity, the quality of the separation matrix being used, the voltage, and the electrical field. Electrokinetic injection can rely on the application of an initial voltage through a passage to initiate sufficient ion flow to bring the sample into the passage and thereafter producing electrophoretic separation conditions. A method of electrokinetic injection has been described in U.S. Pat. No. 6,569,305, issued May 27, 2003, which is incorporated in its entirety herein by reference.

According to various embodiments, a method is provided that can comprise forming in a capillary channel a plurality of aqueous sample slugs, at least one of the aqueous sample slugs comprising at least one target analyte comprising at least one respective linkage group, and dispensing the aqueous sample slugs one-at-a-time from the capillary channel onto a substrate to form a pattern of aqueous samples on the substrate, the substrate comprising an electrically conductive surface adapted to covalently bond the at least one respective linkage group to form an attached analyte.

According to various embodiments, the method can comprise covalently bonding the at least one linkage group to the electrically conductive surface to form at least one captured target analyte. In various embodiments, the method can comprise contacting the electrically conductive surface with a mixture of sequencing reaction components after the covalently bonding. In other embodiments, the method can comprise reacting the at least one captured target analyte with a reagent mixture to form at least one target analyte product.

According to various embodiments, the method can comprise positioning a collection device adjacent the at least one target analyte product and injecting at least a portion of the at least one target analyte product into the collection device. The collection device can comprise a capillary of a capillary electrophoretic analyzer.

According to various embodiments, injecting in the method can comprise applying a potential to the electrically conductive surface of the substrate. The electrically conductive surface can comprise a gold-coated surface. In various embodiments, the at least one target analyte can comprise at least one target nucleic acid sequence. In various embodiments, forming the pattern of aqueous samples can comprise forming a plurality of rows of aqueous samples.

According to various embodiments, a method is provided that can comprise amplifying DNA in a plurality of aqueous sample slugs in a capillary channel to form amplicons, each aqueous slug being separated from an adjacent aqueous slug by at least one oil slug, rastering or moving the capillary channel comprising the amplicons over a substrate and depositing the amplicons from the capillary channel onto the substrate, the substrate comprising an electrically conductive surface, attaching the amplicons to the electrically conductive surface, contacting the substrate with a sequencing reaction mixture to form at least one dye-labeled spot, positioning a capillary of a capillary electrophoretic analyzer over the at least one dye-labeled spot, electrically contacting the dye-labeled spot with the capillary, and injecting one or more components from the dye-labeled spot into the capillary.

According to various embodiments, amplifying can comprise incorporating a 5'-sulfhydryl group into a DNA molecule. In various embodiments, the surface can comprise an electrically conductive surface. The electrically conductive surface can comprise a gold surface. In various embodiments, the surface can comprise a binding moiety.

According to various embodiments, the method can comprise washing the electrically conductive surface with a denaturing solution after depositing the amplicons from the capillary onto the electrically conductive surface. In various embodiments, the sequencing reaction mixture can comprise a primer and a dye-labeled terminator and the method comprises reacting the amplicons with the primer and the dye-labeled terminator to form the dye-labeled spot.

According to various embodiments, the method can comprise imaging the electrically conductive surface and determining a location of the dye-labeled spot. In various embodiments, the method can comprise analyzing the one or more components in the capillary electrophoretic analyzer.

According to various embodiments, the electrically conductive surface used in the method can comprise reactive groups. The reactive groups can comprise one or more of carboxy groups, amino groups, and hydroxyl groups.

According to various embodiments, the substrate can comprise a material that can be electrically conductive or can be a non-conductive material coated with an electrically conductive layer. The substrate can comprise, for example, glass, plastics (for example, polypropylene, polystyrene, polycarbonante and mixtures thereof), inert materials or electrically conductive metals. Electrically conductive metals can comprise gold or platinum. If a substrate is not electrically conductive, it can be coated with an electrically conductive coating. Electrically conductive coatings can comprise, for example, gold or platinum. In various embodiments, electrically conductive metals can comprise platinum group metals, for example, ruthenium, osmium, palladium, rhodium, and iridium (See U.S. Pat. No. 5,645,930 to Tsou et al., issued Jul. 8, 1997, which is incorporated herein in its entirety by reference.)

In various embodiments, an electrically conductive substrate can be covered with an insulating material or dielectric material, for example a plastic, and the combination of insulating material or dielectric material with electrically conductive material can act as a capacitor when a potential is applied. When the potential is applied to the substrate covered with plastic, negative charged molecules can move into the capillary, for example, a DNA molecule. In various embodiments, moieties can be attached to the non-conductive surface for binding to nucleic acids or other sample of interest.

According to various embodiments, a non-conductive substrate can be coated with a thin electrically conductive film, for example, a gold film.

Other methods of coating a surface with conductive films are known, for example, production of nanoparticle thin films. See, Sastry, *Pure Appl. Chem.* 74:1621-1630 (2002), which is incorporated in its entirety herein by reference. Example of films formed by layer-by layer nanoparticle assembly that can be driven by electrostatic interactions can comprise, for example, cationic and anionic polyelectrolytes as well as multilayer structure comprising combinations of colloidal particles, for example, biomacro-molecules such as DNA. A gold film can be formed from a gold colloidal solution.

Gold-coated substrates can be prepared, for example, by sputtering a nanometer layer of chromium and gold onto a glass slide. Thiolated DNA can then be attached to the gold-coated substrate. Additional information concerning gold-coated substrates, thiolation of DNA, and other methods immobilizing DNA to a substrate can be found in Csaki, et al., *Nucl. Acids Res.* 29:No. 16 e81(2001), Peelen, et al., *Langmuir* 21, 266-271 (2005) which are incorporated in their entireties by reference herein.

According to various embodiments, DNA can be amplified by a PCR. Starting material comprising, DNA fragments with primer sites A and B can be diluted, and PCR with primers A and B can be used to amplify single DNA fragments in aqueous solution (for example, in capillaries with aqueous slugs separated by oil). Primer A (or forward primer) can contain a 5' sulfhydryl group Primer B (or reverse primer) can contain a 5' sulfhydryl group. The amplification can be performed in a system that uses alternating partitioned portions, for example, spaced apart slugs of an aqueous solution comprising DNA and non-aqueous separating liquid, for example, an oil. In various embodiments, the sample can be prepared in bulk and then distributed or disposed onto a substrate for subsequent injection into a device for further analysis or processing. Further analysis can comprise analysis in a capillary electrophoresis device.

In some embodiments slugs containing both primer A and primer B can be deposited on different spots, at least one spot of which reacts only with primer A and at least one spot of which reacts only with primer B. In some embodiments, two different slugs are provided with reactants for only primer A or primer B and can be deposited on different locations on the substrate that react with both primer A or primer B. In some embodiments, only primer A is included in or added to a first half of the slug while only primer B is included in or added to a separate, second half of the slug. A cycle sequencing reaction can then be carried out on primers bound to the surface which can hybridize to a free floating amplicon with an appropriate complimentary tail.

In some embodiments, a spot having an analyte bound thereto can be contacted with an injection fluid. The injection fluid can comprise an aqueous solution, low-salt buffer, for example, of micromolar concentration. The injection fluid can facilitate injection of the analyte into a capillary electrophoresis capillary. Once contacted with the injection fluid, the bound analyte can be free from the surface by application of a relative potential between the surface an the capillary.

Amplifying of a nucleic acid can comprise a thermal cycling nucleic acid sequence amplification process or an isothermal nucleic acid sequence amplification process. If a thermal cycling nucleic acid sequence amplification process is used, the process can comprise, for example, a polymerase chain reaction (PCR). The nucleic acid sequence amplification reaction can comprise an exponential amplification process, for example, PCR, or a linear amplification process, as can occur during, for example, during Sanger cycle sequencing. In various embodiments, other nucleic acid amplification processes can comprise, for example, ligase chain reaction (LCR), nucleic acid sequence based amplification (NASBA), Q-beta replicase (QB) amplification, or strand displacement amplification (SDA). These alternatives, as well as others known to one skilled in the art can be used either by themselves or in combination with PCR to amplify nucleic acids, for example, in a multiplexed preparation.

Nucleic acid sequence processing methods can comprise a first type of nucleic acid amplification reaction followed by one or more of a second different type of amplification reaction, and/or detection assay reaction, can be carried out, for example, as described in U.S. patent application Ser. No. 60/699,782 to Faulstich et al., filed Jul. 15, 2005, and in U.S. patent application Ser. No. 11/487,729 to Faulstich et al., filed Jul. 17, 2006, which are incorporated herein in their entireties by reference.

After amplification or other nucleic acid manipulation, the capillary can be rastered or otherwise moved across a gold surface, while the contents of the capillary are pumped out. A "snail trail" can result in alternating aqueous and non-aqueous deposits on a substrate surface. The sulfhydryl groups can form a linkage to a gold surface, thereby immobilizing PCR amplicons to the surface wherever the capillary tip is placed and a drop of aqueous solution is deposited. The speed of pumping and the speed of rastering the capillary across the gold surface can be adjusted such that amplicons are appropriately spaced and do not mix. The speed can optionally be further modulated such that aqueous slugs are placed at intervals which correspond to spacing associated with a capillary electrophoresis instrument. Similarly, the rows can optionally be spaced at intervals matching those of an electrophoresis instrument. A detector in combination with a controller can be used to insure that the aqueous slugs are properly spaced. In various embodiments, DNA can be attached to the substrate or a material covering the substrate using a linkages other than a thiol linkage, for example, a biotin-streptavidin linkage. Examples of methods for attaching a target molecule to a surface can be found, for example, in U.S. Pat. No. 6,465, 178 B2, issued Oct. 15, 2002, and U.S. Pat. No. 6,057,100, issued May 2, 2000 which are incorporated herein in their entireties by reference.

Once the amplicons have covalently attached to a surface, the surface can be washed under denaturing conditions in order to remove one strand of an amplicon duplex (i.e., the non-sulfhydryl containing strand primed by primer B, or primer A, as appropriate).

The surface can then be contacted with a sequencing mixture containing primer B, and one round of standard dye-labeled terminator sequencing can be performed. The surface is then washed under non-denaturing conditions to remove unreacted triphosphates and salts. The dye-labeled sequencing products remain hybridized to the template strands, which are covalently bound to the gold surface. In some embodiments, a sequencing reaction can be carried out on the plate as described herein or the plate can be used for cleaning-up bound analytes.

Imaging of the electrically conductive surface, for example, a gold surface, which can comprise DNA samples can be used to detect the location of each spot on the substrate containing labeled sequencing products. Detecting can be, for example, the result of fluorescent imaging of DNA containing a fluorescent label. In various embodiments, a detector can comprise photodiodes, photomultiplier tubes, or charge-coupled device (CCD) cameras. The CCD camera can be, for example, an intensified CCD (ICCD). Examples of additional detectors and methods for labeling DNA, can be found in U.S. Pat. No. 6,255,083 B1, issued Jul. 3, 2003, which is incorporated in its entirety herein by reference.

After locating a spot comprising a labeled sequencing product, the end of a sequencing capillary can then positioned directly over a spot and the sequencing product fragments solubilized, for example, by raising the temperature of the sequencing capillary enough to force a small amount of polymer out of the end of the capillary to contact the gold surface/sequencing products or by pumping a small amount of the polymer out of the end of the capillary, or by forming an aqueous bridge between the gold surface/sequencing product and the sequencing capillary. Then the solubilized fragments are injected into the sequencing capillary by applying a voltage across the gold surface. Without wishing to be held to any specific theory of action, it is believed that surrounding spots are not injected because 1) they are dry and/or 2) the only path of electrical conduction is through the capillary contact with the spot of interest.

According to various embodiments, the system can comprise a capillary channel dimensioned so that a migration of charged components in a fluid, from the substrate into the capillary can occur. The capillary channel can have one or more maximum cross-sectional dimensions of about 5 millimeters or less, for example, about 2 millimeters or less, about 1 millimeter or less, or about 0.5 millimeter or less. In various embodiments the capillary channel has an inner surface and a maximum diameter of about 5 millimeter or less, for example, about 2 millimeters or less, about 1 millimeter or less, or about 0.5 millimeter or less and dimension is a diameter of a capillary tube. Other sizes can include 50 microns, or, for example, from about 25 microns to about 75 microns.

While electrokinetic force can move a sample from the substrate into a capillary channel, this does not preclude the method from creating a pressure differential between the sample on the substrate and the capillary channel. Such a gradient and/or electrokinetic flow can play a role in migrating or moving the sample. According to various embodiments, a pressure differential can be generated by activating a pump.

The methods and systems can provide reductions in sequencing reagent consumption. Assuming i) a standard 1 inch by 3 inch microscope slide coated with gold, ii) aqueous slugs of 1 nl, iii) the aqueous phase forms droplets on a gold surface with 90° contact angles, and iv) the surface of the 1×3 inch slide can be covered with 1 ml of sequencing reaction liquid, the following exemplary calculation can be made, however, such calculation should in no way limit the scope of the claims. Other formats, for example, a standard 96-well microtiter plate or the footprint thereof can be used as appropriate substrates.

A one nanoliter droplet can be calculated to form a spot with a diameter of 156 μm. Stearic interference can limit the packing density of double stranded DNA to a diameter of about 2 nanometers. Taking a conservative packing density of only one DNA per 20 nm$^2$, a 156 μm diameter feature can be calculated to contain $9.6 \times 10^8$ DNA molecules. Assuming a sequencing reaction can generate termination products between +1 and +3,000 bp, each fragment size will contain on average $3 \times 10^5$ molecules. If even 10% of these are electrokinetically injected, that can result in 30,000 molecules per peak, which can be detected with current sequencing instrumentation.

If a snail trail deposition is adjusted such that there are three diameters (468 micrometers) of blank space between amplicon features or spots, a 1×3 inch surface can hold 3,000 features. In other words, 3,000 sequencing regions can be formed on a 1×3 inch "plate," which uses 1 ml of sequencing reaction, or 0.3 µl per sequencing reaction. This can represent an order of magnitude reduction in sequencing reagent consumption, thereby reducing the costs of such preparation.

The method and systems can provide high throughput shotgun sequencing projects without the use of bacterial cloning, clone picking, plasmid preparation, or microtiter plate-based sequencing reactions. The method and systems can also provide high throughput preparations for genetic analysis and/or other diagnostic methods using nucleic acids and/or requiring multiple sampling of small volumes.

According to various embodiments, the method can involve the use of a system or device that provides sample slugs to a substrate or capillary channel, for further processing. The sample slugs can each comprise a single target nucleic acid molecule or amplification product from a single nucleic acid molecule or analysis, for example, in a solution or mixture. Further processing of the nucleic acid can comprise amplifying the nucleic acid and/or sequencing the nucleic acid. Further processing of molecules other than nucleic acids is also within the realm of the present teachings as will be appreciated by those of skill in the art. According to various embodiments, the slugs can either be flowed continuously or can be intermittently stationary in a capillary channel during amplification and/or other procedures. Sample volumes comprising a nucleic acid to be amplified or processed can be less than about 100 µl, less than about 1 µl, less than about 500 nl, less than about 250 nl, less than about 100 nl, less than about 50 nl, less than one nl, less than 100 pl, or less than 10 pl.

According to various embodiments, the sequencing methods that can be carried out using the devices and methods described herein and can comprise direct sequencing, stepwise sequencing, Sanger sequencing, cycle sequencing, sequencing by synthesis, fluorescent in situ sequencing (FISSEQ), sequencing by hybridization (SBH), forward/reverse sequencing, pyrosequencing, sequencing using boronated oligonucleotides, electrophoretic, or microelectrophoretic sequencing, capillary electrophoretic sequencing, or other nucleic acid sequencing methods known in the art that can be applied to small sample volumes. Exemplary descriptions of sequencing in various volumes can be found in U.S. Pat. No. 5,846,727 to Soper et al., U.S. Pat. No. 5,405,746 to Uhlen, U.S. Pat. No. 6,154,707 to Livak et al., and Soper et al., *Anal. Chem.* 70:4036-4043 (1998), all of which are incorporated herein in their entireties by reference.

According to various embodiments, the methods and systems can use TaqMan® reagents (Applied Biosystems, Cal.), for example, probes or primers. For example, see U.S. Pat. No. 6,154,707 to Livak, et al., incorporated herein in its entirety by reference. Other related methods known to one of skill in the art can also be used as deemed appropriate. Such reagents can be used in methods of analyzing DNA or RNA.

According to various embodiments, labeling of molecules can be accomplished, for example, using an affinity labeled primer. Primers can comprise an affinity moiety, thereby allowing for the binding of reaction products to affinity-binding moieties. For example, a specific binding pair comprising biotin and streptavidin can be employed. A biotin affinity moiety can be incorporated into a primer, and a streptavidin binding moiety can be used to bind, or can bind and immobilize the biotin-incorporated primer. Unbound unincorporated reaction components can be removed, and the nucleic acid strand complementary to the biotin-bearing strand can be isolated and analyzed. It will be appreciated that the members of a specific binding pair can be switched and still accomplish the desired binding to the surface of the substrate, for example, the streptavidin can be attached to the primer and act as an affinity moiety, and the biotin can be attached to a solid support and act as a binding moiety. The procedures used for binding, and/or binding and immobilization, are well known to one of skill in the art. Bound, but unused single-stranded primer can be later digested.

According to various embodiments, a double-stranded amplicon with a binding moiety can be attached or immobilized to an inner surface of a capillary tube or other capillary channel. Various functional groups can be used to accomplish attachment or immobilization of nucleic acids. A functional group can be any compound that can be incorporated into or attached to an oligonucleotide and that has a strong interaction to a molecule that can be immobilized on a solid-support. If elevated reaction temperature is used to analyze or process an attached molecule, stability of the functional groups at such temperatures can be a consideration.

According to various embodiments, samples of interest can be prepared in a capillary tube and then dispensed onto a substrate from which the samples are electrokinetically injected into, for example, a capillary electrophoresis sequencing apparatus. In other embodiments, samples can be directly processed in a capillary channel formed in an electrically conductive substrate, thereby eliminating the dispensing step. Small volumes, for example, slugs can be used in such channels. Attached to the surfaces of such channels can be binding moieties and/or specific nucleic acid sequences complimentary to a sample of interest. Once the sample of interest is bound to a location, the sample can then be injected into, for example, a capillary electrophoresis apparatus for further analysis.

Examples of binding pairs can comprise biotin-avidin, biotin-streptavidin, or cystein-thiol groups. An example, of a functional group for binding nucleic acids to a surface is 11-biotin-dUTP. A biotin-avidin-biotin three component linkage of a molecule to be attached to a surface can also be used. If an oligonucleotide is attached to a surface, interaction between binding components on the surface and the oligonucleotide should be stable during the amplification and/or other procedures. In various embodiments, directly or indirectly, light activated or heat activated reactive groups on a primer that can react with a surface coated reactive group, can be used.

Incorporation of a terminal functional group into a nucleic acid being synthesized can be accomplished, for example, with a polymerase, such as Klenow, T7, or reverse transcriptase. Alternatively, a functional group of interest can be attached to an oligonucleotide by ligation to a suitable oligonucleotide that has already been synthesized.

According to various embodiments, the system can be used for carrying out sequence-specific nucleic acid reactions involving a target nucleic acid. Reaction-specific reagents can be releasably bound to the wall of a capillary channel, for example, through duplex formation with immobilized complimentary-sequence oligonucleotides, or by ligand attachment to an immobilized binding molecule. Complimentary sequence oligonucleotides can comprise zip-code sequences or other sequences as deemed appropriate by one of skill in the art.

According to various embodiments, methods and systems for microfluidic sample handling are provided. The methods can be used, for example, to perform shotgun sequencing, as well as other methods of nucleic acid analysis. DNA to be sequenced can be prepared by standard techniques, for example, shearing of genomic DNA of interest. Primers can be attached to the two ends of the sheared DNA for further manipulation.

Nucleic acids for sequencing reactions can be prepared by methods known to one of skill in the art. Methods can comprise chemical synthesis, or shotgun cloning in bacteria or yeast, as are well-known to those in the art. According to various embodiments, nucleic acids can also be prepared by enzymatic methods, for example, by a PCR reaction or a chain ligase reaction. Enzymatic methods of amplification can provide an alternative to the biological amplification of cloning in bacteria or yeast. Enzymatic amplification can provide sufficient DNA for micro- or nano-sequencing reactions.

According to various embodiments, an amplicon can be obtained in an aqueous slug by the described methods. Amplification of target nucleic acids, with detection resulting from the increased amount of target relative to the copy number present in the starting material, can be accomplished. Suitable amplification procedures can include the polymerase chain reaction, and isothermal amplification, although it will be appreciated that other amplification strategies might be employed in order to generate product.

According to various embodiments, an enzyme that polymerizes nucleotide triphosphates into amplified fragments can be a heat-resistant DNA polymerase. Polymerases that can be used in a method of the present teachings comprise DNA polymerases from such organisms as *Thermus aquaticus, Thermus thermophilus, Thermococcus litoralis, Bacillus stearothermophilus, Thermotoga maritirna* and *Pyrococcus* ssp. The enzyme can be isolated from source bacteria, produced by recombinant DNA technology or purchased from commercial sources. Exemplary DNA polymerases that can be used include those available from Applied Biosystems (Foster City, Calif.), for example, AMPLITAQ GOLD™ DNA polymerase; AMPLITAQ™ DNA Polymerase; Stoffel fragment; rTth DNA Polymerase; and rTth DNA Polymerase XL. Other suitable polymerases that can be used include, but are not limited to, Tne, Bst DNA polymerase large fragment from *Bacillus stearothermophilus*, Vent and Vent Exo—from *Thermococcus litoralis*, Tina from *Thermotoga maritirna*, Deep Vent and Deep Vent Exo- and Pfu from *Pyrococcus*, and mutants, variants and derivatives of the foregoing. For further discussion of polymerases, and applicable molecular biology procedures generally, see, Ausubel et al., *Current Protocols in Molecular Biology*, John Wiley & Sons, New York, 2001, and The *Polymerase Chain Reaction*, Mullis, K. B., F. Ferre, and R. A. Gibbs, Eds., *Molecular Cloning: A Laboratory Manual*, (3rd ed.) Sambrook, J. & D. Russell, Eds. Cold Spring Harbor Laboratory Press, Cold Spring Harbor, N.Y. (2001), all of which are incorporated herein in their entireties by reference.

Amplification reaction times, temperatures, and cycle numbers can be varied to optimize a particular reaction. Addition of additives to reduce stutter and reduce non-specific amplification can also be used as determined appropriate by one of skill in the art, for example, see US Patent Application Publication 2005/0112591 to Dimoski et al., which is incorporated herein in its entirety by reference.

According to various embodiments, a DNA library can be prepared for analysis. Genomic libraries have been prepared by a variety of methods, for example, restriction digestion and ligation, mechanical fragmentation and enzymatic "tailing," and PCR amplification using primers, however, libraries other than genomic libraries can also be prepared. Methods of library preparation are known in the art, for example, in *Nucl. Acids Res.* 25:781-786 (1997), *Nucl. Acids Res.* 17:3645-3653 (1989), both of which are incorporated herein in their entireties by reference.

A library can be prepared enzymatically without first cloning DNA in bacteria. DNA can be digested or sheared into appropriate sized fragments, for example, fragments of about 50 bp, 100 bp, about 200 bp, about 500 bp, about 1000, or about 2000 bp. Sheared DNA can be filled in by 5' phosphorylation or polymerization using a Klenow fragment of DNA polymerase, for example, see Kinzler et al., *Nucleic Acids Res.* 17:3645-3653 (1989), incorporated herein by reference, and adapters can then be ligated to ends of sized fragments for attachment to an appropriate surface. An adapter can comprise a sequence of interest attached to a biotin moiety that has been ligated to a DNA fragment. The biotin moiety permits a DNA fragment to bind to a surface, for example, a bead or a capillary channel coated with streptavidin. Other binding methods can be used as well, for example, peptide nucleic acid, locked nucleic acid, and LDNA binding methods.

According to various embodiments, biotin-streptavidin can be a suitable choice for attaching a nucleic acid to a surface for generation of a nucleic acid library, as well as for amplification and sequencing reactions in a capillary channel, because a biotin-streptavidin linkage can withstand large and rapid temperature changes experienced in performing such reactions. Attachment by other than a biotin-streptavidin linker can also be used. Such linkers should also be able to withstand large and rapid temperature changes. If, however, an isothermal method is used, stability to large and rapid temperature changes may not be necessary.

If an oligonucleotide is to be attached to a substrate, the attachment can be done either batch-wise with a substance-coupled carrier slurried in a suitable medium, or on a column comprising an activated carrier. Any conventional carrier material (for example, Sepharose beads, (Pharmacia, Sweden)), filters, capillaries, or plastic dipsticks (for example, polystyrene strips), and microtitre wells to which the substance can be sufficiently coupled, can be used, depending on the application for which a nucleic acid is to be used.

Unfilled portions of a DNA fragment can be filled in and the complement can be displaced by denaturation. Fragments of interest can be collected and quantitated. A collected fragment can include, for example, variable regions of genomic DNA.

According to various embodiments, nucleic acids generated by a library, can be diluted by a limiting dilution procedure such that a concentration of a single molecule of interest per a given volume of liquid can be obtained. Nucleic acids obtained by any method can be diluted to a concentration of about one molecule per given volume prior to analysis. When a sample is diluted to this extent, some volumes may not have any nucleic acid molecules, while others can have more than 1 molecule. For example, in some embodiments, a plurality of volumes, can have a single molecule. In other embodiments, about 10% or less, about 20% or less, about 30% or less, or about 50% or less of the volumes can have a single molecule. One of skill in the art can appreciate how to prepare a solution by limiting dilution. After a sample is diluted by limiting dilution, a single nucleic acid molecule can be introduced into a capillary channel in an aqueous slug. Not all aqueous slugs formed from a nucleic acid solution theoretically diluted to one molecule per given volume will necessarily have a nucleic acid in every given volume. In various embodiments, about 10% or less, about 20% or less, about 30% or less, about 40% or less, about 50% or less, about 60% or less, about 70% or less, about 80% or less, about 90% or less, about 95% or less, or about 99% or less, of the aqueous slugs can have one nucleic acid molecule per given volume. In various embodiments, at least about 1% or more, about 5% or more, about 10% or more, or about 20% or more of the aqueous slugs can have one nucleic acid molecule per given volume.

According to various embodiments, a set of immiscible fluid discrete volumes of an aqueous liquid spaced-apart from one another by an immiscible spacing fluid can be prepared in a conduit. According to various embodiments, the conduit can comprise, for example, a capillary channel, a tube, a groove, or a channel formed by opposing barriers.

According to various embodiments, PCR can be performed in an aqueous discrete volume in a conduit to amplify a nucleic acid molecule, although other methods can be used to amplify the nucleic acid molecule, for example, reverse transcriptase PCR (RT-PCR) or a ligase chain reaction. During amplification, a terminal moiety comprising, for example, a caged biotin, can be incorporated into the nucleic acid being synthesized or amplified such that an amplified nucleic acid (amplicon) can be treated to attach the nucleic acid to an inner surface of a capillary channel. The terminal moiety can be incorporated through primer used in amplification. In some embodiments, the terminal moiety can be located at a position other than the 3' or 5' termini of the polynucleotide of interest provided that the moiety can be used to attach the amplicon to a solid support. According to various embodiments, a single DNA molecule can be attached first to an inner surface in a conduit and then amplified. In other embodiments, the DNA being amplified need not be attached to the inner surface of the conduit. Rather, the DNA is amplified in the discrete volume, either during movement through the conduit or when the conduit in maintained in a stationary position in or on a thermal cycling device. The amplified sample can be dispensed onto the electrically conductive substrate after amplification in the aqueous slugs.

The system can comprise a thermal cycling device. The thermal cycling device can, for example, be adapted to thermally cycle an aqueous sample or the electrically conductive substrate. The thermal cycling device can comprise a heat source, for example, a radiant or non-radiant heat source, and a cooling source, for example, a fan, an air jet, or a liquid-circulating system in a thermal block. The thermal cycling device can comprise one or more temperature sensors and one or more control units for controlling heating and cooling according to a desired thermal cycle. The thermal cycling device can be in direct contact with the sample or surface to be thermally controlled, but does not necessarily need to do so.

According to various embodiments, compartmentalized target nucleic acids can be amplified from an initial single copy to a number of copies suitable for downstream sequencing reactions. Amplification of DNA can be accomplished by a number of methods, including but not limited to, polymerase chain reaction, rolling circle amplification or multiple stand displacement. The amplified DNA can then be injected from an electrically conductive surface into a capillary channel.

The apparatus can be part of an integrated system and/or be adapted to function with other pieces of equipment adapted for further sample processing of samples, for example, an ABI 310, ABI 3130, ABI 3130xl, ABI 3700, ABI 3730, or ABI 3730xl capillary electrophoretic analyzer (available from Applied Biosystems, Foster City, Calif.) that can be used for sequencing. In some embodiments, the apparatus can be part of an integrated system and/or be adapted to function with other pieces of equipment adapted for further sample processing of samples, for example, a PCR detector. Exemplary detectors that can be used include real-time sequence detection systems and real-time PCR detectors, for example, the ABI 7900, available from Applied Biosystems, Foster City, Calif. In various embodiments, the apparatus provided can be used as a back-end sample deposition device.

The apparatus, system and/or methods described herein can also be used in conjunction with downstream processing of immiscible-fluid-discrete-volumes in conduits as described, for example, in FIGS. 10 and 11 of U.S. Provisional Patent Application No. 60/710,167 entitled "Sample Preparation for Sequencing" to Lee et al., filed Aug. 22, 2005, or U.S. Provisional Patent Application No. 60/731,133 entitled "Method and System for Spot Loading a Sample" to Schroeder et al., filed Oct. 28, 2005 which applications are incorporated herein in their entireties by reference. If there is any discrepancy between the description of immiscible-fluid-discrete-volumes in an immiscible fluid in the above provisional applications and this one, this application is deemed to be correct.

While the present teachings primarily relate to processing a discrete volume after it has been generated and processed, an entire system and method is provided, according to various embodiments, that comprises either or both of generating and processing an immiscible-fluid-discrete-volume. An exemplary system and method is described and shown in connection with FIGS. 1A and 1B herein.

Figure 1A:
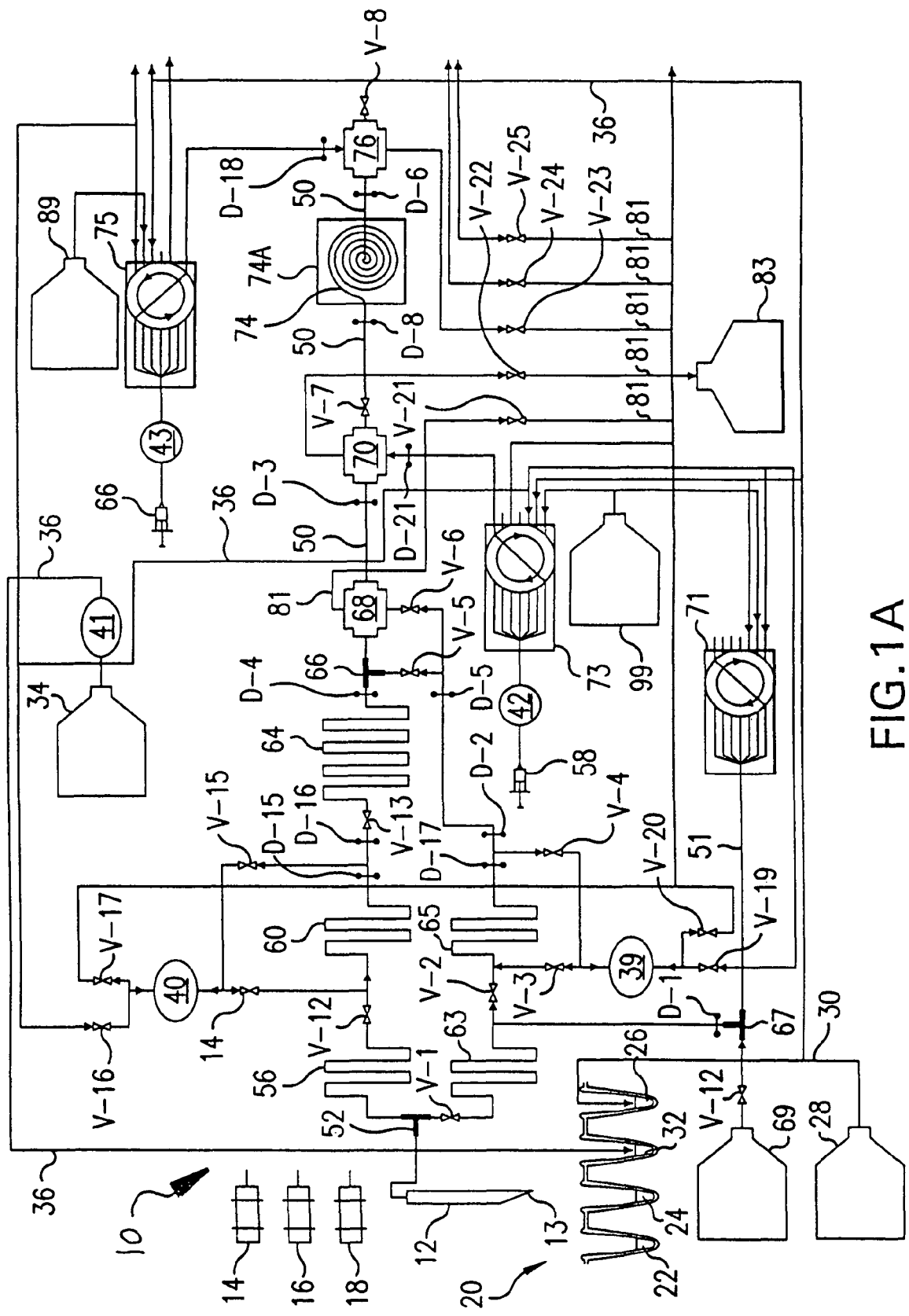
FIGS. 1A and 1B are the left-side and right-side, respectively, of a schematic diagram depicting a system according to various embodiments of the present teachings and configured to generate immiscible-fluid-discrete-volumes of a first fluid spaced apart from one another by a spacing fluid, to process the immiscible-fluid-discrete-volumes, and to output the immiscible-fluid-discrete-volumes.
Figure 1B:
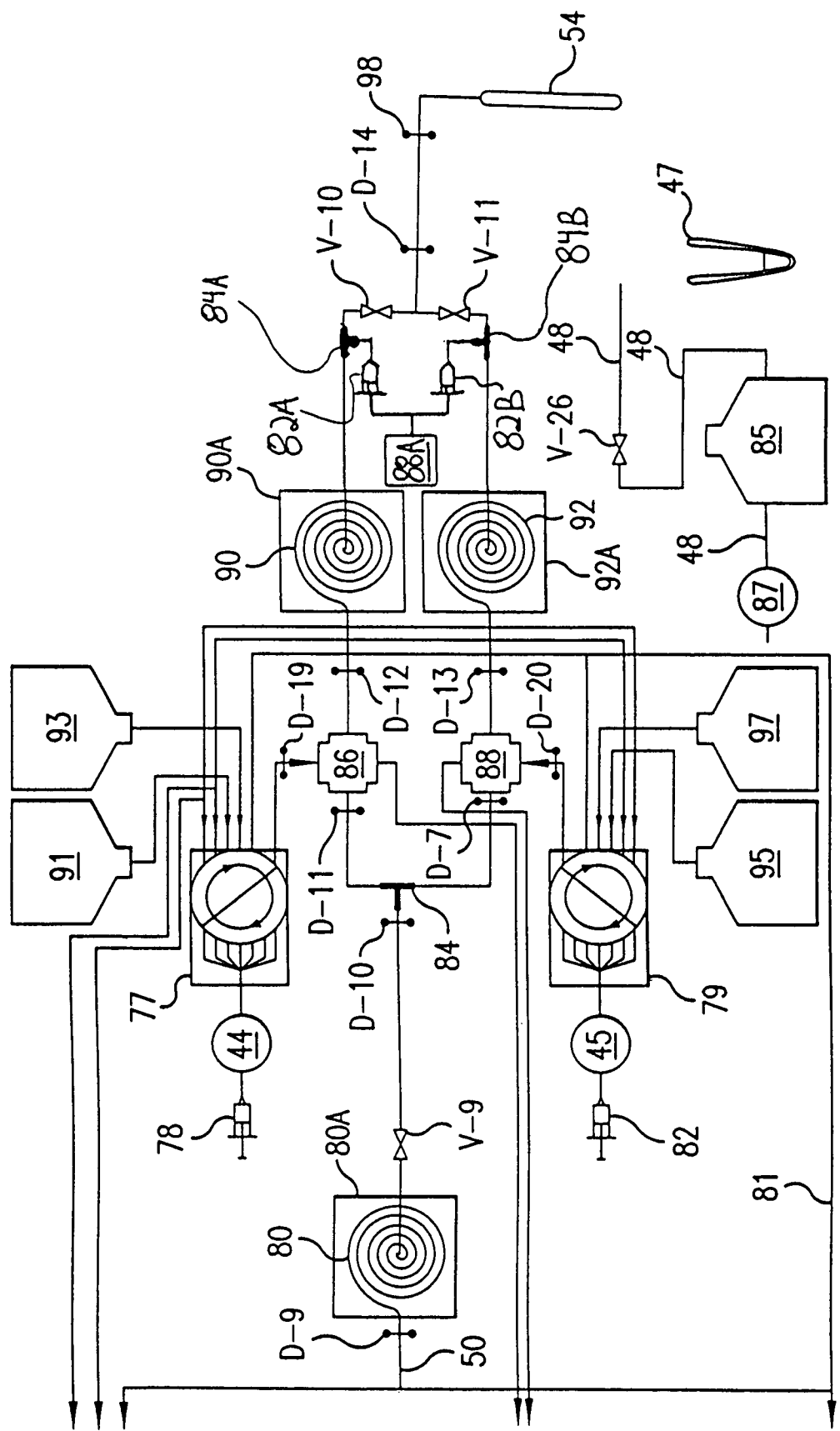

FIGS. 1A and 1B are the left-side and right-side, respectively, of a schematic diagram detailing an example of a fluid processing system 10 for processing fluid immiscible-fluid-discrete-volumes. The six conduits on the right-hand side of FIG. 1A and terminating in arrow heads pointing to the right are respectively continued as the six conduits shown on the left-hand side of FIG. 1B and terminating in arrow heads pointing to the left, such that the top conduit of each respective six depicted are continuations of each other, and so on going down the figures.

Generally, system 10 can be configured to perform different types of assays on fluids introduced thereinto. The amounts and types of fluids introduced into system 10 can be varied depending on a particular assay to be performed. Exemplary assays can include, for example, de novo nucleic acid sequencing reactions, and nucleic acid resequencing reactions, as discussed herein. An exemplary type of sample preparation can be used for genotyping, gene-expression, methylation analysis, and/or directed medical sequencing (VARIANTSEOR™, for example, an Applied Biosystems product comprising primers for resequencing genes and detecting variations) that requires multiple liquids to be brought together in an aqueous discrete volume. For example, in a gene-expression application, each aqueous discrete volume can contain individual primer sets. The sample to be analyzed, for example, complementary DNA (cDNA), can be added to each aqueous discrete volume. In the VARIANT-SEQR™ application, for example, an aqueous discrete volume can comprise a primer set, and genomic DNA can be added to that discrete volume.

According to various embodiments, one or more sample fluids 22, 24, can be introduced to system 10. Sample fluids 22 and 24, for example, can comprise a nucleic-acid-containing fluid. According to some embodiments, the nucleic acid contained in a sample fluid can be, for example, a single copy of a genomic DNA sequence of an organism, or complementary DNA from an organism.

In some embodiments, a plurality of fluids can be introduced into fluid processing system 10 by way of an immiscible-fluid-discrete-volume-forming conduit 12, which is a part of main conduit system 50. Suitable immiscible-fluid-discrete-volume-forming conduits include, for example, pipettes, capillaries, electro-wetting capillaries, needles, and any device configured to be in fluid communication with fluid processing system 10. Immiscible-fluid-discrete-volume-forming conduit 12 can be part of a system that can comprise, for example, a pump or another apparatus adapted to produce controlled intake of fluids through intake tip 13 into immiscible-fluid-discrete-volume-forming conduit 12. The immiscible-fluid-discrete-volume-forming conduit 12 can be adapted to control an introduction unit to introduce alternate volumes of aqueous sample fluid and spacing fluid that together form discrete volumes of aqueous sample fluid in contact with spacing fluid, i.e., aqueous sample immiscible-fluid-discrete-volumes, in the at least one conduit wherein each aqueous sample immiscible-fluid-discrete-volume can comprise a maximum outer dimension that is equal to or slightly less than the maximum inner cross-sectional dimension of immiscible-fluid-discrete-volume-forming conduit 12. One of skill in the art will understand that the maximum inner cross-sectional dimension of a conduit is the inner diameter of the conduit if the conduit has a circular cross-section.

According to various embodiments, immiscible-fluid-discrete-volume-forming conduit 12 can comprise a tip 13. Tip 13 can interface with fluids to be drawn into system 10. Tip 13 can comprise an angled surface or have any suitable geometry such that the creation of air bubbles in immiscible-fluid-discrete-volume-forming conduit 12 is minimized or eliminated when tip 13 contacts and draws in a fluid. A detailed description of tip 13 can be found below in the description of FIG. 13. Immiscible-fluid-discrete-volume-forming conduit 12 can be robotically controlled, or manually controlled. Robotic configurations can comprise, for example, stepper motors 14, 16, and 18, which can move immiscible-fluid-discrete-volume-forming conduit 12 in X-axis, Y-axis, and Z-axis directions, respectively. In some embodiments, tube 12 can be moved in the Z-axis direction by a stepper motor 18, and a fluid container can be moved in the X-axis and Y-axis directions by stepper motors 14 and 16, respectively. In some embodiments, tube 12 can be stationary and a fluid container can be moved in the X-axis, Y-axis, and Z-axis directions by stepper motors 14, 16, and 19, respectively. Motive force providers other than stepper motors can be used.

According to various embodiments, a variety of fluids can be introduced into fluid processing system 10, in a number of different combinations, depending on the particular type of assay to be performed. The fluids can reside on any suitable fluid retaining device, for example, in the wells of a multi-well plate 20, an opto-electrowetting plate, a tube of pre-formed slugs, a tube of stable emulsified nanodroplets, individual tubes, strips of tubes, vials, flexible bags, and the like.

According to some embodiments, fluid processing system 10 can comprise a number of different fluid conduits and fluid control devices. The following description applies to the embodiment as illustrated in FIGS. 1A and 1B, but one skilled in the art will understand that alterations to fluid processing system 10 can be made while the teachings remain within the scope of the present teachings. As illustrated, fluid processing system 10 can comprise a main system conduit 50. Main conduit system 50 can comprise a plurality of conduits each in fluid communication with, for example, the following exemplary components: T-junctions 52, 66, and 84; holding conduits 56, 60, 63, 64 and 65; valves V-1, V-2, V-5, V-6, V-7, V-8, V-9, V-10, V-11, V-12, and V-13; cross-junctions 68, 70, 76, 86, and 88; and thermal spirals 74, 80, 90, and 92. Along conduit 50, thermal spirals 74, 80, 90, and 92 can be in thermal contact with respective thermal cyclers 74A, 80A, 90A, and 92A Each thermal cycler 74A, 80A, 90A, and 92A can independently comprise a liquid bath, an oven, a plate, a block comprising fluid passages therein, a peltier device, or the like thermal cycling device.

Main conduit system 50 can provide a fluid communication between T-junction 52 and output conduit 54. From T-junction 52, conduit system 50 comprises two pathways that join at cross-junction 68. A first pathway can take a fluid sequentially through holding conduits 56, 60 and 64, and T-junction 66, before reaching cross-junction 68. A second pathway can take a fluid sequentially through holding conduits 50, and 65, and through either T-junction 66, to cross-junction 68, or directly to cross-junction 68. Both the first pathway and the second pathways are configured to hold fluids for later analysis and are configured to interface with devices for moving fluids along the conduits as discussed below.

From cross-junction 70, fluids can move sequentially to thermal spiral 74, cross-junction 76, thermal spiral 80, and T-junction 84. At T-junction 84 fluids can sequentially move either through cross-junction 86, thermal spiral 90, and output conduit 54, or through cross-junction 88, thermal spiral 92, and an output conduit.

According to some embodiments, fluid processing system 10 can comprise pumps 39 and 40. Pump 40 can be configured to remove or add oil to main conduit system 50, and thereby move fluids located therein. Pump 39 can be configured to remove or add oil to main conduit system 50 to move fluids located therein. All of the pumps described herein can create positive and/or negative pressures in the various conduits of system 10.

According to various embodiments, a T-junction can comprise any junction having three discrete pathways extending from, for example, either a Y-junction or a T-junction. In various embodiments, the junction can comprise a valve-less junction where a stream of aqueous sample fluid and a stream of non-aqueous spacing fluid can meet and form at least discrete volumes of the aqueous sample fluid in contact with the non-aqueous spacing fluid. For example, microfabrication technology and the application of electrokinetics or magnetohydrodyamics can achieve fluid pumping in valve-less, electronically controlled systems. Components comprising shape-optimized conduit turns, optimal introduction methods, micromixers, and/or high flow rate electroosmotic pumps can be used in such a valve-less system.

According to some embodiments, system 10 can comprise discrete volume detectors D-1, D-2, D-3, D-4, D-5, D-6, D-7, D-8, D-9, D-10, D-11, D-12, D-13, D-14, D-15, D-16, D-17, D-18, D-19, and D-20, and detector 98. The discrete volume detectors can comprise, for example, fluorescent detectors, infra-red detectors, capacitive detectors, absorption detectors, refractive-index detectors, combinations thereof, and the like. In FIGS. 1A and 1B, all of the detectors depicted are infra-red, refractive-index detectors with the exception of detector 98 which is a fluorescent signal detector, although other arrangements can be used. The discrete volume detectors can be configured to distinguish immiscible-fluid, discrete volumes from spacing fluid or oil as the discrete volumes travel through the conduits of system 10.

According to various embodiments, the system can comprise a thermal-cycling device or thermal cycler, adapted to thermally cycle an aqueous immiscible-fluid, discrete volume in a conduit disposed thereon or therein. In some embodiments, the conduit can contact the thermal cycler in a single straight-line segment, or a coil around the external perimeter of thermal cycler, or a spiral of decreasing radius on one surface, or a serpentine pattern across one or more surfaces of thermal cycler. The thermal-cycling device can comprise a heat source, for example, a radiant heat source, a non-radiant heat source, a peltier device, or the like, and a cooling source, for example, a fan, an air jet, or a liquid-circulating system in a thermal block. The thermal-cycling device can comprise one or more temperature sensors and one or more control units for controlling heating and cooling according to a desired or programmed thermal cycle.

In some embodiments, the conduits of the present teachings can comprise capillary tubes having an inner diameter and the inner diameter can be, for example, about 1000 microns or less, for example, about 800 microns or less, or about 500 microns or less. In some embodiments, the conduit has a minimum inner dimension, or diameter, of from about 1.0 micron to about 100 microns, or from about 50 microns to about 75 microns. In other embodiments, the conduit can have an inner diameter greater than about 300 microns. In some embodiments, the conduit can comprise an inner diameter in the range of from about 0.015 inch to about 0.025 inch, for example, from about 0.019 inch to about 0.025 inch. In some embodiments, the conduit can have a smaller diameter at and/or beginning before a pair of thermal spirals near the downstream end of the system which are designed for forward/reverse sequencing amplification. Other details about the thermal-cycling device, capillary channel or conduit, and other system components will become apparent in view of the teachings herein.

System 10 can comprise a single molecule amplification fluid ("SMAF") conduit system 51. SMAF tube system 51 can supply sample fluid to a T-junction through positive pressure rather than by aspiration. SMAF conduit system 51 can comprise a supply conduit connected to and in fluid communication with a supply of single molecule amplification fluid. The SMAF can comprise a solution or mixture of target nucleic acids diluted to a degree such that there is an average of less than about one target nucleic acid per volume of single molecule amplification fluid that is used to make an immiscible-fluid-discrete-volume. An exemplary concentration of target molecules can be 0.4 molecule per volume used to make an immiscible-fluid-discrete-volume. SMAF conduit system 51 can comprise conduits connecting a SMAF reservoir 69 sequentially to valve V-18 and T-junction 67. SAMF conduit system 51 can comprise conduits that connect T-junction 67 to main conduit system 50 and a rotary valve 71.

Fluid processing system 10 can comprise rotary valves 71, 73, 75, 77, and 79. Each rotary valve can function to direct the flow of metered amounts of different reagents from different respective reagent reservoirs connected thereto, as described below, to main conduit system 50. Syringe pumps 58, 66, 78, and 82 can be in fluid communication with rotary valves 73, 75, 77, and 79, respectively. Pumps 42, 43, 44, and 45 can be in fluid communication with rotary valves 73, 75, 77, and 79, respectively.

Fluid processing system 10 can comprise a first waste conduit system 81. Waste conduit system 81 can comprise conduits connecting the following components: valves V-17, V-20, V-21, V-22, V-23, V-24, V-25, and a waste reservoir 83. Waste conduit system 81 can provide a fluid communication between and cross-junctions 68, 70, 76, 86, and 88 and waste reservoir 83.

Fluid processing system 10 can comprise a second waste conduit system 48. Second waste conduit system 48 can comprise conduits connecting a pump 87, a waste reservoir 85, and a valve V-26, that interface with output conduit 54. Second waste conduit system 48 can be used to remove liquids from output conduit 54.

Fluid processing system 10 can comprise reagent reservoirs 89, 91, 93, 95, 97, and 99 and can be in fluid communication with rotary valves 75, 77, 77, 79, 79, and 73, respectively. Reagent reservoir 89 can contain, for example, an exo-nuclease and shrimp alkaline phosphatase. Reagent reservoir 91 can contain, for example, nucleic acid amplification reaction forward primers. Reagent reservoir 93 can contain, for example, nucleic acid amplification reaction chain terminating dyes. Reagent reservoir 95 can contain, for example, nucleic acid amplification reaction reverse primers. Reagent reservoir 97 can contain, for example, nucleic acid amplification reaction chain terminating dyes. Reagent reservoir 99 can contain, for example, a nucleic acid amplification reaction master mix comprising, for example, reactive single base nucleotides, buffer, a polymerase, and the like, for example, to carry out a polymerase chain reaction.

According to various embodiments, fluid processing system 10 can comprise a rinse conduit system 30. Rinse conduit system 30 can provide a fluid communication between a rinse fluid reservoir 28, rotary valve 73, rotary valve 75, and immiscible-fluid-discrete-volume-forming conduit 12. Rinse fluid reservoir 28 can contain a rinse fluid 26. Rinse fluid 26 can comprise microbiologic grade water, for example, distilled, de-ionized water.

Rinse fluid 26 can be used to remove residual sample, for example, from immiscible-fluid-discrete-volume-forming conduit 12. Rinse fluid can be provided to multi-well plate 20, by way of rinse conduit system 30. Rinse fluid 26 can be used as a rinse at the input station, and/or can be used as a rinse fluid, a dilution fluid, or both, elsewhere in the system. In some embodiments, rinse fluid 26 can be added to immiscible-fluid, discrete volumes to adjust the volume or concentration thereof, in conjunction with an addition station, as described in FIG. 1C.

According to various embodiments, fluid processing system 10 can comprise a spacing fluid conduit system 36. Spacing fluid conduit system 36 can provide a fluid communication between a spacing fluid reservoir 34, vacuum pump 41, and multi-well plate 20. Spacing fluid reservoir 34 can contain an oil 32 or other spacing fluid that is immiscible with an immiscible-fluid-discrete-volume-forming fluid, for example, an aqueous slug fluid.

In some embodiments, the spacing fluid can be non-aqueous. The spacing fluid can comprise an organic phase, for example, a polydimethylsiloxane oil, a mineral oil (e.g., a light white mineral oil), a silicon oil, a hydrocarbon oil (e.g., decane), a fluorinated fluid or a combination thereof.

Fluorinated compounds such as, for example, perfluorooctyl bromide, perfluorodecalin, perfluoro-1,2-dimethylcyclohexane, FC 87, FC 72, FC 84, FC 77, FC 3255, FC 3283, FC 40, FC 43, FC 70, FC 5312 (all "FC" compounds are available from 3M, St. Paul, Minn.), the NOVEC® line of HFE compounds (also available from 3M, St. Paul, Minn.), such as, for example, HFE-7000, HFE-7100, HFE-7200, HFE-7500, and perfluorooctylethane can also be used as the spacing fluid. Combinations, mixtures, and solutions of the above materials can also be used as the spacing fluid.

In some embodiments, fluorinated alcohols, such as, for example, 1H, 1H, 2H, 2H-perfluoro-decan-1-ol, 1H, 1H, 2H, 2H-perfluoro-octan-1-ol, and 1H, 1H-perfluoro-1-nonanol can be added to a fluorinated compound, such as those listed above, to improve the stability of aqueous discrete volumes within the spacing fluid, but still maintain the ability to coalesce upon contact. In some embodiments, fluorinated alcohols can be added in a range of approximately 0.1% to approximately 5% by weight. In some embodiments, the fluorinated alcohol additive can be approximately 0.1%, 0.2%, 0.5%, 1.0%, 1.5%, 2.0%, 3.0%, 4.0% or 5% by weight of the fluorinated compound. In some embodiments, the fluorinated alcohol additive can be from approximately 1% to approximately 10% by volume of the fluorinated compound. In some embodiments, the fluorinated alcohol additive may comprise approximately 1%, 2%, 3%, 4%, 5%, 6%, 7%, 8%, 9%, or 10% by volume of the spacing fluid. In some embodiments, F-alkyl dimorpholinophosphates can be added as surfactants to fluorinated compounds.

In some embodiments, the organic phase can include non ionic surfactants such as sorbitan monooleate (SPAN 80 (no. S-6760, Sigma)), polyoxyethylenesorbitan monooleate (TWEEN 80 (no. S-8074, Sigma)), sorbitan monostearate (SPAN 60), octylphenoxyethoxyethanol (TRITON X-100 (no. T9284, Sigma)). In some embodiments, SPAN 80 can be added in an amount ranging from about 1.0% to about 5.0%, or about 3.0% to about 4.5%. In some embodiments, adding surfactants in the quantities of 4.5% SPAN 80, 0.40% TWEEN 80, and 0.05% TRITON X-100 to mineral (no. M-3516, Sigma) can result in the creation of stable emulsified droplets.

In some embodiments, the organic phase can include ionic surfactants, such as sodium deoxycholate, sodium cholate, and sodium taurocholate. In some embodiments, the organic phase can include chemically inert silicone-based surfactants, such as, for example, polysiloxane-polycetyl-polyethylene glycol copolymer. In some embodiments, the non-aqueous, spacing fluid can have a viscosity between approximately 0.5 to approximately 0.75 centistokes. In some embodiments, the non-aqueous spacing fluid can have a viscosity between approximately 0.75 centistokes to about 2.0 centistokes. In some embodiments, the non-aqueous spacing fluid can have a viscosity greater than 2.0 centistokes. In some embodiments, the non-aqueous spacing fluid can have a viscosity between 0.5 to greater than about 2.0 centistokes. In some embodiments, the non-aqueous spacing fluid can have a viscosity greater than 2.0 centistokes. In some embodiments, the non-aqueous, spacing fluid can have a boiling point greater than or equal to 100° C.

Spacing fluid 32 can function to separate discrete volumes of an immiscible-fluid-discrete-volume-forming fluid, for example, and aqueous sample, before, during, or after the immiscible-fluid-discrete-volume-forming fluid has been introduced into system 10. Spacing fluid can be provided to multi-well plate 20, from a spacing fluid reservoir 34, by way of a spacing fluid conduit system 36.

According to some embodiments, a de novo nucleic acid sequencing method is provided that uses system 10. The de novo sequencing method can be used to sequence an entire genome or portions thereof. The de novo sequencing method can be especially useful when the sequence of the organism is unknown.

In some embodiments, a de novo sequencing method comprises pre-processing a sample, separating the sample into a set of immiscible-fluid, discrete volumes, optionally adding amplification reagents to each discrete volume of the set, amplifying nucleic acids in the set of immiscible-fluid, discrete volumes to form a set of amplified immiscible-fluid, discrete volumes, optionally detecting, and removing, discrete volumes without amplified sample molecules therein, adding primer and dNTP deactivation agents to each discrete volume in the set, or optionally, to only those with amplified sample molecules, incubating the set of amplified immiscible-fluid, discrete volumes with primer and dNTP deactivation agents, subjecting the resulting nucleic acids to sequencing conditions to form detectable products, and detecting the detectable products.

In some embodiments, the method can comprise pre-processing a sample before the sample fluid is introduced into system 10. The pre-processing of a sample can comprise fragmenting the nucleic acid present in the sample fluid. The fragmentation can be accomplished by any suitable method known in the art. For example, the nucleic acid can be fragmented by enzymatic digestion, or physical disruption methods, for example, hydro-sheering or sonication. In some embodiments the nucleic acid can be fragmented to an average size of about 500 B, 750 B, 850 B, 1 KB, 2 KB, or 3 KB, for example.

According to some embodiments, the pre-processing of sample can comprise ligating sequences to a sample. Universal sequences can be used to facilitate universal nucleic acid amplification. Universal sequences can be artificial sequences that generally have no homology with the target nucleic acids. Universal sequences can be designed to resist the formation of dimers between themselves. Universal sequences can be designed to bind with analogous primers with a consistent efficiency.

According to some embodiments, the present teachings can encompass a de novo sequencing method wherein universal sequences can be ligated to the 5' and 3' ends of the DNA fragments in a sample by, for example, T4 DNA ligase, thereby forming a universal tail. The universal tail sequences can function as sites of complementarity for zip code primers. Details of universal tail procedures can be found in U.S. Pat. App. No. 2004/0185484, to Costa et al., which is incorporated herein, in its entirety, by reference.

According to various embodiments, the amplifying of a nucleic acid can comprise a thermal cycling nucleic acid sequence amplification process or an isothermal nucleic acid sequence amplification process. If a thermal cycling nucleic acid sequence amplification process is used, the process can comprise, for example, a polymerase chain reaction (PCR). The nucleic acid sequence amplification reaction can comprise an exponential amplification process, for example, PCR, or a linear amplification process, as can occur during, for example, during Sanger cycle sequencing. In various embodiments, other nucleic acid amplification processes can be used, for example, ligase chain reaction (LCR), nucleic acid sequence based amplification (NASBA), Q-beta replicase (QB) amplification, or strand displacement amplification (SDA). These alternatives, as well as others known to one skilled in the art, can be used either by themselves or in combination with PCR to amplify nucleic acids.

According to various embodiments, nucleic acid sequence processing methods comprising a first type of nucleic acid amplification reaction followed by one or more of a second different type of amplification reaction, and/or detection assay reaction, can be carried out, for example, as described in U.S. Patent Application No. 60/699,782 to Faulstich et al., filed Jul. 15, 2005, and in U.S. Patent Application Publication No. 2007/0026439 A1, which are incorporated herein in their entireties by reference.

According to some embodiments, the present teaching can comprise a method of de novo sequencing wherein pre-processing of sample can comprise adding zip code primers to a sample of nucleic acid having universal tail sequences ligated therein. Zip code primers can be complementary to the universal tail sequences. The use of zip code tails sequences and zip code primers can reduce the need for target specific primers, resulting in significant cost savings as well as greater assay flexibility.

According to various embodiments, pre-processing a sample can comprise adding to the sample reactants to facilitate a nucleic acid amplification reaction. For example, the four dNTP's (dATP, dTTP, dGTP, and dCTP), a polymerase, oligonucleotide primers, and/or chelating agents can be added to the sample. Oligonucleotide primers can be chosen as determined by one of skill in the art to accomplish the desired objective, for example, universal primers can be used.

According to various embodiments, pre-processing a sample can comprise diluting the sample with a miscible solvent, vehicle, or carrier. The sample can be diluted at a ratio of 1:1, 1:10, 1:100, 1:1000, or 1:10,000, for example. Exemplary ranges of dilution can be from about 1:1 to about 1:100, or from about 1:10 to about 1:50. For example, the sample can be diluted such that only a single fragment of nucleic acid is present per 500 nanoliters of diluted sample, or per 200 nanoliters of diluted sample. In some embodiments, the concentration of target fragments can be based on the size of the immiscible-fluid-discrete-volumes generated that carry the target fragments, such that an average of about 1 target fragment is present per 1.4 immiscible-fluid-discrete-volumes generated. According to various embodiments, the sample can be diluted such that at least 50% immiscible-fluid-discrete-volumes produced from a sample in the process described below can each comprise a single target nucleic acid sequence. In various other embodiments, less than about 50% of the immiscible-fluid-discrete-volumes produced can each comprise a single target nucleic acid sequence. In other embodiments, at least 1% or more, 5% or more, 10% or more, or 20% or more can comprise a single target nucleic acid sequence, for example, from about 10% to about 50% or from about 20% to about 40%.

After optional preprocessing, the sample fluid is introduced to system 10 to form one or more discrete volumes of the sample fluid in a spacing fluid with which it is immiscible. According to various embodiments, the method can comprise forming immiscible-fluid-discrete-volumes of discrete amounts of sample fluid and/or reagents inside conduit system 50. A plurality of immiscible-fluid-discrete-volumes can be associated together as a set of immiscible-fluid-discrete-volumes. Each set of immiscible-fluid-discrete-volumes can comprise immiscible-fluid-discrete-volumes separated from one another by a spacing fluid, for example, an oil. Each immiscible-fluid-discrete-volume of a set can be equally spaced from one or more adjacent immiscible-fluid-discrete-volumes of the set. Multiple sets of immiscible-fluid-discrete-volumes can be present at the same time in main conduit 50. Each set of immiscible-fluid-discrete-volumes can be separated from one or more other sets of immiscible-fluid-discrete-volumes by spacing fluid. In some embodiments, two or more sets of immiscible-fluid-discrete-volumes are spaced from one another a distance that is greater than the average distance between adjacent immiscible-fluid-discrete-volumes with the same set.

In the embodiment depicted in FIGS. 1A and 1B, immiscible-fluid-discrete-volumes that have been aspirated into immiscible-fluid-discrete-volume-forming conduit 12 can be moved into holding conduit 56 by suction produced by vacuum pump 40.

According to various embodiments, a sample to be subjected to de novo sequencing can comprise a single copy of the genomic DNA of an organism. The sample DNA can be sheared, and universal tails can be ligated to the sample. Nucleic acid amplification reactants can be added to the sample before the sample is drawn into system 10 or after the sample has been drawn into system 10. The nucleic acid amplification reactants can comprise universal primers, for example, primers that are specific to the universal tail sections ligated to the sample nucleic acid fragments. The sample can be diluted such that when the sample is made into immiscible-fluid-discrete-volumes by system 10, each immiscible-fluid-discrete-volume does not contain more than one nucleic acid fragment. For example, 1, 2, 3, 4, or 5 out of ten immiscible-fluid-discrete-volumes can contain nucleic acid fragments.

According to some embodiments, the method can comprise moving a set of immiscible-fluid-discrete-volumes, from T-junction 52, to cross-junction 70, by way of conduit system 50. If a set of immiscible-fluid-discrete-volumes does not contain nucleic acid amplification reactants, the reactants can be added to each immiscible-fluid-discrete-volume of the set of immiscible-fluid-discrete-volumes at cross-junction 70. Reactant addition to each immiscible-fluid-discrete-volume can be metered by rotary valves 71 and 73. Detector D-3 can detect the arrival of the beginning and/or the end of a set of sample immiscible-fluid-discrete-volumes at cross-junction 70. Detector D-21 can detect the arrival of the beginning and/or the end of immiscible-fluid-discrete-volumes at cross-junction 70. Valve V-7 can control the movement of a set of immiscible-fluid-discrete-volumes out of cross-junction 70.

According to some embodiments, the method can comprise moving a set of immiscible-fluid-discrete-volumes from cross-junction 70, through main conduit system 50, to thermal spiral 74. Detector D-8 can be used to detect the arrival of a set of immiscible-fluid-discrete-volumes at thermal spiral 74. Detector D-8 can be used to detect the end of a set of immiscible-fluid-discrete-volumes, and thereby detect that a set of immiscible-fluid-discrete-volumes is disposed in thermal spiral 74. A set of immiscible-fluid-discrete-volumes can be thermally cycled, for one or more cycles, for example, for from about 5 to about 50 temperature cycles or from about 20 to about 30 temperature cycles.

According to various embodiments, the method can comprise introducing polymerase chain reaction inactivating reagents into main conduit 50 after amplifying the at least one target nucleic acid sequence and before subjecting the nucleic acid sequence to a sequencing reaction. The reagents can be used to inactivate or remove or eliminate excess primers and/or dNTP's. The inactivating reagents can be introduced at an junction in the conduit, for example, after an immiscible-fluid-discrete-volume to be inactivated is aligned with the junction. The junction can comprise, for example, a T-junction.

According to some embodiments the method can comprise moving a set of immiscible-fluid-discrete-volumes from thermal spiral 74, through cross-junction 76. As the set of immiscible-fluid-discrete-volumes moves through cross-junction 76, the method can comprise adding exonuclease and shrimp alkaline phosphatase to each immiscible-fluid-discrete-volume of the set of immiscible-fluid-discrete-volumes. For example, the exonuclease and shrimp alkaline phosphatase can be metered out in discrete volumes which merge respectively with the immiscible-fluid-discrete-volumes of a set of immiscible-fluid-discrete-volumes at an junction in rotary valve 77. For example, exonuclease and shrimp alkaline phosphatase can be added to each immiscible-fluid-discrete-volume of the set of immiscible-fluid-discrete-volumes in cross-junction 76.

In the exemplary system shown, detector D-6 can detect the arrival of the beginning and/or the end of a set of sample discrete volumes at cross-junction 76. Detector D-18 can detect the arrival of the beginning and/or the end of one or more immiscible-fluid-discrete-volumes of exonuclease and shrimp alkaline phosphatase at cross-junction 76. Valve V-8 can control the movement of a set of immiscible-fluid-discrete-volumes out of cross-junction 76.

In the exemplary embodiment shown, a set of immiscible-fluid-discrete-volumes containing exonuclease and shrimp alkaline phosphatase can be moved into thermal spiral 80, via main conduit system 50. Detector D-9 can detect the arrival of the beginning and/or the end of a set of immiscible-fluid-discrete-volumes at thermal spiral 80. The set of immiscible-fluid-discrete-volumes can be incubated at from about 25° C. to about 35° C. for a time period of from about one minute, to about 60 minutes or from about two minutes to about 10 minutes. The incubation step can function to facilitate the activities of the exonuclease and shrimp alkaline phosphatase. A set of immiscible-fluid-discrete-volumes can be further incubated at a temperature of from about 75° C. to about 85° C., for a time period of from about 10 seconds to about 10 minutes, or from about one minute to about five minutes. The incubation at from about 75° C. to about 85° C. can function to heat-kill any enzymes that might still be present in the set of immiscible-fluid-discrete-volumes. After such incubation, processed immiscible-fluid-discrete-volumes can be maintained in a conduit section held at a lower temperature, for example, at about 25° C., in a stretch of conduit if it is desired to delay delivery of the immiscible-fluid-discrete-volumes to the cycle sequencing section of the system. In such circumstances a delay can be built into the system so that a first set of immiscible-fluid-discrete-volumes can be completely cycle sequenced while a second batch awaits movement into the cycle sequencing section of the system.

According to some embodiments, the method can comprise moving a set of immiscible-fluid-discrete-volumes to T-junction 84. Valve V-9 can control the movement of a set of immiscible-fluid-discrete-volumes from thermal spiral 80, to T-junction 84. Detector D-10 can detect the arrival of the beginning and/or the end of a set of immiscible-fluid-discrete-volumes at T-junction 84. The method can comprise dividing one or more immiscible-fluid, discrete volumes of a set of immiscible-fluid discrete volumes into two or more smaller immiscible-fluid-discrete volumes to form two newly formed sets of equal number of immiscible-fluid discrete volumes, but containing immiscible-fluid discrete volumes of smaller volume. The method can comprise moving one newly created set of immiscible-fluid, discrete volumes along main conduit system 50, to cross-intersection 86. Forward primers and chain terminating dyes can be moved from reservoirs 91 and 93, to rotary valve 77. The forward primers and chain terminating dyes can be metered out by rotary valve 77. The forward primers and chain terminating dyes can be moved to cross-intersection 86 and be added to each immiscible-fluid-discrete-volume of the newly-created set of immiscible-fluid, discrete volumes, thereby creating a forward set of immiscible-fluid, discrete volumes. According to various embodiments, the method can comprise moving the second newly created set of immiscible-fluid, discrete volumes along main conduit system 50, to cross-intersection 88. Reverse primers and chain terminating dyes can be moved from reservoirs 95 and 97, to rotary valve 79. The reverse primers and chain terminating dyes can be metered out by rotary valve 79. The reverse primers and chain terminating dyes reagent can be moved to cross-intersection 86 and be joined with each immiscible-fluid-discrete-volume of the second newly-created set of immiscible-fluid, discrete volumes, thereby creating a reverse set of immiscible-fluid, discrete volumes.

In some embodiments, the method can comprise moving the forward set of immiscible-fluid-discrete-volumes from cross-junction 86, along main conduit system 50, to thermal spiral 90. The forward set of immiscible-fluid-discrete-volumes can be thermally cycled for from about 5 to about 50, temperature cycles, for example, from about 20 to about 40 thermal cycles.

In some embodiments, the method can comprise moving the reverse set of immiscible-fluid-discrete-volumes from cross-junction 88, along main conduit system 50, to thermal spiral 92. The reverse set of immiscible-fluid-discrete-volumes can be thermally cycled for from about 5 to about 50 thermal cycles, for example, from about 20 to about 40 cycles, temperature cycles.

According to various embodiments, the method can comprise moving the forward and the reverse sets of immiscible-fluid-discrete-volumes from their respective thermal spiral to output conduit 54. Movement can be caused by syringe pumps 82A and 82B that can be controlled independently, or together, by a motor 88A operatively connected thereto. Syringe pumps 82A and 82B can push and pull fluids through respective T-junctions 84A and 84B. This arrangement is useful as syringe pumps 82A and 82B can initially pull immiscible-fluid-discrete-volumes into place in the respective thermal spirals 90 and 92, in conjunction with the positive pressure from the pumps on the upstream side of tee 84. Valves V-10 and V-11 can be switched so that immiscible-fluid-discrete-volumes can be pushed out of system 10. In some embodiments, the pushing can be done with one of pumps 82A and 82B at a time; therefore, there is no need to merge two separate sets of immiscible-fluid-discrete-volumes back together into a single set, but rather the separate sets can be individually dispensed. Output conduit 54 can deposit both sets of immiscible-fluid-discrete-volumes on, for example, a multi-well plate.

According to some embodiments, a dye can be added to one or more immiscible-fluid-discrete-volumes of a set of immiscible-fluid-discrete-volumes. The dye can comprise a double-strand (ds), nucleic acid intercalating dye, for example, SYBR green, SYBR gold, EVA green, LC green, or the like. The dye can be added to an aqueous immiscible-fluid-discrete-volume-forming fluid, such as an aqueous sample, before it is added to system 10. The dye can be added to a set of immiscible-fluid-discrete-volumes at any cross-junction of system 10. The dye can be used to discriminate between immiscible-fluid-discrete-volumes that contain ds nucleic acids and immiscible-fluid-discrete-volumes that do not contain ds nucleic acids. The immiscible-fluid-discrete-volumes that do not contain ds nucleic acids can be removed from output conduit 54 before the immiscible-fluid-discrete-volumes are deposited on a multi-well plate 47. The immiscible-fluid-discrete-volumes that do not contain ds nucleic acids can be moved through second waste conduit system 48, to waste reservoir 85. In some embodiments, a dye can be detected by detector 98 to determine whether a discrete volume should be sent to second waste reservoir 85 or be collected. Pump 87 can apply a negative pressure to waste conduit system 48, which can cause the movement of immiscible-fluid-discrete-volumes into waste reservoir 85.

Immiscible-fluid-discrete-volumes deposited on multi-well plate 47 can be subjected to a sequencing reaction to form a detectable product, and the method of the present teachings can comprise detecting the detectable product. In various embodiments, the detectable product can be detected using, for example, a flow cell or a capillary electrophoretic sequencer. In various other embodiments, an off-capillary detector can be used as deemed appropriate.

Shown below is Table 1, which shows a state diagram of various settings that can be implemented for the various valves and detectors of the system shown in FIGS. 1A and 1B, to achieve various different functions, for example, an embodiment of the de novo sequencing method described above.

TABLE 1

| | V-1 | V-2 | V-3 | V-4 | V-5 | V-6 | V-7 | V-8 | V-9 | V-10 | V-11 | V-12 | V-13 | V-14 | V-15 | V-16 | V-17 | V-18 | V-19 | V-20 | V-21 | V-22 | V-23 | V-24 |
|---|---|---|---|---|---|---|---|---|---|---|---|---|---|---|---|---|---|---|---|---|---|---|---|---|
| Prime SMA Sample | 0 | 1 | 0 | 1 | 0 | 0 | | | | | | 0 | | | | | | 1 | 0 | 1 | | | | |
| | 0 | 1 | 0 | 1 | 0 | 0 | | | | | | 0 | | | | | | 0 | 0 | 1 | | | | |
| | 0 | 1 | 0 | 1 | 0 | 0 | | | | | | 0 | | | | | | 0 | 0 | 1 | | | | |
| Deliver initial portion of SMAF/MM mixture to ZT-1 | 0 | 1 | 0 | 1 | 0 | 0 | | | | | | 0 | | | | | | 1 | 0 | 1 | | | | |
| | 0 | 0 | 1 | 0 | 1 | 0 | 0 | | | | | 0 | | | | | | | 1 | 0 | | 1 | | |
| Deliver initial portion of oil to ZT-1 | 0 | 0 | 0 | 0 | 0 | 0 | 0 | | | | 0 | 1 | 1 | 0 | 1 | 0 | 0 | 0 | 0 | | | 1 | | |
| Form initial SMAF Zebra | 0 | 0 | 1 | 0 | 1 | 0 | 1 | 0 | | | 0 | 1 | 1 | 0 | 1 | 0 | 1 | 1 | 0 | 0 | 0 | 1 | | |
| Deliver intermediate portion(s) of SMAF.MM mixture to ZT-1 | 0 | 1 | 0 | 1 | 0 | 0 | | | | | | | | | | | | | 1 | 1 | | 1 | | |
| | 0 | 0 | 1 | 0 | 1 | 0 | 1 | 0 | | | | 0 | 1 | 1 | 0 | 1 | 0 | 1 | 0 | 0 | 0 | 0 | 1 | |
| Deliver final portion(s) of SMAF.MM mixture toZT-1 | 0 | 1 | 0 | 1 | 0 | 0 | | | | | | | | | | | | 1 | 0 | 1 | 1 | 1 | | |
| | 0 | 0 | 1 | 0 | 1 | 0 | 1 | 0 | | | | 0 | 1 | 1 | 0 | 1 | 0 | | 0 | 0 | 0 | 1 | | |
| Amplify DNA | | | | | | | 0 | 0 | | | | | | | | | | | | | | 0 | | |
| Prime ES reagent path | | | | | | | 0 | 0 | 1 | 1 | | | | | | | | | | | | 1 | | |
| | | | | | | | 0 | 0 | 1 | 1 | | | | | | | | | | | | | | |
| Add ES reagents and load clean up thermal cycler | | | | | 0 | 0 | 1 | 1 | 1 | 1 | 1 | 0 | 1 | 1 | 0 | 1 | 0 | | | 0 | 0 | 0 | 0 | |
| Clean up after PCR Prime PF + BD paths | | | | | 0 | 0 | 1 | 1 | 1 | 1 | 1 | 0 | 1 | 1 | 0 | 1 | 0 | | | 0 | 0 | 0 | 0 | |
| | | | | | | | 0 | 0 | | | | | | | | | | | | | | | | |
| | | | | | | | | | 0 | 0 | 0 | | | | | | | | | | | | | 1 |
| | | | | | | | | | 0 | 0 | 0 | | | | | | | | | | | | | 1 |
| Add FP + BD and RP + BD & load cycle sequencing sticky bun | | | | 0 0 | 0 0 | 1 1 | 1 1 | 1 1 | 1 1 | 1 1 | 0 0 | 1 1 | 1 1 | 0 0 | 1 1 | 0 0 | | | 0 0 | 0 0 | 0 0 | 0 0 | | |
| Cycle sequence | | | | | | | 0 | 0 | 0 | | | | | | | | | | | | | | | 0 |
| Dispense sample-laden FP slugs to tray, dispose of other fluids | | | | 0 0 | 0 0 | 1 1 | 1 1 | 1 1 | 1 1 | 0 0 | 0 0 | 1 1 | 1 1 | 0 0 | 1 1 | 0 0 | | | 0 0 | 0 0 | 0 0 | 0 0 | | |

| | V-25 | V-26 | Rotary Valve-ES | Rotary Valve-FP&BD | Rotary Valve-MM_SMF | Rotary Valve-MM_VI | VICI-1 | VICI-2 | SP-MM | SPES | SP-FP&BD | SP-RP&BD | Footnote |
|---|---|---|---|---|---|---|---|---|---|---|---|---|---|
| Prime SMA Sample | | | | | 0 | | 0 | 1 | | | | | 1 |
| | | | | | Oil | 0 | | 1 | | | | | 2 |
| | | | | | MM | 0 | | 1 | | | | | 3 |
| Deliver initial portion of SMAF/MM mixture to ZT-1 | | | | | MM | 0 | | 1 | | | | | 4 |
| | | | | | MM | 0 | | 1 | | | | | 5 |
| Deliver initial portion of oil to ZT-1 | | | | | Off | 0 | 1 | | | | | | 6 |
| Form initial SMAF Zebra | | | | | | | | | | | | | 7 |
| Deliver intermediate portion(s) of SMAF.MM mixture toZT-1 | | | | | MM | 0 | | 1 | | | | | 8 |
| | | | | | | | 1 | 1 | | | | | 9 |
| Deliver final portion(s) of SMAF.MM mixture toZT-1 | | | | | MM | 0 | | 1 | | | | | 10 |
| | | | | | | | 1 | 1 | | | | | 11 |
| Amplify DNA Prime ES reagent path | | | 0 | | | | | | | | | | 12 |
| | | | Oil out | | | | | | | | | | |
| | | | ES out | | | | | | | | | | 13 |

TABLE 1-continued

| | | | | | | | | | | | | | |
|---|---|---|---|---|---|---|---|---|---|---|---|---|---|
| Add ES reagents and load clean up thermal cycler | 0 | | out | 0 | | 0 | 0 | 1 | 0 | out | 0 | 0 | 14 |
| Clean up after PCR | 0 | | 0 | 0 | | 0 | 0 | 1 | 0 | 0 | 0 | 0 | 15 |
| Prime PF + BD paths | | | | | | | | | | | | | 16 |
| | | 1 | | Oil out | | Oil out | | | | | In out | In out | 17 |
| | | | | | | | | | | | In | In | 18 |
| | | | | FP | | RF | | | | | In | In | 19 |
| | | | | BD | | BD | | | | | In | In | 20 |
| | | 1 | | Oil out | | Oil out | | | | | In out | In out | 21 |
| Add FP + BD and RP + BD & load cycle sequencing sticky bun | 0 0 | | 0 0 | out 0 | | out 0 | 1 1 | 0 0 | 0 0 | 0 0 | 1 0 | 1 0 | 22 |
| Cycle sequence | 0 | | | 0 | | 0 | | | | | | | |
| Dispense sample-laden FP slugs to tray, dispose of other fluids | 0 0 | 1 0 | 0 0 | 0 0 | | 0 0 | 1 1 | | | | | | 23, 24 |

Footnotes:
1 Pull SMAF into T-intersection (67)
2 Pull oil through T-intersection (67);
3 Pull MM through T-intersection (67);
4 Pull SMAF + MM through D-17;
5 Push SMAF + MM towards T-intersection (66) until D-5 detects AF;
6 Pull, Push oil towards T-intersection (66) until D-4 detects oil;
7 Push oil + SMAF + MM through thermal cycler until D-6 detects zebras or, more likely, D-2 sees only oil;
8 Pull SMAF + MM through D-17;
9 Push oil + SMAF + MM through thermal cycler until D-6 detects zebras or, more likely, D-2 sees only oil;
10 Pull SMAF + MM towards D-17. After total volume of SMAF has entered T-intersection (67), close V-18. After total volume of MM has left Rotarty Valve (71), switch Rotary Valve (71) to "oil" position. Continue pulling SMAF + MM towards D-17 until D-2 sees a;
11 Push oil + SMAF + MM through thermal cycler until D-6 detects zebras or, more likely, D-5 sees only oil;
12 Push oil until D-16 detects oil;
13 Push ES until D-18 detects ES, then push further distance calculated to advance ES to Zebra path.;
14 Push until D-6 detects end of batch, then push further distance calculated to advance batch just past ES adder;
15 Push until D-9 detects end of batch, then push farther distance calculate to advance batch completely into cleanup thermal cycler;
16 Push SP (78) until D-19 sees oil. Push SP (82) until D-20 sees oil.;
17 Pull portion of FP into SP (78). Pull portion of RP into SP (82);
18 Pull portion of BD into SP (78). Pull portion of BD into SP (82);
19 Pull alternating sub-portions of primers and big dyes until complete portion has been loaded;
20 Pull small amount of oil so all aqueous fluids advance into syringe;
21 Push SP (78) until D-19 sees FP + BD. Push SP (82) until D-20 sees RP + BD. Push farther distance calculated to advance FP + BD and RP + BD to Zebra path;
22 Push with pumps until D-11 and D-7 see oil, then push further distance calculated to advance batch just past RP + BD and FP + BD adders;
23 Push with pumps further distance calculated to advance batch into cycle sequencing thermal cycler;
24 Push until FSD-1 detects sample-laden FP slug, then push further distance calculated to move downstream boundary of sample-laden slug just inside dispense tip;
25 Push distance calculated to bead sample-laden slug on dispense tip. Touch bead to bottom of temple well.

According to various embodiments, the present teachings can encompass a resequencing method using system 10. In general, the resequencing method is similar to the de-novo method described herein with modifications as discussed herein.

In some embodiments, the pre-processing of a sample for resequencing comprises shearing a robust sample of nucleic acid having a plurality of copies of one or more nucleic acids of interest, herein also referred to as target sequences. The nucleic acids in the sample can be sheared. The method can comprise adding a plurality of gene specific zip code primers to the sample before introduction to system 10, or the gene specific zip code primers can be added, at for example, at cross-junction 10, to a set of immiscible-fluid-discrete-volumes generated from the sample. Immiscible-fluid-discrete-volumes made from the sample can contain a single copy of a nucleic acid fragment or can contain a plurality of copies of one or more different nucleic acid fragments. Each immiscible-fluid-discrete-volume can contain, for example, from about 50 to about 150 different gene-specific zip code primers. The gene-specific zip code primers can be present at a relatively low concentration. Exemplary low concentrations can comprise from about 0.1 nanomolar primers per nanoliter (primers/nl) to about 1 micromolar primers/nl, or from about 10 nanomolar primers per nanoliter (primers/nl) to about 50 nanomolar primers/nl.

According to some embodiments, the method can comprise adding sequence-specific zip code primers, specific to a single zip code sequence, to each immiscible-fluid-discrete-volume of a set of immiscible-fluid-discrete-volumes. The sequence-specific zip code primers added to each immiscible-fluid-discrete-volume can be different for one immiscible-fluid-discrete-volume than for at least one other immiscible-fluid-discrete-volume, and can be complementary to the zip code sequences of a specific set of gene-specific zip code primers. The sequence-specific zip code primers can be present in a high concentration relative to the concentration of the gene-specific zip code primers. For example, the concentration of the sequence specific zip code primers can be in excess, and the concentration of the gene specific zip code primers can be limiting. The concentration of the sequence specific zip code primers can be present, relative to the concentration of the gene-specific zip code primers, at, for example, a ratio of from about 10 nanomolar to about 1 micromolar, or from about 100 nanomolar to about 500 nanomolar.

In some embodiments, the method can comprise moving a set of immiscible-fluid-discrete-volumes comprising the concentrations of primers discussed above, to thermal spiral 74. The set of immiscible-fluid-discrete-volumes can be thermally cycled and thereafter processed in any of the many manners disclosed herein for the de novo sequencing method. Various sequencing and re-sequencing methods that can be carried out according to various embodiments can include, for example, those depicted in FIGS. 2C-2K of U.S. Patent Application Publication No. 2007/0141593 A1, which is incorporated herein in its entirety by reference.

Shown below are Tables 2A and 2B which are the first and second halves of another state diagram of various settings that can be implemented for the various valves and detectors of the system shown in FIGS. 1A and 1B, to achieve various different functions. The various functions can include carrying out various different immiscible-fluid-discrete-volume processing, for example, carrying out the standard resequencing reactions depicted in FIGS. 2C-2D of U.S. Patent Application Publication No. 2007/0141593 A1.

TABLE 2A

| | V-1 | V-2 | V-3 | V-4 | V-5 | V-6 | V-7 | V-8 | V-9 | V-10 | V-11 | V-12 | V-13 | V-14 | V-15 | V-16 | V-17 | V-18 | V-19 | V-20 | V-21 |
|---|---|---|---|---|---|---|---|---|---|---|---|---|---|---|---|---|---|---|---|---|---|
| Prime Primary VI Input Path | 0 | | | | 0 | 0 | | | | | | | 0 | 0 | 1 | 0 | 1 | | | | |
| Form VI Zebra | 0 | | | | 0 | 0 | | | | | | | 0 | 0 | 1 | 0 | 1 | | | | |
| | 0 | | | | 0 | 0 | | | | | | | 0 | 0 | 1 | 0 | 1 | | | | |
| | 0 | | | | 0 | 0 | | | | | | | 0 | 0 | 1 | 0 | 1 | | | | |
| | 0 | | | | 0 | 0 | | | | | | | 0 | 0 | 1 | 0 | 1 | | | | |
| | 0 | | | | 0 | 0 | | | | | | | 0 | 0 | 1 | 0 | 1 | | | | |
| Push Zebra Into Storage | 0 | | | | 0 | 0 | 0 | | | | | | 1 | 1 | 0 | 1 | 0 | | | | 1 |
| Repeat "Form VI Zebra" and "Push Zebra Into Storage" until D-4 sees zebras or until the total required number of slugs is reached. | | | | | | | | | | | | | | | | | | | | | |
| Prime Secondary VI Input Path | 1 | 1 | 0 | 1 | 0 | 0 | | | | | | | 0 | 0 | | | | 0 | 0 | 1 | |
| Form secondary VI fluid macro slugs | 1 | 1 | 0 | 1 | 0 | 0 | | | | | | | 0 | 0 | | | | 0 | 0 | 1 | |
| | 1 | 1 | 0 | 1 | 0 | 0 | | | | | | | 0 | 0 | | | | 0 | 0 | 1 | |
| | 1 | 1 | 0 | 1 | 0 | 0 | | | | | | | 0 | 0 | | | | 0 | 0 | 1 | |
| Push Macro-Zebra Into Storage | | 0 | 1 | 0 | 0 | 0 | | | | | | | | | | | | | 1 | 0 | |
| Repeat "Form secondary VI fluid macro slugs" and "Push Macro-Zebra Into Storage" until D-4 sees zebras or until the total required number of slugs is reached. | | | | | | | | | | | | | | | | | | | | | |
| Add Secondary VI fluid to Zebra slugs | | 0 | 1 | 0 | 0 | 1 | 0 | 0 | | | | | 0 | 1 | 1 | 0 | 1 | 0 | 1 | 0 | 0 |
| Prime MM_VI | | | | | | | | | | | | | | | | | | | | | |
| Add MM to VI Zebra slugs | | 0 | 1 | 0 | 0 | 1 | 1 | 0 | | | | | 0 | 1 | 1 | 0 | 1 | 0 | 1 | 0 | 0 |
| Amplify DNA | | | | | | | 0 | 0 | | | | | | | | | | | | | |

| | V-22 | V-23 | V-24 | V-25 | V-26 | Rotary Valve (75) | Rotary Valve (77) | Rotary Valve (71) | Rotary Valve (73) | Rotary Valve (79) | Pump (40) | Pump (39) | SP (58) |
|---|---|---|---|---|---|---|---|---|---|---|---|---|---|
| Prime Primary VI Input Path | | | | | | | | | | | 1 | | |
| Form VI Zebra | | | | | | | | | | | 1 | | |
| | | | | | | | | | | | 1 | | |
| | | | | | | | | | | | 1 | | |
| | | | | | | | | | | | 1 | | |
| | | | | | | | | | | | 1 | | |
| Push Zebra Into Storage | 1 | | | | | | | | | | 1 | | |
| Repeat "Form VI Zebra" and "Push Zebra Into Storage" until D-4 sees zebras or until the total required number of slugs is reached. | | | | | | | | | | | | | |
| Prime Secondary VI Input Path | | | | | | | | | | | 1 | | |
| Form secondary VI fluid macro slugs | | | | | | | | | | | 1 | | |
| | | | | | | | | | | | 1 | | |
| | | | | | | | | | | | 1 | | |
| Push Macro-Zebra Into Storage | | | | | | | | | | | | | |
| Repeat "Form secondary VI fluid macro slugs" and "Push Macro-Zebra Into Storage" until D-4 sees zebras or until the total required number of slugs is reached. | | | | | | | | | | | | | |
| Add Secondary VI fluid to Zebra slugs | 1 | 0 | | | | | | | | 0 | 1 | 1 | 0 |
| Prime MM_VI | | | | | | | | | 0 | MM | | | 1 |
| Add MM to VI Zebra slugs | 0 | 1 | | | | | | | | Out | 1 | 1 | 1 |
| Amplify DNA | | 0 | | | 0 | | | | | | | | |

TABLE 2A-continued

|  | SP (66) | SP (78) | SP (82) |
| --- | --- | --- | --- |
| Prime Primary VI Input Path | | | Pull oil from reservoir until it reaches D-15, then pump distance calculated to advance oil at D-17 just past V-17. |
| Form VI Zebra | | | Pull 78 nl primary VI fluid into tube through tip. Wash tip. Pull 800 nl oil into tube through tip. Wash tip. Pull 78 nl primary VI fluid from next well into tube through tip. Wash tip. Pull 800 nil oil into tube through tip. Wash tip. Continue aspiration steps until zebras (sequence of immiscible fluid volumes) are detected by D-15. |
| Push Zebra Into Storage | | | Push oil until D-16 no longer sees slugs (individual fluid volumes). |
| Repeat "Form VI Zebra" and "Push Zebra Into Storage" until D-4 sees zebras or until the total required number of slugs is reached. | | | |
| Prime Secondary VI Input Path | | | Pull oil from reservoir until it reaches D-15, then pump distance calculated to advance oil at D-17 just past V-17. |
| Form secondary VI fluid macro slugs | | | Pull m(78 nl) of secondary VI fluid i into tube, where m is the number of primary VI fluids that are to be mixed with the ith secondary fluid. Pull 800 ml oil into tube through tip. Wash tip. Continue aspiration steps until zebras are detected by D-17. |
| Push Macro-Zebra Into Storage | | | Pump oil to push macro-zebra until D-2 no long sees macro-slugs. |
| Repeat "Form secondary VI fluid macro slugs" and "Push Macro-Zebra Into Storage" until D-4 sees zebras or until the total required number of slugs is reached. | | | |
| Add Secondary VI fluid to Zebra slugs | | | Push micro and macro zebras until D-3 sees slugs |
| Prime MM_VI | | | Load Syringe Pump (58) |
| Add MM to VI Zebra slugs | | | Runs pumps until D-6 sees slugs |
| Amplify DNA | | | |

TABLE 2B

| | V-1 | V-2 | V-3 | V-4 | V-5 | V-6 | V-7 | V-8 | V-9 | V-10 | V-11 | V-12 | V-13 | V-14 | V-15 | V-16 | V-17 | V-18 | V-19 | V-20 | V-21 |
| --- | --- | --- | --- | --- | --- | --- | --- | --- | --- | --- | --- | --- | --- | --- | --- | --- | --- | --- | --- | --- | --- |
| Prime ES Reagent path | | | | | | | | 0 0 | 0 0 | 1 1 | 1 1 | | | | | | | | | | |
| Add ES Reagents & thermal cycler load cleanup | | | | | 0 0 | 0 0 | 1 1 | 1 1 | 1 1 | 1 1 | 1 1 | 0 0 | 1 1 | 1 1 | 0 0 | 1 1 | 0 0 | | | | 0 0 |
| Clean up after PCR | | | | | | | | 0 | 0 | | | | | | | | | | | | |
| Prime FP + BD and RP + BD paths | | | | | | | | | 0 0 | 0 0 | 0 0 | | | | | | | | | | |
| Add FP + BD and RP + BD & load cycle sequencing thermal cycler | | | | | 0 0 | 0 0 | 1 1 | 1 1 | 1 1 | 1 1 | 1 1 | 0 0 | 1 1 | 1 1 | 0 0 | 1 1 | 0 0 | | | | 0 0 |
| Cycle sequence | | | | | | | | 0 | 0 | 0 | | | | | | | | | | | |
| Dispense sample-laden FP slugs to tray, dispose of other fluids | | | | | 0 0 | 0 0 | 1 1 | 1 1 | 1 1 | 1 1 | 0 0 | 0 0 | 1 1 | 1 1 | 0 0 | 1 1 | 0 0 | | | | 0 0 |

| | V-22 | V-23 | V-24 | V-25 | V-26 | Rotary Valve (75) | Rotary Valve (77) | Rotary Valve (71) | Rotary Valve (73) | Rotary Valve (79) | Pump (40) | Pump (39) | SP (58) |
| --- | --- | --- | --- | --- | --- | --- | --- | --- | --- | --- | --- | --- | --- |
| Prime ES Reagent path | | 1 | 1 | | | Oil Out ES Out | | | | | | | |
| Add ES Reagents & load cleanup thermal cycler | 0 0 | 0 0 | 0 0 | 0 0 | | Out 0 | 0 0 | | 0 0 | 0 0 | 1 1 | 0 0 | 0 0 |
| Clean up after PCR | | | | | | | | | | | | | |
| Prime FP + BD and RP + BD paths | | | 1 1 | 1 1 | | | Oil Out FP BD Oil Out | | Oil Out RP BD Oil Out | | | | |

TABLE 2B-continued

| | | | | | | | | | | | | | |
|---|---|---|---|---|---|---|---|---|---|---|---|---|---|
| Add FP + BD and RP + BD & load cycle sequencing thermal cycler | 0 | 0 | 0 | 0 | | 0 | Out | | 0 | Out | 1 | 0 | 0 |
| | 0 | 0 | 0 | 0 | | 0 | 0 | | 0 | 0 | 1 | 0 | 0 |
| Cycle sequence | | | 0 | 0 | | | 0 | | | 0 | | | |
| Dispense sample-laden FP slugs to tray, dispose of other fluids | 0 | 0 | 0 | 0 | 1 | 0 | 0 | | 0 | 0 | 1 | | |
| | 0 | 0 | 0 | 0 | 0 | 0 | 0 | | 0 | 0 | 1 | | |

| | SP (66) | SP (78) | SP (82) | |
|---|---|---|---|---|
| Prime ES Reagent path | In | | | |
| | Out | | | Push oil until D-18 detects oil. |
| | In | | | |
| | Out | | | Push ES until D-18 detects ES, then push further distance calculated to advance ES to zebra path. |
| Add ES Reagents & load cleanup thermal cycler | Out | 0 | 0 | Push until D-6 detects end of batch, then push further distance calculated to advance batch just past ES adder. |
| | | 0 | 0 | Push until D-9 detects end of batch, then push further distance calculate to advance batch completely into cleanup thermal cycler. |
| Clean up after PCR | | | | |
| Prime FP + BD and RP + BD paths | | In | In | |
| | | Out | Out | Push SP-FP&BD until D-19 sees oil. Push SP (82) until D-20 sees oil. |
| | | In | In | Pull portion of FP into SP (78). Pull portion of RP into SP-RP&BD. |
| | | In | In | Pull portion of BD into SP (78). Pull portion of BD into SP (82). Pull alternating sub-portions of primers and big dyes until complete portion has been loaded. |
| | | In | In | Pull small amount of oil so all aqueous fluids advance into syringe. |
| | | Out | Out | Push SP (78) until D-19 sees FP + BD. Push SP (82) until D-20 sees RP + BD. Push farther distance calculated to advance FP + BD and RP + BD to zebra path. |
| Add FP + BD and RP + BD & load cycle sequencing thermal cycler | 0 | 1 | 1 | Push with pumps until D-11 and D-7 see oil, then push further distance calculated to advance batch just past RP + BD and FP + BD adders. |
| | 0 | 0 | 0 | Push with pumps further distance calculated to advance batch into cycle sequencing thermal cycler. |
| Cycle sequence | | | | |
| Dispense sample-laden FP slugs to tray, dispose of other fluids | | | | Push until fluorescent detector (98) detects sample-laden FP slug, then push further distance calculated to move downstream boundary of sample-laden slug just inside dispense tip. Push distance calculated to bead sample-laden slug on dispense tip. Touch bead to bottom of sample well. |

Figure 1C:
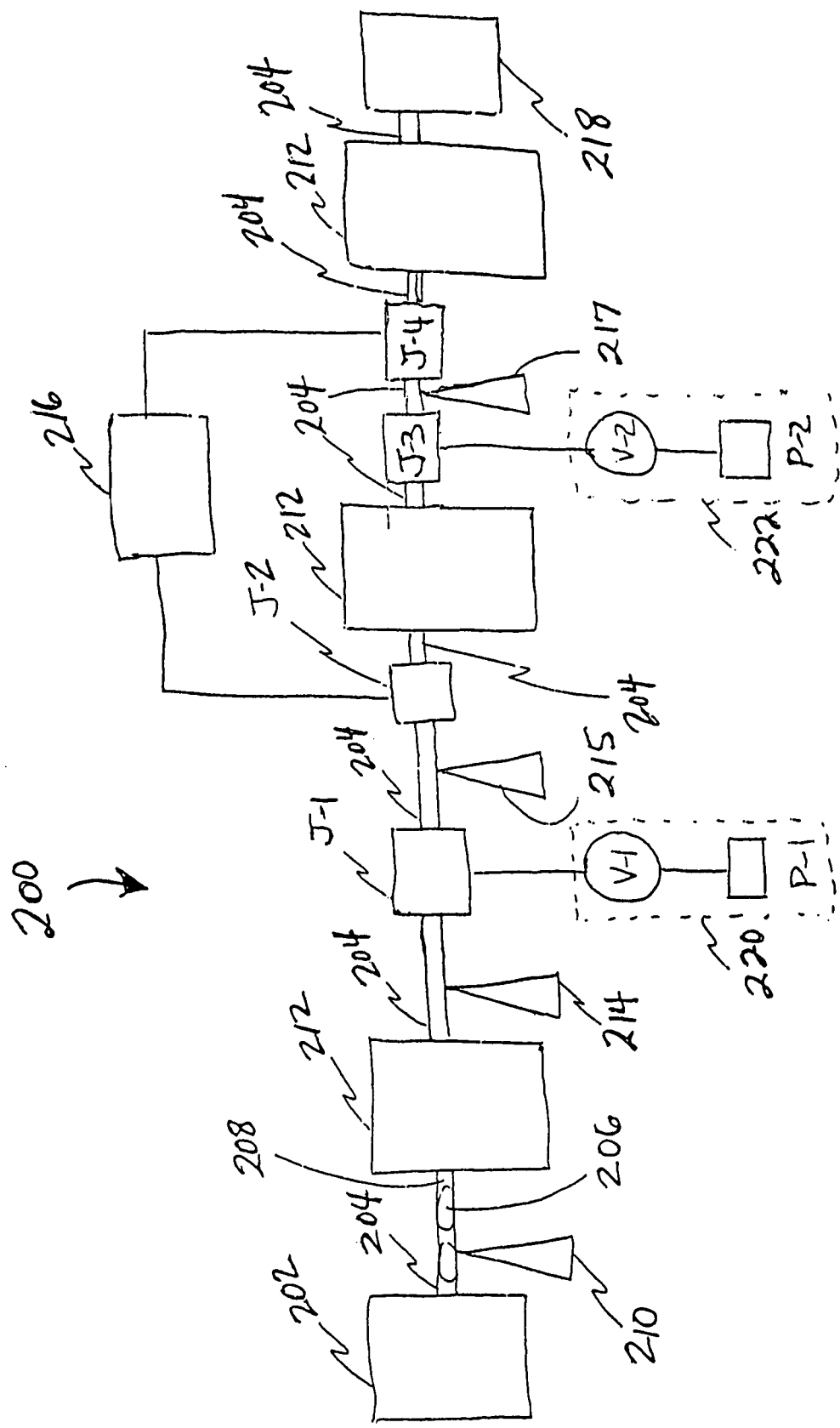
FIG. 1C is a simplified block diagram of a system configured to include embodiments described herein and to process the generated immiscible-fluid-discrete-volumes and to output the immiscible-fluid-discrete-volume.

FIG. 1C is yet another system for processing immiscible-fluid-discrete volumes downstream of the apparatuses, methods, and systems disclosed herein.

A simplified system 200 is illustrated in FIG. 1C. As illustrated, box 202 represents a structure that delivers to tube 204 of system 200 discrete volumes 206 of aqueous liquid in a non-aqueous liquid 208 with which they are immiscible. Examples of such structures and methods of generating discrete volumes 206 in contact with spacing fluid 208 are described herein. In some embodiments, such a structure could be a tube of preformed discrete volumes 206 of aqueous fluid. In some embodiments, such a structure could be a chip or other substrate with a channel therein containing the discrete volumes 206 of aqueous fluid. As illustrated, tube 204 extends throughout system 200. After entering tube 204, desired information about aqueous volumes 206 are determined and optionally manipulated by structures in triangle 210. For example, the length and speed of a slug and the distance between two adjacent slugs can be desired information. In that example, a slug detection system can provide that information. If the distance between adjacent slugs does not meet preferred values, then additional spacing fluid can be added between the trailing point of the first slug and the leading point of the second slug, or one of the slugs could be held in an electric field, for example, to allow more of the existing spacing fluid to flow past it in tube 203. If the length, and therefore the volume, of an aqueous discrete volume does not meet preferred values, additional non-reactive, miscible liquid can be added by an apparatus at that area of tube 204. Triangle 210 represents these and other structures of discrete volume characteristic detection and manipulation. Examples of these structures and/or component parts of thereof are described herein.

System 200, as illustrated in FIG. 1C, next incorporates a processing section 212 of tube 204 (not illustrated, but in the box), which can include, for example, vibration, heating, cooling, and electromagnetic radiation exposure. In some embodiments, processing section 212 can include thermal cycling between one or more pre-determined temperatures for pre-determined durations as needed, for example, to perform PCR, or other amplification methods. In some embodiments, aqueous discrete volumes may continue to flow at a constant rate through processing section 212 while undergoing a desired process, or alternatively, they may dwell in a particular location in processing section 212. System 200, as illustrated in FIG. 1C, includes another aqueous discrete volume characteristic determination and optional manipulation station 214. Aqueous discrete volumes 206 then flow through a junction J-1. In some embodiments, junction J-1 can be a T. As illustrated, fluid addition station 220 includes pump P-1 and valve V-1 in conjunction with a supply of different fluid (not shown) and can add that fluid to tube 204. In some embodiments, a gas phase can be introduced between aqueous discrete volumes 206. In some embodiments, an aqueous liquid can be added to aqueous discrete volumes 206 in junction J-1. In some embodiments, the different aqueous fluid can be added a discrete volume between aqueous discrete volumes 206. An aqueous discrete volume characteristic determination and optional manipulation station 215, like 214 and 210 described above, follows liquid addition station 220. In some embodiments, station 215 evaluates the volume of liquid added to aqueous discrete volume 206.

Next in line, as illustrated in FIG. 1C, is junction J-2. Junction J-2 and junction J-4, further down the line, fluidically connect back pressure unit 216 to pressurize tube 204 to a desired pressure. Between junctions J-2 and J-4, system 200 includes a second processing section 212, a junction J-3, at which point, fluid adding station 222 can add a volume of liquid to pre-existing aqueous discrete volumes 206, and an aqueous discrete volume characteristic determination and optional manipulation station 217 can evaluate the volume of liquid added to aqueous discrete volume 206.

As illustrated in FIG. 1C, system 200 includes a final processing section 212, and processed aqueous discrete volumes are delivered from tube 204 to output station 218. Examples of structures used in output station 218 can include those described herein.

Reference will now be made to various embodiments of devices, apparatus, systems, and methods for depositing immiscible-fluid-discrete-volumes of a first fluid separated from one another by an immiscible spacing fluid, examples of which are illustrated in the accompanying drawings. Various embodiments of these can be used in the system described above with reference to FIGS. 1A and 1B. Wherever possible, the same reference numbers are used in the drawings and the description to refer to the same or like parts.

As shown in FIG. 2, according to embodiments of the present teachings, an immersion plate 102 can be provided on which to deposit of aqueous drops, for instance sample drops, in a pattern on a top surface of immersion plate 102. According to various embodiments, the deposited aqueous drops can be formed in a pattern aligned with the capillary tips of a capillary electrophoresis array or other processing device. According to various embodiments as shown in FIG. 2, immersion plate 102 can be filled with and contain a fluid 116, such as an oil, covering a bottom of a shallow, open cavity or recess of immersion plate 102. According to various embodiments, the surface of the open cavity or recess of immersion plate 102 can have areas that possess hydrophilic features, the hydrophilic features being surrounded by, for example, hydrophobic features or areas. According to various embodiments, the immersion plate 102 can receive a discharge tip 108 or other outlet nozzle of an immiscible-fluid-discrete-volume conduit 104 in the open cavity or recess of immersion plate 102. According to various embodiments in one regard, discharge tip 108 of immiscible-fluid-discrete-volume conduit 104 can be positioned under robotic control over, for example, hydrophilic areas of the bottom surface of immersion plate 102.

According to various embodiments as shown in FIG. 2, immiscible-fluid-discrete-volume conduit 104 can contain a set of aqueous discrete volumes 106, for example such as aqueous sample discrete volumes 106, that are separated by spacing fluid 110. According to various embodiments, spacing fluid 110 can be an oil, such as various oil formulations immiscible with aqueous discrete volumes 106, as described herein. According to various embodiments, pressure or vacuum can for example be applied to immiscible-fluid-discrete-volume conduit 104 to cause the discharge and deposition of aqueous discrete volumes 106 on a top surface of immersion plate 102. According to various embodiments, aqueous discrete volumes 106 can be injected onto desired areas of immersion plate 102 using other types of force, for example electrokinetic injection. According to various embodiments, spacing fluid 110 and fluid 116 can be the same fluid, such as the same oil.

As shown in FIG. 3, showing an enlarged view of a deposition area labeled A in FIG. 2, according to various embodiments, immersion plate 102 can have formed, on a surface of a shallow cavity or recess therein, a set of hydrophilic features 112. According to various embodiments, hydrophilic features 112 can be gold contact areas, such as electroplated dots or other feature shapes. It will be appreciated that while FIG. 3 illustrates three hydrophilic features as slightly raised contact areas and one as a depression with a rim around it, on a bottom surface of a shallow inner cavity or recess of immersion plate 102, in various embodiments hydrophilic features 112 can be formed in other configurations, such as lining the surface of a well or recess, formed flush in immersion plate 102, recessed in a surface of immersion plate 102 without a retaining rim, or the like. Other configurations of hydrophilic features 112 are also possible.

According to various embodiments, as shown in FIG. 3, immiscible-fluid-discrete-volume conduit 104 can deposit a set of deposited drops 114 deposited in contact with respective ones of hydrophilic features 112. More specifically, in embodiments as shown, immiscible-fluid-discrete-volume conduit 104 can be moved, for example under robotic control, sequentially over the locations of hydrophilic features 112. When discharge tip 108 is positioned over a next one of hydrophilic features 112, pressure or other force can be applied to immiscible-fluid-discrete-volume conduit 104, for example, by syringe pump, to expel a next one of aqueous volumes 106 to contact the underlying one of hydrophilic features 112, and thereby form a next one of deposited drops 114. According to various embodiments as shown, deposited drops 114 can be immersed below immersion fluid 116, such as an oil that is less dense than water. In some embodiments where spacing fluid 110 is heavier than water, spacing fluid 110 can be vacuumed away from tip 108 with a waste removal system such as that described with reference to FIGS. 4B, 5A, 12, 30 and 31. Alternatively, spacing fluid 110 can be collected in receptacles, for example, troughs 115 disposed between hydrophilic features 112.

According to various embodiments in one regard, aqueous volumes 106 can contain sample material that has been subjected to polymerase chain reaction (PCR) with one sulfhydryl-labeled primer, forming amplicons that are deposited as deposited drops 114 on hydrophilic features 112 of immersion plate 102. According to various embodiments, the shallow cavity or recess of immersion plate 102 can be immersed under fluid 116, deposited drops 114 do not evaporate, allowing, for example, a gold-thiol bond to form. According to various embodiments, the other strand can be stripped off, and sequencing extension and washing and injection can be performed, as for example described elsewhere herein. In some embodiments, an injection fluid can be added to the hydrophilic features, for example, under robotic control, to create similar-sized entrapped aqueous portions on the plate for injection purposes. According to various embodiments, immersion plate 102 can be re-immersed with fresh fluid 116, for example, injection fluid as described herein, while retaining bound analytes on hydrophilic features 112. According to various embodiments, deposited drops 114 can be used to make robust electrical contact with capillaries or other conduits contacting the areas of hydrophilic features 112, during capillary electrophoresis or other processing. Fluid 116, which again can be an oil, can prevent evaporation of deposited drops 114 and other aqueous or immiscible liquids processed on immersion plate 102.

According to various embodiments in a further regard, and more specifically, PCR, cycle sequencing, or other processing can be performed on aqueous volumes 106 in immiscible-fluid-discrete-volume conduit 104. Sequencing primers that can be used in processing of aqueous volumes 106 can contain the sulfhydryl group. Hydrophilic features 112 of immersion plate 102 can be made of gold, and bind the sequencing ladders. In view of the fact that the cavity or recess of immersion plate 102 is immersed under fluid 116, deposited drops 114 do not evaporate, allowing the gold-thiol bond to form. Immersion plate 102 can be washed to remove dye-terminators and salts. Immersion plate 102 can then be re-immersed with fluid 116, while retaining analyte with or without an aqueous liquid, on hydrophilic features 112. If retained analyte is contacted with a fresh fluid, the fresh fluid can contain reductant to cleave the gold-thiol bond, as well as make robust electrical contact with the tips of capillary electrophoresis capillaries or other intake conduits. Fluid 116 can prevent the evaporation of deposited drops 114 or other aqueous liquids, for example, fresh fluid and/or injection fluid described herein. According to various further embodiments, reductant is not necessarily required, if the voltage applied during injection is sufficient to reduce the gold-thiol bond. While components of a drop are bound to the surface through a gold-thiol bond, the surface of immersion plate 102 can be washed, rinsed, or otherwise treated. Then, deionized water can be added to the spot, with a low concentration of buffer, and in some cases a cleaving agent to cleave the thiol-gold bond. Cleavage can also occur through the application of voltage to the surface of immersion plate 102.

According to various embodiments in a further regard, hydrophilic features 112 can be non-conductive, and bind either amplicon or sequencing ladders through a mechanism other than gold-thiol bonding, such as a streptavidin hydrophilic feature that binds a biotinylated DNA. If the biotinylated DNA needs to be released later, the biotin can contain a photocleavable linker. According to various embodiments in this regard, where the surface of immersion plate 102 is non-conductive, deposited drops lodged on hydrophilic features 112 can be large enough that both a capillary and an electrode, or a capillary comprising an electrode, can contact the deposited drops. In some embodiments, immersion plate 102 can be provided with a temperature control device, for example, resistive heaters, a peltier device, a thermal cycler, or the like, to enable, for example, cycle-sequencing and/or release of bound analytes.

According to various embodiments, charge-neutral or positively-charged dye-terminators can be used for cycle sequencing of aqueous volumes 106. The aqueous volumes 106 so processed can be deposited onto hydrophilic features 112 of immersion plate 102, and directly injected into downstream capillary electrophoresis or other processes. Hydrophilic features 112 can, in various embodiments, be conducting or non-conducting. According to various embodiments, the ionic strength of the deposited drops 114 can be reduced by pre-loading each hydrophilic feature 112 with water or other low ionic strength liquid prior to depositing aqueous volumes 106 containing higher ionic strength sequencing reaction.

In some embodiments, one or more of the hydrophilic features can comprise a pre-deposited aqueous fluid deposited thereon. Through the forces of surface tension and due to the coalescing nature of aqueous samples, the pre-deposited aqueous fluid can attract and/or pull an immiscible-fluid-discrete-volume 106, discharged from discharge tip 108, to hydrophilic feature 112, enabling some degree of tolerance with respect to aligning discharge tip 108 with each hydrophilic feature 112.

Figure 4A:
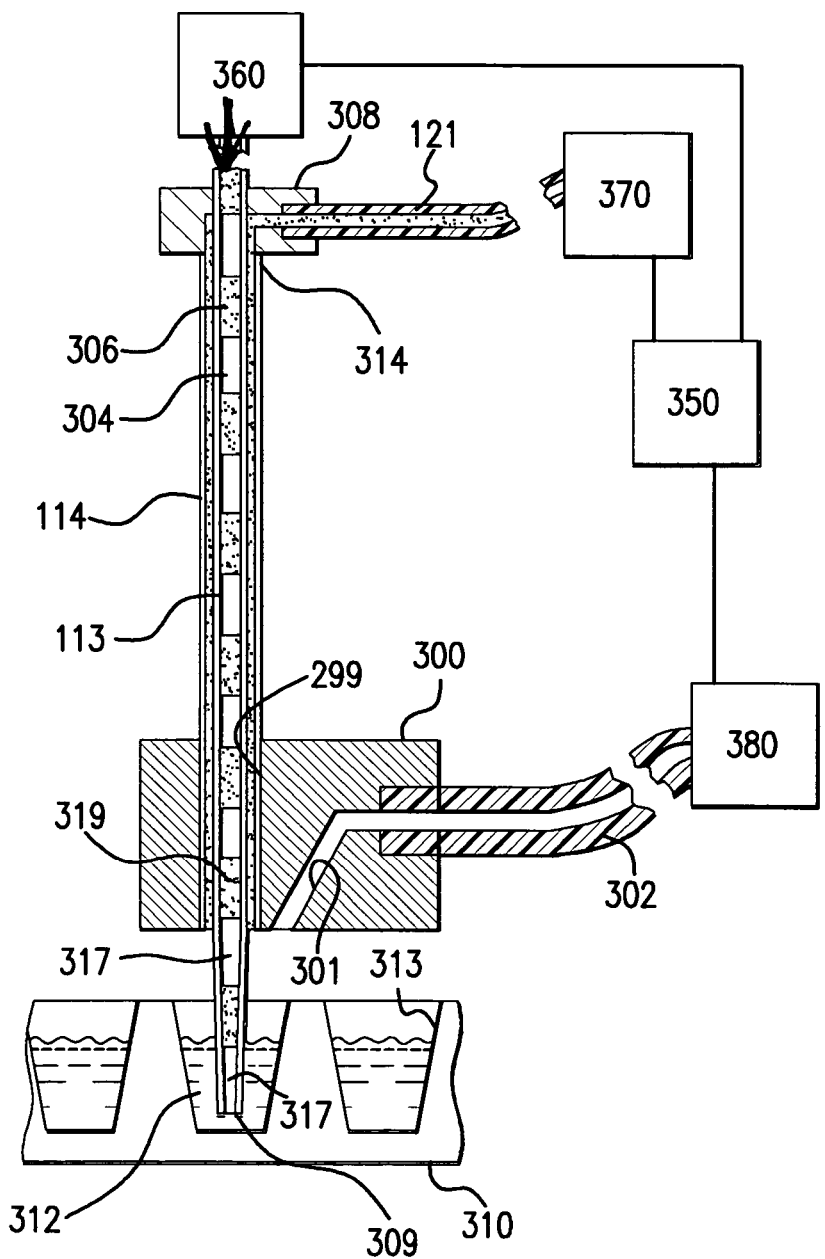
FIG. 4A illustrates a cross-sectional view of the inner tube positioned with its end surface beyond the end surface of the outer tube and a block that forms part of the tip rinsing apparatus, according to various embodiments.
Figure 4B:
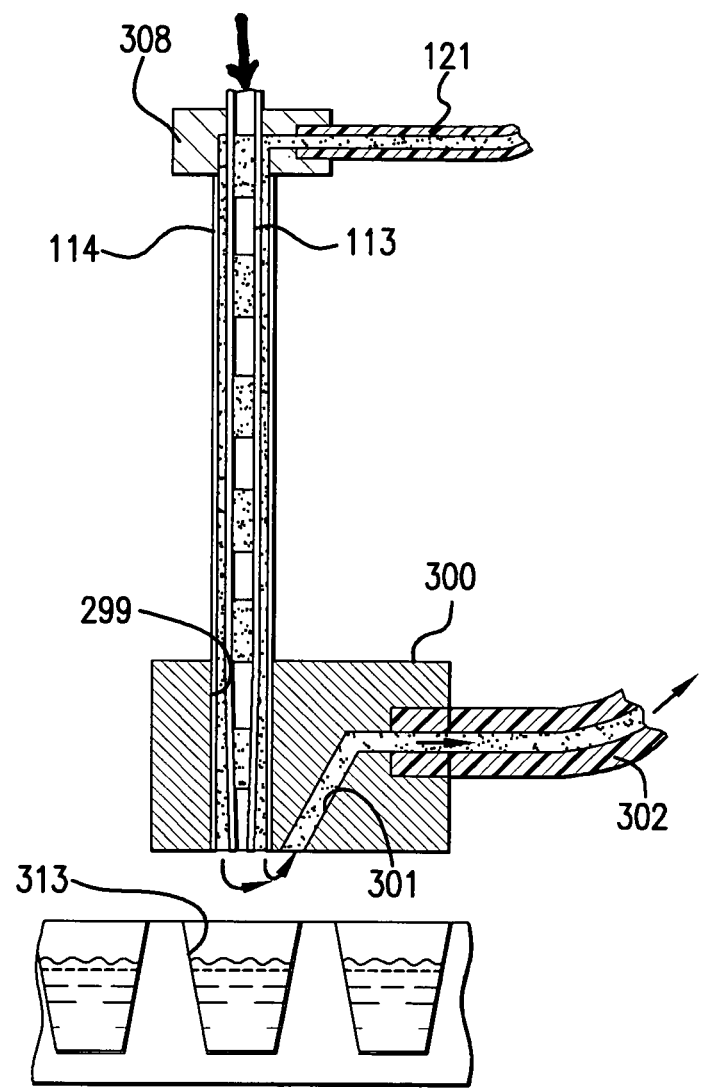
FIG. 4B illustrates a cross-sectional view of the inner tube positioned with respect to the outer tube such that the end surface of the inner tube is flush with the end surface of the outer tube, whereby the block can be used to rinse the conduit tip after a sample deposition step.

FIGS. 4A and 4B are cross-sectional side views of a system that can be used to deposit a desired discrete volume in a well of a sample tray. As shown in FIGS. 4A and 4B, an inner tube 113, is shown containing aqueous immiscible-fluid-discrete-volumes separated by one another with non-aqueous spacing fluid. Inner tube 113 can comprise polytetrafluoroethylene. According to various embodiments, materials other than polytetrafluoroethylene can be used to form the inner tube or the outer tube. The material can comprise, for example, one or more of silicone rubber, glass, butadiene rubber, other rubbers, nylon, other fluoropolymers, or polyethyleneterephthalate.

According to various embodiments, an apparatus is provided comprising a first conduit exemplified herein as an inner tube, a second conduit exemplified herein as an outer tube, a first pump, and a second pump. The inner tube can comprise a length, an inner surface, an outer surface, an outer diameter, and at least a first end surface, and the outer tube can comprise a length, an inner surface, an inner diameter, an outer surface, and at least a second end surface, wherein the inner tube can be positioned within the outer tube and the inner diameter of the outer tube is greater than the outer diameter of the inner tube such that a fluid can flow in a space. between the outer surface of the inner tube and the inner surface of the outer tube. The first pump can be in fluid communication with the inner tube, wherein the first pump is configured to flow a fluid through the inner tube in a first direction, and the second pump can be in fluid communication with the outer tube, where the second pump can be configured to flow a fluid through the outer tube in a second direction opposite the first direction. It should be understood that while tubes are exemplified herein, any suitable conduits can instead be used, and the conduits do not have to have any particular shape or dimensions. In various embodiments, at various times the end surface of the inner tube can be positioned beyond the end surface of the outer tube. In various embodiments, the outer diameter of the inner tube can be less than about 10 mm, less than about 1 mm, or less than 0.1 mm. In other embodiments, the inner diameter of the outer tube can be greater than about 10 mm, greater than about 1 mm, or greater than about 0.1 mm. Regardless of the outer diameter or perimeter of the inner tube, the inner diameter or perimeter of the outer tube will be greater than the outer diameter or perimeter of the inner tube, such that a fluid passage can be formed in the space between the outer tube and the inner tube.

According to various embodiments, the apparatus can comprise a control unit configured to synchronize actuation of the first pump and the second pump. According to various embodiments, the apparatus can comprise a conduit positioner configured to move at least one of the inner tube and the outer tube with respect to the other. In various embodiments, the apparatus can comprise a control unit configured to synchronize actuation of the first pump, the second pump, and the conduit positioner. The synchronized actuation of the pumps and conduit positioner can result in production of a plurality of aqueous immiscible-fluid-discrete-volumes, each of which is immiscible with a non-aqueous spacing fluid that separates the aqueous immiscible-fluid-discrete-volumes from one another. In various embodiments, the actuation of the pumps and conduit positioner can result in rinsing the tip of the inner tube between sample liquid depositing steps, thereby avoiding contamination of a subsequently deposited sample liquid with the previously deposited sample liquid. One of skill in the art can determine additional patterns of actuation of the pumps and the conduit positioner, as well as appropriate pump pressures, to accomplish a desired result.

According to various embodiments, the apparatus can comprise a block in the form of a housing, shroud, casing, or the like. The block can comprise a through-hole having a diameter that is greater than the outer diameter of the inner tube or maximum outer dimension of an inner conduit of a different shape. The block having a through-hole can take the place of an outer tube and can function as the outer fluid conduit, as shown in FIGS. 30 and 31, or, in another embodiment, can be provided in addition to an inner tube and an outer tube. At least a portion of the inner tube can be disposed in the through-hole of the block. In various embodiments, an inner conduit, an outer conduit, and a block can all three be included in the apparatus, and the end surface of the outer conduit can be disposed within the through-hole of the block, and/or the end surface of the inner tube can be disposed within the through-hole of the block. In other embodiments, the inner conduit can extend beyond the end surface of the outer conduit and beyond the block.

According to various embodiments, the apparatus can comprise a block having a through-hole, and a passageway in the block, the passageway can be in direct fluid communication with the through-hole as a result of the junction of the through-hole and the passageway in the block. According to various embodiments, the apparatus can comprise a pump in fluid communication with the passageway and configured to draw fluid from the conduits in the through-hole and into the passageway. In other embodiments, the passageway may not be in direct fluid communication with the through-hole. Rather the open end of the through-hole and an open end of the passageway may be in sufficiently close proximity such that a fluid from a tube in the through-hole can be sucked into the open end of the passageway. The passageway can lead to or be operatively connected to a waste container or other container into which the fluid can be deposited.

According to various embodiments, a system is provided comprising an apparatus and a supply of oil. In various embodiments, the apparatus can also comprise a supply of an aqueous liquid, for example, an aqueous biological sample solution, or other aqueous-based reagents. In various embodiments, the system can comprise sample liquid disposed in a sample container, and the positioner is configured to move the tip of the inner tube into the sample container and into contact with the sample liquid.

According to various embodiments, the method can comprise moving the inner conduit into the outer conduit such that the end surface of the inner conduit and the end surface of the outer conduit are flush or relatively flush with one another, that is, within one millimeter or less of each other, or such that the end surface of the inner conduit can be inside the outer conduit. Various embodiments can comprise moving the end surface of the outer conduit into a through-hole of a block or shroud, such that the end surface of the outer conduit us inside the through-hole.

According to various embodiments, the method can comprise rinsing the end surface of the inner conduit with the first fluid, and drawing away from the end surface of the inner conduit the first fluid used to rinse the end surface of the inner conduit. In various embodiments, the fluid used to rinse the end surface the inner conduit can be flushed through a passageway of a block. According to various embodiments, the block can comprise a passageway and the method can comprise drawing the first fluid used to rinse the end surface of the inner conduit through-the passageway and away from the through-hole.

According to various embodiments, aqueous immiscible-fluid-discrete-volumes can be confined between oil immiscible-fluid-discrete-volumes that can act as a spacer material to preserve individuality of the aqueous immiscible-fluid-discrete-volumes. According to various embodiments, the flow in the tube, channel, or other conduit can be laminar, with a velocity profile along the tube's axial orientation, with little or no velocity component in the radial direction.

According to various embodiments, the tip of inner tube 113 can be rinsed between aqueous liquid depositing or discharging steps. A suction can be directly applied to outer tube 114 or can be applied to another tube or passageway that is located close to outer tube 114, and/or can be located in a block 300, as exemplified in FIG. 4B. In some embodiments where a block 300 is used, outer tube 114 can be omitted and the discharge tip of inner tube 113 can be rinsed off by a liquid that is vacuumed away through block 300.

FIGS. 4A and 4B illustrate an apparatus that can collect an aqueous liquid by removing an aqueous liquid from a well, and rinse and/or clean the tip of the immiscible-fluid-discrete-volume-forming tube. In such embodiments, an immiscible-fluid-discrete-volume-forming (inner) tube can be lowered into a well. When the inner tube is lowered into the well, a pump can discharge fluid from the inner tube into the well. The inner tube can then be withdrawn from the well, by raising the tube individually, by raising the entire apparatus, or by lowering the well. When the inner tube is removed from the aqueous liquid in the well, a solution from outer tube 114 can rinse-off the tip of inner tube 113. For example, oil supplied through outer tube 114 can be used to rinse-off the tip of inner tube 113, and the rinse oil can be removed through a separate channel. As mentioned above, in some embodiments outer tube 114 is not used in the system and rinse fluid can be supplied through block 300 and vacuumed away from the discharge tip of inner tube 113 also through block 300, in which case block 300 can be provided with a rinse fluid supply conduit and a waste removal conduit.

As shown in FIG. 4A, the apparatus can contain aqueous immiscible-fluid-discrete-volumes 304 and non-aqueous spacing fluid 306 in inner tube 113. Aqueous immiscible-fluid-discrete-volumes 304 in inner tube 113 can be pumped to another portion of the system (as indicated by the arrow at the top of the figure) where processing and/or disposal of aqueous immiscible-fluid-discrete-volumes 304 and disposal of spacing fluid 306 can occur, for example, as shown in FIG. 6 and FIG. 5A, respectively. The aqueous immiscible-fluid-discrete-volumes can be discharged into a system for a reaction or hybridization, to a substrate, platform, or container for analysis or further processing, or into a waste container, as deemed appropriate.

The embodiment shown in FIGS. 4A and 4B depicts both an inner tube 113 and an outer tube 114 passing through a through-hole 299 in a block 300. It is to be understood, however, that in some embodiments through-hole 299 itself can serve as the outer conduit or outer tube of the apparatus, and in some embodiments a pump can be operatively connected directly to the through-hole 299.

According to various embodiments and as shown in FIG. 4B, block 300 can comprise a solid block having a through-hole formed therein for inner tube 113 and outer tube 114. The block can be made of any number of different materials. Any suitable material for forming passageways therein for fluids and/or for tubes going through the block can be used. The material should not react or should only very minimally react with any fluids flowing through the material. Exemplary materials for block 300 and for block 308 described below include plastic, polyethyleneterephthalate, polycarbonate, polytetrafluoroethylene, stainless steel, aluminum, glass, and the like. Surfaces of block 300 and block 308 that contact liquids can be coated with an inert, protective, and/or hydrophobic coating. In various other embodiments, block 300 and block 308 can each comprise more than one piece, rather than a monolithic block. As shown in cross-section, block 300 can comprise passageway 301 and tube 302 for directing waste fluids or other fluids to an appropriate location or container. In some embodiments, passageway 301 and tube 302 can be in fluid communication with a pump and a waste container. The direction of liquid flow is shown by arrows in the figure.

Block 300 can have a passageway portion extending therethrough that can permit inner tube 113 and outer tube 114 to pass therethrough. In some embodiments, inner tube 113 can move relative to outer tube 114 and block 300. In various embodiments, the tubes can remain stationary and block 300 can move relative to the tubes. In other embodiments, block 300 can remain stationary and both tubes move relative to block 300. In various embodiments, the arrangement of tubes and block 300 can be moved up and down relative to one or more liquid or sample containers.

In some embodiments, block 300 can be in an "up" position, relative to inner tube 113, as shown in FIG. 4A such that at least inner tube 113 extends beyond the edge of block 300. Alternatively, block 300 can be in a "down" position, relative to inner tube 113, as shown in FIG. 4B such that the end of inner tube 113 does not extend or only minimally extends beyond block 300. The "up" or "down" position can be accomplished either by moving the tubes relative to block 300, or by moving block 300 relative to the tubes.

As shown in FIGS. 4A and 4B, when block 300 is in the "up" position, inner tube 113 can deposit sample liquid 312 into well 313 of sample tray 310. Inner tube 113 can then be withdrawn into outer tube 114 to permit spacing fluid 319 to rinse the tip of inner tube 113.

When block 300 is in a "down" position as shown in FIG. 4B, the pump in fluid communication with inner tube 113 can be shut off, and waste solution can flow through passageway 301 and out waste tube 302. In various embodiments, a pump can be in fluid communication with waste tube 302 in order to pump, for example, air and/or excess oil from outer tube 114, thereby rinsing contaminants, unwanted sample liquid, and/or reagent from end surface or tip 309 of inner tube 113.

According to various exemplary embodiments, tip 309 of inner tube 113 can be placed appropriately to discharge sample liquid 312 in well 313 of sample tray 310. Exemplary sample trays can comprise microtiter plates, picotiter plates, 24-well plates, 96-well plates, 384-well plates, 1536-well plates, 6144-well plates, plates with removable sample vials, a card-type assay device, a flat surface, and array of vials, and the like. The pump that is operatively connected to, and in fluid communication with, inner tube 113 can dispense aqueous liquid through tip 309 and into a well or onto a plate situated thereunder. Tip 309 of inner tube 113 can thereafter be withdrawn from in or near the well or plate. Withdrawal of tip 309 of inner tube 113 can be accomplished either by raising inner tube 113 into outer tube 114, resulting in the illustration shown in FIG. 4B, or by raising the entire apparatus 100 away from the sample.

When inner tube 113 is in the position shown in FIG. 4B, oil or another spacing fluid flowing out of outer tube 114 can rinse-off the end surface or tip of inner tube 113. The spacing fluid used as the rinse liquid can then be directed through passageway 301 in block 300 and be carried away to a waste station (not shown) operatively connected to waste tube 302. In some embodiments, a pump 380 (see FIG. 4A) can be connected to waste tube 302. In various embodiments (not shown) the entire length of passageway 301 can accommodate a tube such that block 300 has a liner therein for passageway 301. The positioning of the tubes relative to block 300 can be accomplished by keeping block 300 in a single position and moving the tubes relative to block 300, or by moving block 300 relative to the tubes, or by a combination of the two types of movements.

As shown in FIG. 4A, in some embodiments a control unit 350 can be provided that can independently control a plurality of pumps 360, 370, 380, for respectively flowing fluids through first conduit 113, second conduit 114, and waste tube 302. Pump 370 can be operatively connected to outer conduit 114 through a tube 121 connected to block 308.

As shown in FIGS. 4A, 4B, 5A, and 5B, apparatus 100 can comprise shroud or block 300 and a second block 308. Block 308 can form a structure that assists in supporting inner tube 113 and/or outer tube 114. Block 308 can comprise a throughhole passageway for inner tube 113 and for outer tube 114, or block 308 can comprise appropriate connections or bores to attach conduits such as capillary tubes to the block. The passageway can comprise an elbow 314 and openings 316 and 320 (See FIG. 5B). It will be recognized that the point of entry of inner tube 113 into outer tube 114 can be sealed to keep the contents of outer tube 114 from leaving outer tube 114 or block 308. Sealing can be accomplished with appropriate boring and/or counter-boring, and/or using a sleeve, bearing, sealing gasket, O-ring, or the like, where appropriate.

According to various embodiments, elbow in block 308 does not necessarily contain outer tubing 114. Instead, outer tubing 114 can be connected to block 308 via an appropriate connection, for example, via a bore 330 in block 308. At opening 320, outer tube 114 can also be connected such that fluid can move from outer tube 114, into block 308, and into tube exiting block 308. Thus, only inner tube 113 actually passes through block 308 in the embodiment depicted.

In order to accomplish a desired result, for example, rinsing the tip of tubes used for discharging volumes of sample liquid, a control unit 350 (see FIG. 4A) can be used for regulating appropriate flow rates and appropriate starting and stopping of the pumps in fluid communication with inner and outer tubes. Such a controller can control an actuator for turning the pumps on and off as desired. The controller can comprise a computer. Appropriate pump speeds and actuations of the pumps can be determined to accomplish the removal of waste from the tip of inner tube 113.

According to various embodiments, a method is provided that comprises: pumping a first fluid in a first direction in a space between an outer perimeter of a first conduit and an inner perimeter of a second conduit; drawing the first fluid past an end surface of the first conduit, and into the first conduit in a second direction that is opposite the first direction; and positioning the first conduit into a receptacle containing a second fluid that is immiscible with the first fluid, and drawing at least a portion of the second fluid past the tip of the first conduit. In some embodiments, the method further comprises, before positioning into the receptacle, positioning at least one of an end surface of the first conduit and an end surface of the second conduit such that the end surface of the first conduit is beyond the end surface of the second conduit. In some embodiments, the method comprises, after drawing at least a portion of the second fluid, positioning at least one of the first conduit and the second conduit such that the end surface of the first conduit can either be flush with the end surface of the second conduit or inside the second conduit. In some embodiments, the second conduit can comprise a block having a through-hole, and positioning at least one of the first conduit and the second conduit can comprise moving the end surface of the first conduit into the through-hole. In some embodiments, the method can further comprise drawing at least a portion of the second fluid past the tip of the first conduit to rinse the end surface of the first conduit with the first fluid.

According to various embodiments, waste, for example, spacing fluid between adjacent sample immiscible-fluid-discrete-volumes, can be removed. As the spacing fluid comes out of the tip 309 of inner tube 113, outer tube 114 can have a suction applied to it and any unwanted spacing fluid sample immiscible-fluid-discrete-volumes can be removed.

Figure 5B:
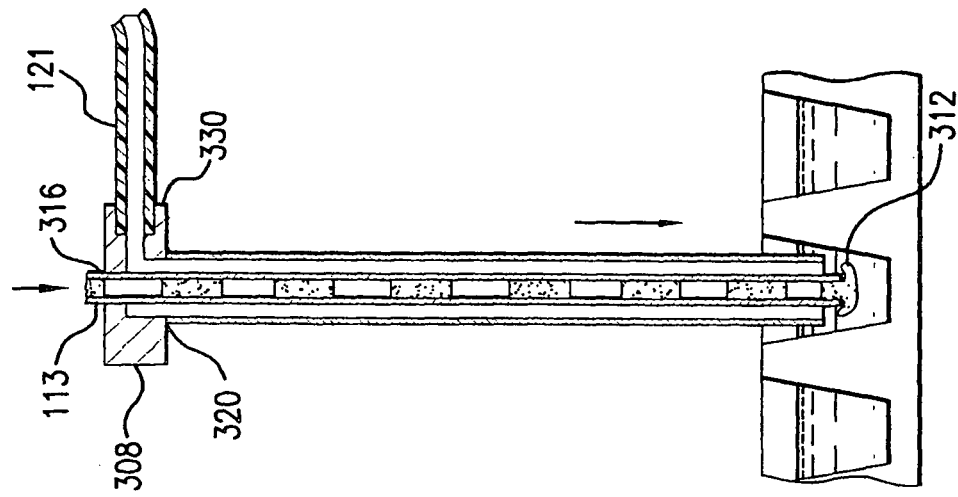
FIG. 5B illustrates a cross-sectional view of using the apparatus to deposit a sample in a sample well, according to various embodiments.
Figure 5A:
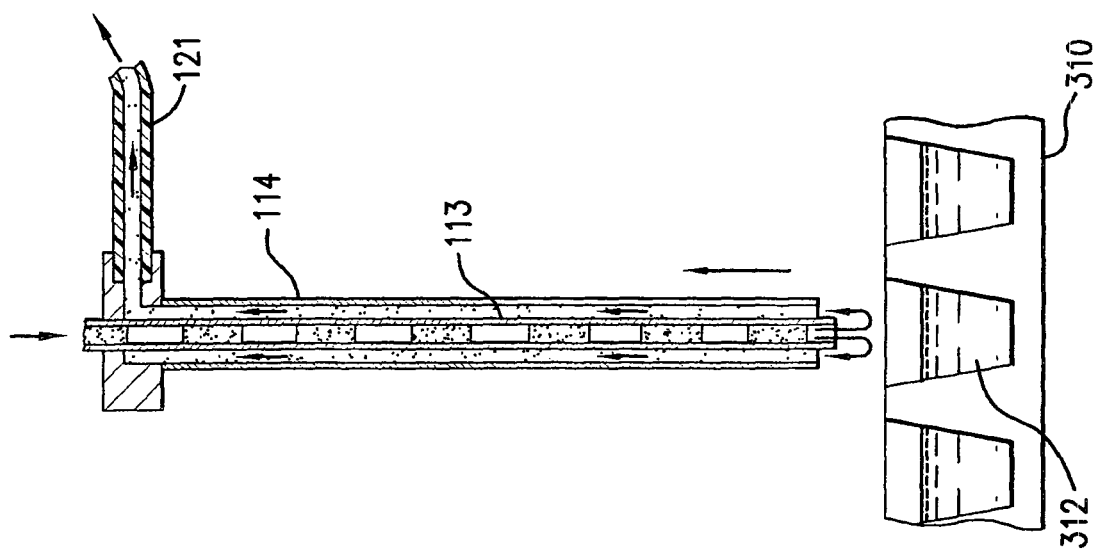
FIG. 5A illustrates a cross-sectional view of removal of waste material, according to various embodiments.
Figure 6:
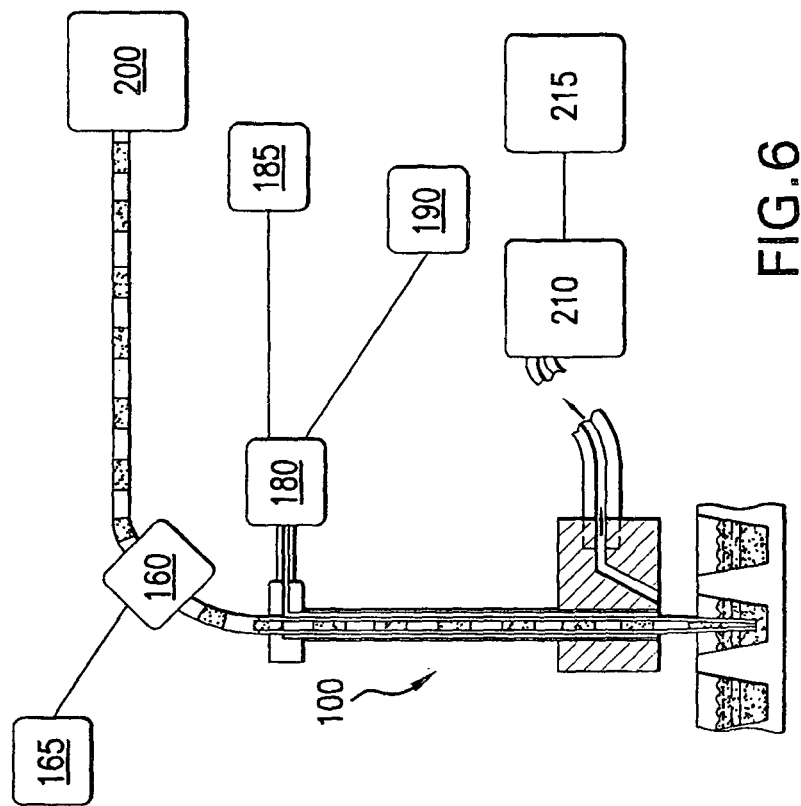
FIG. 6 illustrates a cross-sectional view of a system incorporating an apparatus of FIGS. 4A and 4B to deposit immiscible-fluid-discrete-volumes for downstream sample processing as desired, according to various embodiments.

FIGS. 5A and 5B illustrate an embodiment for removing waste from an inner tube 113 and/or for depositing desired samples in a container. For such a usage the apparatus can be placed at the back-end of a system, such that already prepared immiscible-fluid-discrete-volumes can be "spit out" from the inner tube and waste can be sucked away through the outer tube. In such usage, pumping of immiscible-fluid-discrete-volumes and/or other solutions can occur in different directions than shown in FIGS. 4A and 4B. In various embodiments, the apparatus can first be used to obtain sample immiscible-fluid-discrete-volumes spaced from one another by spacing fluid, and then a similar apparatus on the back-end of the system can have reverse pump directions such that sample immiscible-fluid-discrete-volumes and/or spacing fluid can be "spit out" either collected or sent to a waste receptacle.

In the "up" position shown in FIG. 5A, waste can be sent to a waste container. In the down position shown in FIG. 5B, a desired sample immiscible-fluid-discrete-volume can be deposited in a desired container. In the down position, suction normally being applied to outer tube 114 can be stopped or sufficiently slowed down such that the desired sample immiscible-fluid-discrete-volume can be deposited in an appropriate sample well.

According to various embodiments, the downstream processes can be carried out in a capillary channel, for example, a capillary tube. The capillary tube can be in fluid communication with apparatus 100 as shown in FIG. 6. An exemplary capillary tube that can be used can have an inner diameter of about 1000 microns or less. In other embodiments the inner diameter can be about 300 microns or less, for example, about 100 microns or less, or about 50 microns or less. Other embodiments can involve methods that use a capillary tube having an inner diameter that is greater than about 300 microns, for example, from about 500 microns to about 1000 microns, or about 500 microns or less. In various embodiments, the above dimensions can refer to the maximum cross-sectional dimension of the capillary channel. Such a channel can be rectangular in shape or have any other suitable shape. Various systems and apparatus can also be provided that include such a capillary channel.

FIG. 6 illustrates a system that can use one or more embodiments of apparatus 100. In various embodiments, aqueous immiscible-fluid-discrete-volumes spaced apart by spacing fluid are prepared in apparatus 100. A pump 160, control unit 165, pump 180, control unit 185, spacing fluid source 190, can be used to prepare the aqueous immiscible-fluid-discrete-volumes. The aqueous immiscible-fluid-discrete-volumes can then also be pumped to the rest of the system 200 with pump 160. The rest of the system represented by the black box designated 200 can comprise a system as shown and described in U.S. Provisional Patent Application No. 60/710,167, filed Aug. 22, 2005, which is incorporated herein in its entirety by reference, or any of the immiscible-fluid-discrete-volume processing systems described and shown herein. A pump 210 can be operatively connected to waste tube 208. Pump 210 can be controlled by a control unit 215, and control unit 215 can be operatively connected to one or more other control units in the system.

In some embodiments, a method is provided that can comprise using the system described herein to process an aqueous immiscible-fluid-discrete-volume. According to various embodiments, the method can comprise amplifying at least one target nucleic acid sequence, for example, in a processing conduit downstream of the immiscible-fluid-discrete-volume-forming inner conduit described above. According to various embodiments, the method can comprise introducing polymerase chain reaction inactivating reagents into a processing conduit, for example, a capillary channel, after amplifying the at least one target nucleic acid sequence and before subjecting the nucleic acid sequence to a sequencing reaction. The reagents can be used to inactivate or remove or eliminate excess primers and/or dNTP's resulting from or leftover from an amplification process. The inactivating reagents can be introduced at a junction in the processing conduit, for example, after an aqueous sample immiscible-fluid-discrete-volume to be inactivated is aligned with the junction. The junction can comprise, for example, a T-intersection or a Y-intersection.

According to various embodiments, one or more target nucleic acid sequences can be subjected to a sequencing reaction to form a detectable product, and the method can comprise detecting the detectable product. In various embodiments, the detectable product can be detected inside the same processing conduit or capillary channel where the detectable product is formed. In other embodiments, the detectable product can be transferred out of the processing conduit and detected using, for example, using a flow cell or a capillary electrophoretic sequencer. In various other embodiments, an off-capillary detector can be used as deemed appropriate.

Figure 7:
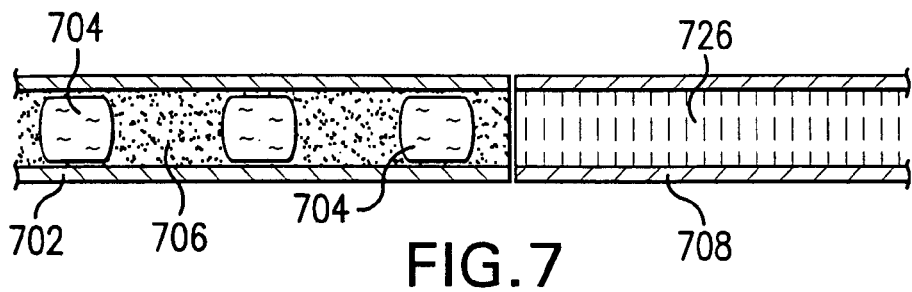
FIG. 7 is a cross-sectional side view of a system comprising the discharge tip of an immiscible-fluid-discrete-volume-containing conduit axially aligned with and adjacent the injection tip of an injector of a capillary electrophoresis capillary, according to various embodiments.

FIG. 7 illustrates the injection of charged analytes from processed immiscible-fluid-discrete-volumes into a downstream, capillary electrophoresis intake tip, according to various embodiments of the present teachings. According to various embodiments as shown in FIG. 7, an immiscible-fluid-discrete-volume output conduit 702 can contain a sequence of aqueous volumes 704, such as liquid samples, separated by spacing fluid 706. Spacing fluid 706 can be, for example, oil or other liquid that is immiscible with aqueous volumes 704. Immiscible-fluid-discrete-volume output conduit 702 can be positioned adjacent, and in contact or abutted with, a capillary electrophoresis capillary 708. Capillary electrophoresis capillary 708 can be filled with separation medium 726, such as acrylamide gel or other separation or sieving medium for separating the contents of aqueous volumes 704 by electrophoresis. According to various embodiments as shown in FIG. 7, aqueous volumes 704 can be generated and/or processed by various techniques described in U.S. Patent Application Publication No. 2007/0062583 A1, which is incorporated herein in its entirety by reference, and be or include biological material such as DNA samples combined with primer and other reagents. According to various embodiments as shown in FIG. 7, aqueous samples 704 can be injected into capillary electrophoresis capillary 708 by direct pressure injection, for instance by closely positioning an output end of immiscible-fluid-discrete-volume output conduit 702 against capillary electrophoresis capillary 708, and applying pressure and/or vacuum to drive and/or pull aqueous samples 704 into the tip of capillary electrophoresis capillary 708 and into separation medium 726. DNA or other sample material of interest can then be separated, identified, sequenced, or otherwise processed by electrophoretic separation in separation medium 726.

Figure 8A:
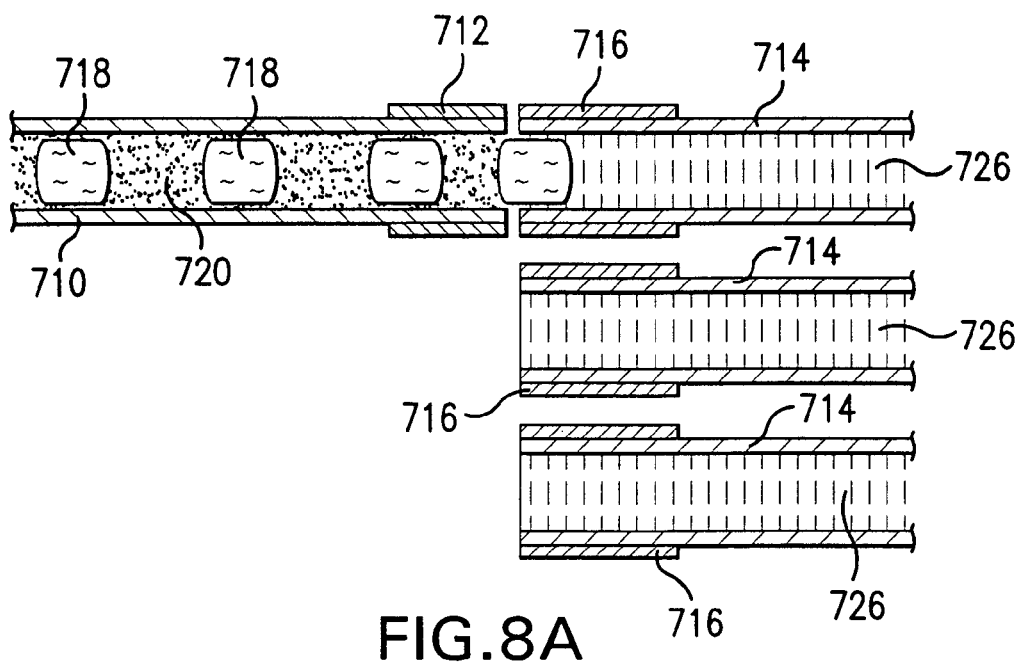
FIG. 8A is a cross-sectional side view of a system comprising the discharge tip of an immiscible-fluid-discrete-volume-containing conduit and three different injection tips of three respective capillary electrophoresis capillaries, according to various embodiments.

As shown in FIG. 8A, according to various embodiments, an immiscible-fluid-discrete-volume output conduit 710 can contain a set of aqueous volumes 718, such as samples, separated by spacing fluid 720, such as oil or other liquid that is immiscible with aqueous volumes 718. According to embodiments as shown in FIG. 8A, the output end of immiscible-fluid-discrete-volume output conduit 710 can be positioned adjacent to, and in contact or abutted with, a set of capillary electrophoresis capillaries 714, each of which is filled with separation medium 726, such as acrylamide gel or other sieving or separation medium. According to various embodiments as shown in FIG. 8A, immiscible-fluid-discrete-volume output conduit 710 can be movably positioned to be axially aligned with a selected one or more of capillary electrophoresis capillaries 714. According to various embodiments, aqueous volumes 718 can be injected into the tip of the respective one of capillary electrophoresis capillaries 714 with which immiscible-fluid-discrete-volume output conduit 710 is aligned. According to various embodiments, injection of aqueous volumes 718 can be performed by pressure injection and/or vacuum.

According to various other embodiments as shown in FIG. 8A, aqueous volumes 718 can be injected into a tip of the respective one of capillary electrophoresis capillaries 714, with which immiscible-fluid-discrete-volume output conduit 710 is aligned, for example, axially aligned, by electrokinetic injection. According to embodiments as shown, immiscible-fluid-discrete-volume output conduit 710 can be provided with immiscible-fluid-discrete-volume conduit electrode 712, while each of capillary electrophoresis capillaries 714 can be provided with capillary electrophoresis capillary electrode 716.

Figure 8B:
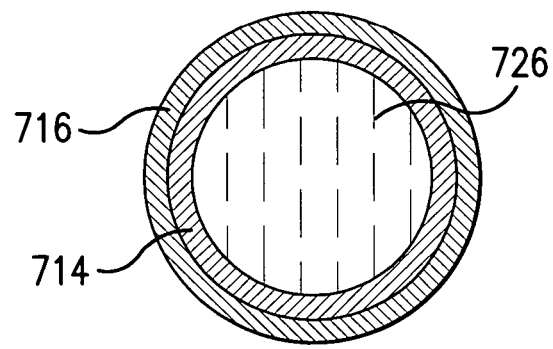
FIG. 8B is an enlarged cross-sectional axial view of an injector of a capillary electrophoresis capillary useful with the systems shown in FIGS. 7 and 8A, according to various embodiments.

As shown in FIG. 8B, capillary electrophoresis capillary electrode 716 can be formed as an annular cladding that surrounds an outer circumference of capillary electrophoresis capillaries 714. According to various embodiments, capillary electrophoresis capillary electrode 716 can be formed by electroplating, vapor deposition, or can be formed as a separate electrode element, such as a sheath fitted to capillary electrophoresis capillaries 714, that again can contain separation medium 726. According to various embodiments, immiscible-fluid-discrete-volume conduit electrode 712 can be formed in a similar or same manner as capillary electrophoresis capillary electrode 716. According to various embodiments, an electric potential can be applied between immiscible-fluid-discrete-volume conduit electrode 712 and an electrode at an opposite end of the capillary electrophoresis capillary relative to the end shown, to perform an electrokinetic injection from aqueous volumes 718 into the respective capillary electrophoresis capillaries 714. According to various embodiments, an electric potential or field can be generated according to other electrode configurations, for example to provide the same or different electric potential between each of immiscible-fluid-discrete-volume conduit electrode 712 and capillary electrophoresis capillary electrode 716 and ground. According to various embodiments, either direct current, alternating current, or a combination of direct and alternating current can be applied to either of immiscible-fluid-discrete-volume conduit electrode 712 and capillary electrophoresis capillary electrode 716. According to various embodiments, one or more than one power supply can be used to apply electric power to immiscible-fluid-discrete-volume conduit electrode 712 and capillary electrophoresis capillary electrode 716.

As shown in FIGS. 7, 8A, 8B, and 9, according to various embodiments of the present teachings, aqueous volumes 734 can be injected from an immiscible-fluid-discrete-volume conduit 728 into a tip of a capillary electrophoresis capillary 736 by electrokinetic injection. According to various embodiments, capillary electrophoresis capillary 736 can contain separation medium 726. In some embodiments as shown, immiscible-fluid-discrete-volume conduit 728 can be provided with immiscible-fluid-discrete-volume conduit electrode 730, while capillary electrophoresis capillary 736 can also be provided with capillary electrophoresis capillary electrode 738.

According to various embodiments, capillary electrophoresis capillary electrode 738 can be formed as an annular cladding that surrounds an outer circumference of capillary electrophoresis capillary 736. In some embodiments, capillary electrophoresis capillary electrode 738 can be formed by electroplating, vapor deposition, or can be formed as a separate electrode element, such as a sheath fitted to capillary electrophoresis capillary 736. In some embodiments, immiscible-fluid-discrete-volume conduit electrode 730 can be formed in a similar or same manner as capillary electrophoresis capillary electrode 716. According to various embodiments, an electric potential can be applied between immiscible-fluid-discrete-volume conduit electrode 730 and a capillary electrophoresis capillary electrode at an opposite end of the capillary relative to the end where electrode 738 to perform an electrokinetic injection from aqueous volumes 734 into capillary electrophoresis capillary 736. In some embodiments, other electrode configurations can be used, for example to provide the same or different electric potential between each of immiscible-fluid-discrete-volume conduit electrode 712 and capillary electrophoresis capillary electrode 716 and ground.

According to various embodiments, either direct current, alternating current, or a combination of direct and alternating current can be applied to either of immiscible-fluid-discrete-volume conduit electrode 712 and capillary electrophoresis capillary electrode 716 from one or more than one electric power supply.

In some embodiments, each of electrodes 712, 730, 740, and 760, for example, can independently comprise a pin electrode.

Figure 9:
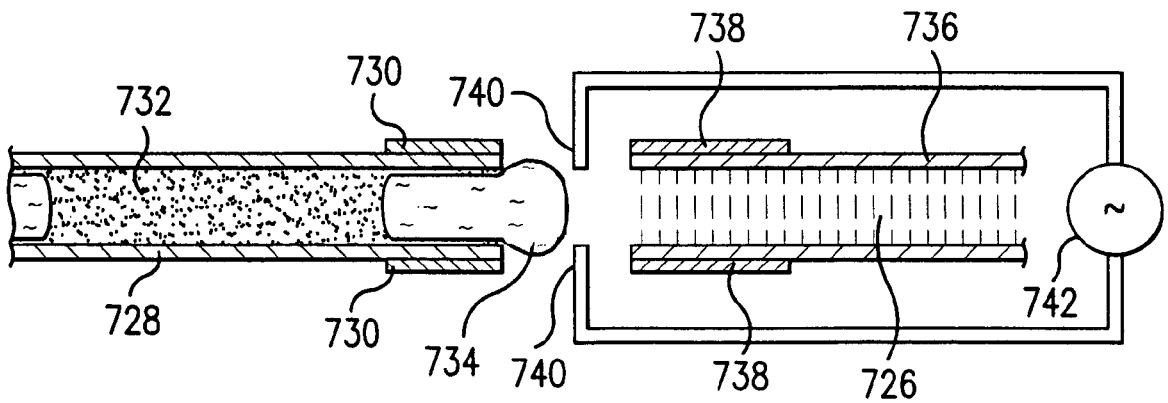
FIG. 9 is a cross-sectional side view of a system comprising the discharge tip of an immiscible-fluid-discrete-volume-containing conduit axially aligned with and adjacent a dielectrophoresis device and arranged for processing of a discrete volume with the dielectrophoresis device, according to various embodiments.

According to various embodiments as shown in FIG. 9, the injection of aqueous volumes 734 can likewise be augmented by dielectric concentration. More specifically, according to embodiments as shown in FIG. 9, electrodes 740 can be provided in a generally opposed configuration near the intake tip of capillary electrophoresis capillary 736. According to various embodiments, electrodes 740 can be electrically connected to a power supply 742 that delivers alternating current at the tip area of capillary electrophoresis capillary 736 to induce a dielectrophoretic effect acting on aqueous volumes 734. According to embodiments of the present teachings in this regard, the salt concentration and other properties of aqueous volumes 734 in immiscible-fluid-discrete-volume conduit 728 resulting from cycle sequencing, polymerase chain reaction (PCR), or other processing can be maintained without adversely affecting the amount of aqueous volumes 734 injected into capillary electrophoresis capillary 736. According to various embodiments as shown in FIG. 9, dielectric concentration can be achieved by maintaining immiscible-fluid-discrete-volume conduit 728 and capillary electrophoresis capillary 736 in axial alignment in close proximity as shown, and maintaining most of the emerging volume or slug of aqueous volumes 734 in immiscible-fluid-discrete-volume conduit 728. An AC electric field can then be applied via electrodes 740 to concentrate DNA or other material of interest in the emerging volume of aqueous volumes 734 by dielectrophoretic action. Better separation, detection and other electrophoresis characteristics can in one regard thereby be achieved. In some embodiments electrodes 730 and 738 can be used to perform concentration, rendering electrode 740 optional.

According to various embodiments as shown in FIGS. 10A and 10B, the injection of aqueous volumes 754 can similarly be augmented by dielectric concentration, and also enhanced by introducing a delay before injection. More specifically, according to embodiments as shown in FIG. 10A, electrodes 760 can be provided in a generally opposed configuration near the intake tip of capillary electrophoresis capillary 756. Capillary electrophoresis capillary 756 can be provided with electrodes 758, for example, annular electrodes for electrokinetic injection. Capillary electrophoresis capillary 756 can be generally aligned, for example, axially, with an immiscible-fluid-discrete-volume conduit 750 in which aqueous volumes 754 can be contained, separated by spacing fluid 756, such as oil or other liquid. According to various embodiments, electrodes 760 can be electrically connected to a power supply 762 that delivers alternating current at the tip area of capillary electrophoresis capillary 756 to induce a dielectrophoretic effect acting on aqueous volumes 754. According to embodiments of the present teachings in this regard, the salt concentration and other properties of aqueous volumes 754 in immiscible-fluid-discrete-volume conduit 750 resulting from cycle sequencing, PCR, or other processing can be maintained without adversely affecting the amount of aqueous volumes 754 injected into capillary electrophoresis capillary 756.

According to various embodiments as shown in FIG. 10A, dielectric concentration can be achieved by maintaining immiscible-fluid-discrete-volume conduit 750 and capillary electrophoresis capillary 756 in axial alignment in close proximity as shown, and maintaining most of the emerging volume or slug of aqueous volumes 754 in immiscible-fluid-discrete-volume conduit 750. According to embodiments as shown in FIG. 10A, the emerging volume of aqueous volumes 754 can be maintained in the interstitial area between immiscible-fluid-discrete-volume conduit 750 and capillary electrophoresis capillary 756 for a predetermined period of time, to effect diffusion of DNA or other sample material in the emerging volume. The time period can be after dielectrophoretic concentration, which brings all the small and large molecules of DNA initially together. At a period of time shown in FIG. 10A, smaller DNA molecules or fragments, ions, or other material can be intermingled with larger and slower DNA molecules and other heavier, larger, or slower fragments in the emerging aqueous volume. A period of time, for example, on the order of several seconds, or more or less time, can be permitted to elapse. After the delay, the components of the emerging volume of the aqueous volumes 754 migrate or diffuse to separate regions, leaving primarily larger, slower DNA molecules or fragments, larger ions, or other larger, heavier, or slower components grouped closer together at the leading edge of the emerging aqueous volume. As shown in FIG. 10B, an AC electric field can then be applied via electrodes 760 to concentrate DNA or other material of interest in the emerging volume of aqueous volumes 754 by dielectrophoretic action, for example, before diffusion caused by electrokinetic injection. The dielectrophoretic action applied to an aqueous volume whose components have already partially separated by diffusion, even further improved separation, detection and other electrophoresis characteristics can in one respect thereby be achieved. After dielectrophoretic concentration, the sample can be injected by electrokinetic injection.

As shown in FIG. 10C, an aqueous volume is emerging into a gap between conduit 750 and capillary 756. In some embodiments, electrodes can be disposed in the gap. In some embodiments, electrodes 770 can penetrate the wall of conduit 750 and electrically connect to an annular, two-part, ring electrode inside conduit 750. Electrodes 760 can be configured close to capillary electrophoresis capillary 756, but without a necessity that the emerging aqueous volume of aqueous volumes 754 be maintained in immiscible-fluid-discrete-volume conduit 750. According to embodiments as shown, the gap between immiscible-fluid-discrete-volume conduit 750 and capillary electrophoresis capillary 756 can be configured as a cross channel, into which spacer fluid 756, and most of the emerged immiscible-fluid-discrete-volume, can be removed and flowed away prior to and/or during the injection process. Concentrated charged analytes can migrate into capillary electrophoresis capillary 756 and consequently avoid being washed away. According to various embodiments, the cross channel can also receive a wash solution to clean the tips of immiscible-fluid-discrete-volume conduit 750 and/or capillary electrophoresis capillary 756. Discussion of injection across a gap as illustrated can be found, for example, U.S. Pat. No. 5,110,431 to Moring et al. and U.S. Pat. No. 5,798,032 to Khan et al., each of which is incorporated by reference in its entirety herein.

In some embodiments, electrodes 712, 716, 730, 738, 770, 752, 758, and the like can be formed by vapor deposition, for example, to coat the end surface of the respective conduit or capillary, and in some cases, to form an electrode coating on an inner surface thereof.

According to various embodiments in another regard, if the emerging aqueous volume is small enough, such that the injected aqueous volume does not significantly increase the size of a detected peak after electrophoresis, the injected aqueous volume can be directly injected into capillary electrophoresis capillary 756 by direct pressure injection, by pushing the aqueous volume into capillary electrophoresis capillary 756 from immiscible-fluid-discrete-volume conduit 750 positioned adjacent thereto. According to various embodiments in another regard, if the emerging aqueous volume if large enough to adversely affect detected peak size after electrophoresis, dielectrophoretic concentration can be performed in capillary electrophoresis capillary 756, as for example described in U.S. Pat. No. 6,537,433 to Bryning et al, which is incorporated herein by reference in its entirety. According to embodiments of the present teachings in another regard, if the salt concentration is determined to be high in aqueous volumes 754, deionized water can be added to aqueous volumes 754 to reduce salt concentration. According to various embodiments in a further regard, a di-electrophoretic concentration can be performed at the end of immiscible-fluid-discrete-volume conduit 750, prior to pressure injection or electrokinetic injection into capillary electrophoresis capillary 756.

As illustrated in FIG. 11, a sample can be deposited on electrically conductive surface 1108 of a sample apparatus 1120. Sample apparatus 1120 can comprise substrate 1104, and a layer 1102 that can make-up, in whole or in part, electrically conductive surface 1108. In various embodiments, substrate 1104, itself, can be the electrically conductive material, for example, gold that can have electrically conductive surface 1108. In other embodiments, a coating or thin layer 1102 of electrically conductive material can form or be part of the conductive surface.

In some embodiments, an electrically conductive surface is provided that is coated with a hydrophobic material, for example, a fluoropolymeric material, in regions where it is desired to avoid wetting-out or hydrophilic attraction of aqueous sample drops or volumes. In some embodiments, the surface can be generally hydrophobic except in areas spotted with a gold surface material, such that separated electrically conductive spots or regions can be independently controllable, that is, such that the different spots can be independently made to be in electrical communication with a voltage source. In some embodiments, a grid, array, or other grouping of spots, regions, areas, or other locations can be provided on a surface wherein electrical potentials can be independently applied to the spots. In some embodiments, a potential can be applied to some spots while not being applied to other spots.

In some embodiments, such an array of spots or locations, whether independently controllable or not, can be arranged in the same shape and with the same spacing as the injector tips of an injector array of a processing device, for example, to interface with the injector tips of a multi-capillary capillary electrophoresis apparatus. In some embodiments, liquid drops corresponding to immiscible-fluid-discrete-volumes deposited on an electrically conductive surface can be arranged on the surface in an array that can interface with an injector of a two-capillary, four-capillary, eight-capillary, 16-capillary, 48-capillary, or 96-capillary capillary electrophoresis apparatus. For example, immiscible-fluid-discrete-volumes to be further analyzed can be deposited in an 8 by 12 array corresponding to the footprint of a standard 96-well microtiter plate, and all 96 volumes can be simultaneously electrophoretically injected into a 96-capillary capillary electrophoresis apparatus, for example, a 3730xl multi-capillary electrophoresis analyzer available from Applied Biosystems, Foster City, Calif.

The independently controllable electrically conductive spots and/or the arrangement of volumes in an array, as described above, can also be implemented in various other embodiments of the present teachings, including, for example, the embodiments shown in FIGS. 2, 3, 12-18, 22A, and 22B.

Electrically conductive surface 1108 can receive sample from end or tip 1186 of processing channel 1140. The samples can be prepared in a sample preparation device that is in fluid communication with conduit 1140. In various embodiments, conduit 1140 can be a capillary tube. Other types of conduits, however, can also be used. Discrete volumes 1130, for example, of a processed aqueous sample, are disposed in conduit 1140 and are spaced apart by spacing fluid 1132, as described herein. The discrete volumes 1130 can be prepared in sample preparation device (See, FIGS. 1A and 1B for additional details) and can be deposited or dispensed onto electrically conductive surface 1108 from tip 1186. In various embodiments, electrically conductive surface 1108 can comprise, for example, an electrically conductive film or an electroplated layer of a conductive material.

According to various embodiments, sample apparatus 1120 can comprise an identifier 1114, for example, a bar code, RFID or other identifying label, tag, or indicia. The identifier can assist in quality control or inventory of sample apparatus 1100 or can be used for keeping track of samples deposited on sample apparatus 1100. The identification can be machine readable.

According to various embodiments, electrically conductive surface 1108 can be covered with an insulating layer. In such an embodiment, substrate 1104, electrically conductive surface 1108 and the insulating surface can act as a capacitor. A sample dispensed onto the surface of substrate 1104 can be injected into a conduit, capillary tube, or channel from the insulating layer when the substrate acts as a capacitor.

Discrete volumes 1130 comprising samples of interest and spacing fluid 1132 can be pumped from tip 1186 onto electrically conductive surface 1108. The spacing fluid can comprise an oil or other liquid that allows the spacing fluid to provide a spacing or partitioning portion between adjacent aqueous immiscible-fluid-discrete-volumes. The immiscible-fluid-discrete-volumes can be dispensed onto electrically conductive surface 1108 in a controlled pattern or manner, for example, a zig-zag or raster pattern. In various embodiments, alternating spots deposited from tip 1186 of conduit 1140 can comprise aqueous sample spots alternating with spacing fluid spots deposited on electrically conductive surface 1108. In other embodiments, a plurality of spots on electrically conductive surface 1108 can be aqueous sample spots. In some embodiments, the plurality of spots can all comprise aqueous sample spots, if, prior to deposition on electrically conductive surface 1108, the spacing fluid is diverted to a waste container (See, FIGS. 1A, 1B, and 12 for additional details). In some embodiments, the aqueous sample spots can be deposited in an array adapted to interface with an injector array of an analyzer, for example, a capillary electrophoresis apparatus. In some embodiments, plural aqueous sample spots can be combined together into a larger spot, for example, combined in a well, and a multiplexing capillary electrophoresis analysis can then be performed on the larger spot.

Conduit 1140 can connect to and can be controlled by sample collection device drive arm 1194 and conduit holder 1184 that can together position tip 1186 in a first position, a second position, or additional positions. Control drive arm 1194 and drive unit 1196 can be controlled, for example, by a computer in order to move conduit 1140 in an X and/or Y and/or Z direction, as deemed appropriate.

As illustrated in FIG. 12, where reference numerals that are the same as in FIG. 1 represent like components, aqueous sample discrete volumes 1130 separated by spacing fluid 1132 can be prepared using an immiscible-fluid-discrete-volume sample preparation device 1267, or as described, for example, in connection with FIGS. 1A and 1B herein. In the simplified illustration shown in FIG. 12, sample preparation device 1267 can comprise an aqueous sample injection unit 1274, a spacing fluid injection unit 1276, conduits 1229 and 1231, and conduit junction 1242. Sample injection units 1274 and 1276 can comprise, for example, pumps. Sample preparation device 1267 can comprise a control unit 1266, for example, comprising a computer, adapted to flow aqueous sample 1130 and spacing fluid 1132 from their respective injection units. Control unit 1266 can be adapted to inject volumes of aqueous solution and spacing fluid to form immiscible-discrete-volumes of the aqueous sample in conduit 1140. In various embodiments, control unit 1266 can merely control a conduit junction, for example, junction 1242, or it can control a rotary valve or other valve, and pumps, as described herein. Control unit 1266 can comprise a computer that can be adapted to regulate injection units 1276 and 1274.

According to various embodiments, slugs or other discrete volumes of the aqueous sample can be prepared at a junction by applying a fixed pressure to aqueous sample and spacing fluid that are in conduits 1229 and 1231, respectively. Discrete volumes of the aqueous sample can form with a size and speed that is a function of the conduit, junction diameter, pressure for each fluid, and/or viscosity of each fluid.

Discrete volumes of the aqueous sample can be formed by pumping spacing fluid and aqueous sample into conduits 1230 and 1232, respectively. The non-aqueous spacing fluid can comprise an oil, for example, a fluorocarbon oil. Non-aqueous spacing fluid 1231 is pumped from spacing fluid injection unit 1276 into conduit 1230 and aqueous sample 1229 is pumped from pump 1274 into conduit 1232. Pumps can comprise servomotors, syringes, piston pumps, and/or the like. A valve, for example, valve 1235 can be inserted into the system to regulate flows of liquids. Additional valves can be inserted into the system as deemed appropriate. In various embodiments, the aqueous sample does not necessarily comprise a sample because the sample can be added through inlet ports downstream from junction 1242, and instead, the liquid designated 1229 can comprise another aqueous liquid, for example, containing reactants to react with an aqueous sample downstream.

According to various embodiments, a nucleic acid sample can be amplified, for example, a DNA sample, to form amplicons, in a thermo-cycler 1250. In various embodiments, aqueous slugs 1230 comprising a DNA sample can be amplified in thermo-cycler 1250 along a section of conduit 1140. Coiling of conduit 1140 in thermo-cycler 1250 is merely represented as a section of the conduit that can be used for thermal cycling. Coiling is not mandatory and any arrangement adapted for thermocycling can be used. Other arrangements of conduit 1140 can serve equally well to regulate the temperature of the discrete volumes during reactions. In various embodiments, a length of conduit 1140 can be an integral part of thermo-cycler 1250.

Valve 1235 can control flow to thermo-cycler 1250. Such valves, however, can be used elsewhere in the system as deemed appropriate. The temperature of thermo-cycler 1250 can be maintained or changed as deemed appropriate using a temperature controlled environment (not shown). The temperature controlled environment can be produced by direct contact of the thermo-cycler 1250. In various embodiments, the temperature controlled environment can be produced indirectly. In other words, by not making direct contact with thermo-cycler 1250, for example, with an incubator, oven or refrigerator. Thermal regulation of the contents of conduit 1140 shown in thermo-cycler 1250 can be used in any process or method that requires temperature control of samples in partitioned volumes, for example, in PCR. Additional variations of the system for sample preparation, thermal cycling and slug preparation can be found in U.S. Provisional Patent Application No. 60/710,167 entitled "Sample Preparation for Sequencing" to Lee et al., filed Aug. 22, 2005, which is incorporated herein in its entirety by reference.

During thermocycling, or at other times in the method, or at various locations in the system, an intercalating dye, for example, SYBR green can be added to a reaction mixture in aqueous immiscible-fluid-discrete-volumes 1230. Alternatively, the dye can be added before sample addition to the aqueous slugs. After thermocycling, the aqueous slugs comprising SYBR green can exhibit increased fluorescence due to the intercalating dye, that is, intercalation of the dye can provide an indication that the PCR was positive, which can in turn indicate that a target molecule was present and amplified. Lack of the intercalated dye and/or fluorescence can be used as a basis for excluding an aqueous immiscible-fluid-discrete-volume from the next step in a process, thereby saving expensive consumable reagents.

Referring again to FIG. 12, selected discrete volumes can be dispensed onto sample apparatus 1200. As shown, thermo-cycler 1250 can connect downstream to a sample collection device drive arm 1194. Drive arm 1194 and conduit holder 1184 can together position conduit tip 1186 in a first position, a second position, and/or additional positions and provide movement in the X and/or Y and/or Z direction. Drive arm 1194, conduit holder 1184, and drive unit 1196 can together comprise components of a collection device 1241. Collection device 1241 can further comprise an excitation source 1260 and a detector 1295 that can provide control signals to control drive arm 1194 and drive unit 1196. Excitation source 1260 can comprise, for example, any of a variety of illumination sources if detector 1295 comprises a spectrophotometric detector. Detector 1295 can comprise, for example, a photomultiplier tube (PMT), photodiode, and/or a charge coupled device (CCD), or the like. Detector 1295 can serve several functions, for example, it can assist in determining where samples have been dispensed onto sample apparatus 1200. In various embodiments, detector 1295 can interact with or control a discriminating device 1262 that enables unwanted samples to be diverted to a waste container and can control placement of samples into desired locations on the plate. Unwanted samples can be aspirated, for example, through tube 1264 of discriminating device 1262, and sent to a waste collector of discriminating device 1262.

At a first position, tip 1186 of conduit 1140 can be positioned so that discrete volumes expelled therefrom can be dispensed onto electrically conductive surface 1272 of sample apparatus 1200. Additional details of sample apparatus 1200 can be seen in FIG. 11 in connection with the description of sample apparatus 1120.

At a next position, the process is repeated and another spot is dispensed. According to various embodiments, sample apparatus 1200 can be moved by carriage unit 1290 and drive unit 1292 relative to conduit 1140 and/or tip 1186 thereof. As such, a desired pattern of dispensed sample can be provided. In some embodiments, sample apparatus 1200 can be moved by carriage unit 1290 and drive unit 1292 for further processing of the dispensed samples.

According to various embodiments, the system can be used in a method that can comprise denaturing an attached double-stranded amplicon to form an attached single-stranded amplicon prior to detecting the attached amplicon or an attached derivative thereof, in the at least one conduit. In various embodiments, the method can comprise reacting the attached single-stranded amplicon with a label prior to detecting the attached amplicon or an attached derivative thereof, in at least one conduit. The label can comprise a fluorescent or reporter dye, an intercalating dye, a radioactive label, a nano-barcode label or another type of marker. An intercalating dye can comprise, for example, SYBR green and can be used to identify whether or not a slug comprises a nucleic acid sequence. In various embodiments, a label can be used to detect an amplicon, reaction products other than an amplicon, or other reagents used in the methods and systems.

According to various embodiments, target samples can be prepared comprising, for example, A and B primers, SYBR green dye and a polymerase. The target samples can be diluted by limiting dilution to a single molecule per given volume. SYBR green, as well as other dyes known in the art can be used, as deemed appropriate, at various times in the process in order to generate a fluorescent signal to be detected. SYBR green and other dyes can produce a change in fluorescent signal upon interacting with double-stranded nucleic acids, thereby permitting the quantitative or qualitative detection of an amplicon in a slug of interest. Such information about the presence, absence, or quantity of an amplicon in a slug can be used to determine if further analysis of the slug is desired. Target samples can be loaded into a conduit in the form of aqueous slugs that are separated from one another by oil slugs. An amplification of target samples can occur within aqueous slug 1130 in a thermo-cycler 1250. In various embodiments, after flowing from thermo-cycler 1250 following amplification, the target samples can be flowed past a detector. In order to avoid unnecessary waste of expensive reagents, target samples can be flowed past a detector at one or more of several different points in the system and if sample is not present (for example, as indicated by lack of SYBR green fluorescence), the slugs can be diverted to a waste container. Examples of such diversion systems can be found in more detail in the U.S. Provisional Patent Application No. 60/710,167 entitled "Sample Preparation for Sequencing" of Lee et al., filed Aug. 22, 2005, incorporated in its entirety herein by reference. Those aqueous slugs comprising an amplified target sample, for example, those samples fluorescing due to incorporation of SYBR green, can be collected for further processing, while those slugs that do not fluoresce can be sent to a waste collection. Similarly, slugs containing amplicons derived from more than one template can also be sent to waste collection or otherwise prevented from being subjected to unnecessary further analysis. Further processing can comprise, for example, depositing each individual aqueous slug onto surface 1272, and/or performing cycle sequencing reactions. Diversion of sample can occur, for example, prior to thermal-cycler 1250, after thermal-cycler 1250, and/or proximal to tip 1186.

Similar to the embodiments shown in FIGS. 11 and 12, sample can be dispensed into channels in a sample device 1304, as illustrated in FIG. 13. The channels can comprise moieties that bind nucleic acids of interest. Once samples are bound to the surface of the channel, a desired reaction can be performed while maintaining the samples of interest at a given position in the channel, and/or a wash or rinse can be performed. In some embodiments, a top cover can be disposed on the top of sample device 1304 so that an enclosed channel can be formed through which, for example, a rinse fluid can flow, for example, under pressure. A reaction mixture can be introduced into the sample collection device through inlet port 1300 which can be in fluid communication with a channel 1306. The mixture can be washed out through outlet port 1302 which is also in fluid communication with channel 1306. Location of the desired reactive products can be determined by, for example, fluorescence and the samples can be injected into a conduit for the use in step "C" of the process, as shown in FIG. 14.

FIG. 15 is a simplified illustration of a generalized method for analyzing sequencing products deposited on a substrate. In "A," amplified nucleic acids can be deposited from a conduit in a controlled fashion, for example, in a rastered pattern, onto a substrate. This deposition of amplified nucleic acids continues at "B." At "C," samples can be detected with a detector 1500 and at "D" the samples can be moved from the electrically conductive surface of a substrate into conduits for further processing or analysis, for example, by capillary electrophoresis. Intermediate steps, for example, a rinse step, can be performed and/or an injection fluid can be introduced. This can occur when a relative potential is provided to the electrically conductive surface, for example, a negative charge to the surface, and a positive charge to the end of the capillary electrophoresis tube, as illustrated in "D".

According to various embodiments, the positions or locations of sequencing products on other samples of interest on the substrate can be identified by their fluorescence. If fluorescence is observed, then binding of the DNA to the substrate has occurred and a conduit can be positioned immediately adjacent to the sequencing product as indicated at "C." A circuit can be completed between the substrate and the conduits, for example, by liquid or a gel being applied to the substrate. An exemplary liquid can comprise an injection fluid as described herein. In various embodiments, the circuit can be completed by small amounts of gel that can be extruded from the conduit of a capillary electrophoresis apparatus, that makes contact with the substrate, for example, as a conduit is heated, as shown in FIG. 16. An electrical potential can be applied to the substrate and sequencing products can be electrokinetically injected into the conduits.

FIG. 16 illustrates an enlarged view illustrating sequencing products migrating from the electrically conductive surface into a conduit 1600 filled with an electrophoretic separation medium 1602, after a potential has been applied to the conductive surface. The conduit can be part of a capillary electrophoretic analyzer. In various embodiments, for example, an ABI 310, ABI 3130, ABI 3130xl, ABI 3700, ABI 3730, or ABI 3730xl capillary electrophoretic analyzer (available from Applied Biosystems, Foster City, Calif.) can be used for sequencing the products being injected in to the conduit.

According to various embodiments, samples from the conduit as shown, for example, in FIG. 11 or 12, can be deposited on the substrate in a deliberate pattern with respect to the surface on which the samples are being deposited. Relative motion between the conduit and the surface can be achieved by maintaining the surface stationary and moving the conduit or, alternatively, keeping the conduit stationary while moving the surface, or moving both.

According to various embodiments, a carrier can support the substrate and is mounted for reciprocating motion with respect to the conduit to form one axis of a raster. Of course, the substrate can be fixed with the conduit arranged to sweep across the substrate in a raster patter. A propulsion system can generate forces for moving the carrier to a position. A servo system responsive to an output signal can be provided for commanding the propulsion system to move the carrier at a substantially constant speed in a given region or throughout the entire substrate. In some embodiments, an open-loop stepper motor system can be used. A control system responsive to the output signal can be provided to modulate a sample deposition period reciprocally to carrier speed to achieve substantially constant movement per sample. The speed of movement of the carrier relative to the conduit can be adjusted to take into account removal of unwanted discrete-volumes and spacing fluid to a waste receptacle. In various embodiments, if the carrier is moved relative to a stationary conduit tip 1186, it may not be necessary to also have various components of the collection device, for example, drive unit 1196.

According to various embodiments, a position sensor, which is monotonic and repeatable, can include, but is not limited to, a counting position encoder, optical encoder, magnetic encoder, or a capacitive encoder. The propulsion system can comprise a motor, voice coil, a galvanometer, a gas jet or a graphite piston in a glass cylinder powered by a gas or liquid.

According to various embodiments, PCR products or sequencing reaction products can be analyzed by capillary electrophoresis as described in U.S. Pat. No. 5,891,313 to Johnson et al., which is incorporated herein in its entirety by reference. Sequencing reaction products injected from a sample apparatus can be analyzed in a sieving or non-sieving medium. Sequencing reaction products can also be analyzed by using a capillary electrophoresis protocol in an ABI PRISM™ 310 genetic analyzer, or by separating bands of analytes on a 4.5%, 29:1 acrylamide:bis acrylamide, 8 M urea gel prepared for an ABI 377 Automated Fluorescence DNA Sequencer, or in a higher throughput florescence-based automated capillary electrophoresis instruments such as the ABI 3100, ABI 3700, and ABI 3730xl (all available from Applied Biosystems, Foster City, Calif.). Sequence data can be analyzed with Gene Sum GENESCAN® Software from Applied Biosystems.

According to various embodiments, genotyping can be carried using the systems and methods described herein, for example, genotyping as described in Wenz, H. et al. (1998) *Genome Res.* 8:69-80, which is incorporated herein in its entirety by reference.

FIG. 14 provides a simplified illustration showing attachment of an amplicon to the electrically conductive surface, for example, a gold or gold-coated surface. An amplicon can be deposited or dispensed onto a surface as illustrated at "A" and "B." Further details of the process are provided in FIG. 14 at "C" to "G." A double-stranded amplicon comprising a thiol group can bind to the gold surface through the thiol linkage as illustrated at "C." The double stranded amplicon is denatured (as illustrated at "D") and sequence primer is added as illustrated at "E" such that a sequence reaction can be conducted as illustrated at "F." This can occur at each of the spots illustrated at "G." Once the reactions are completed, the products can be washed and dried and then injected as shown in FIGS. 15 and 16. Alternatively, or in addition, washing, rinsing, and/or drying of the surface can be done at other times in the process as deemed most appropriate by those of skill in the art. In various embodiments, rather than having a thiol linkage between DNA and the substrate, other methods of attachment to the substrate can be used. For example, either a biotin or strepavidin molecule can be attached to the electrically conductive surface and the corresponding linker pair can be attached to the terminus of the nucleic acid molecule to be attached to the substrate.

FIG. 17 illustrates aqueous-sample-discrete-volumes 1706, spaced-apart from one another by spacing fluid 1704, flowing down a conduit 1702. Conduit 1702 can comprise an electrically conductive surface and the slugs can comprise samples that can be bound to the surface. The samples can then be washed and subjected to sequencing reactions after which the slugs can be electrokinetically injected or electrically migrated into, for example, capillary electrophoresis injector 1700 when an electric potential is applied between the electrically conductive surface and the end of the tube opposite the end shown.

According to various embodiments, the method can comprise subjecting an attached amplicon or sets of attached amplicons to a sequencing reaction. Exemplary sequencing reactions can comprise a stepwise sequencing reaction, a forward/reverse, reverse/forward sequencing reaction, or a Sanger cycle-sequencing reaction. In various embodiments, reverse/forward or forward/reverse sequencing can comprise reactions with at least one polynucleotide primer.

According to various embodiments and as illustrated in FIG. 18, an electro-wetting manipulation system 1800 is provided and comprises an electro-wetting plate 1802 on which a processed droplet 1804 can be manipulated and moved by electro-wetting action to a pick-up location 1828 on electro-wetting plate 1802. Drop 1804 can be made to traverse a transfer pathway 1808 moving from one independently controlled electro-wetting location or spot 1810 to another through an appropriate application of potential to the spots 1810 controlled by an electro-wetting pathway control unit 1822. While a single pathway 1808 is shown, it is to be understood that a variety of pathways are provided on electro-wetting plate 1802 such that a drop can be moved to any of a number of pick-up locations 1812, 1814, 1816, 1818, and 1820. At pick-up location 1828, drop 1804 can be taken up into an injector of a capillary electrophoresis apparatus.

Deposition on electro-wetting plate 1802 can occur through a distal discharge tip 1826 of an immiscible-fluid-discrete-volume-forming conduit 1824. In some embodiments, drop 1804 comprises the output of an immiscible-fluid-discrete-volume processing conduit as described herein. In some embodiments, a number of drops 1804 can be brought from a single or multiple output conduits to a number of points or locations and the points or locations can correspond to the spacing of a 96-well or 384-well microtiter plate, or, for example, to be lined-up with an injector array of a capillary electrophoresis apparatus. In some embodiments, the points or locations can comprise a gold surface so that thiol chemistries as described herein, can be performed. Optionally, reagent supply locations can also be provided on the surface of the plate so that reagents, if needed, can be moved into appropriate positions by electro-wetting forces.

Further details about generating such a voltage gradient and the manipulation of fluid droplets by electro-wetting can be found, for example, in U.S. Pat. No. 6,629,826 B2 to Yoon et al., which is incorporated herein in its entirety by reference.

In some embodiments, all drop moving or transfer, on electro-wetting plate 1802, can be done under an oil or spacing fluid overlay. Alternatively, a cover can be implemented at a small fixed distance spaced from the electro-wetted surface such that the use of oil can be eliminated and greater accuracy can be achieved. In some embodiments, each transfer pathway can optionally be washed or rinsed between a fluid manipulation process. In some embodiments, two or more dropl or portions can be transferred from two or more locations, and merged together, for example, at pick-up location 1828, so that a combination of drops can simultaneously be injected, for example, into a capillary electrophoresis capillary injector.

In some embodiments, the methods, apparatuses, and/or systems to provide the extraction or collection of samples contained in immiscible-fluid-discrete-volumes within a conduit, for example, a tube, capillary, channel, open channel, or other conduit, without the need to eject individual imrnmiscible-fluid-discrete-volumes from the conduit, are provided. The methods, apparatuses, and/or systems can use migration properties of DNA molecules or other charged analytes in the presence of applied electric fields. For example, the methods, apparatuses, and systems can use electrophoretic properties to achieve sample collection or extraction. In various embodiments of the present teachings, the sample need not be migrated or extracted from a immiscible-fluid-discrete-volume of material, but can rather be migrated or extracted from samples in other forms in a conduit, for example, from a continuous stream of flowing sample that is not separated into immiscible-fluid-discrete-volumes. In some embodiments, an applied electric field influences charged analytes to migrate in a direction transverse to the conduit, for example, through a hole formed in a sidewall of a conduit.

According to various embodiments, a flow in a capillary, tube, or other conduit can be laminar with a velocity profile along the axial direction of the conduit, with little or no velocity component in the radial direction. Thus, a hole or puncture in the wall of the tube or conduit might not result in flow or leakage through the hole, if the pressure inside the tube or conduit is not large enough to overcome the surface tension of a liquid trying to move through the hole. Pressures can be matched so that oil or spacing fluid does not leak through the holes. In some embodiments, an electrode can pass through or be inserted into a hole in the sidewall of a conduit and be flush with, recessed from, or protruding from, the inner surface of the conduit wall.

Sample transfer methods, apparatuses, and/or systems disclosed herein can provide sample collection from a conduit while preserving immiscible-fluid-discrete-volume integrity, with the exception of sample components collected or removed from the immiscible-fluid-discrete-volume. This is beneficial in cases where the immiscible-fluid-discrete-volumes will be used in subsequent applications that require immiscible-fluid-discrete-volume integrity to be maintained in the conduit. The immiscible-fluid-discrete-volume can remain intact after removal of a potential that in some cases causes the surface to be wetted.

According to various embodiments, the methods of the present teachings can be integrated with a DNA sequencing apparatus, for example, using a fluid communication to such an apparatus. When the method involves using such an apparatus, the conduit outlet can be fluidly communicated with a DNA separation channel, and the DNA can be electrokinetically injected or migrated into the DNA separation channel. Thereafter, DNA separation can be performed, for example, with or without a separation matrix material in the channel.

According to various embodiments, methods of sample collection or extraction from a immiscible-fluid-discrete-volume can include directed sample collection. For example, if a positive electrode is placed in a well, a negatively charged sample component can be attracted to or travel toward that electrode. According to various embodiments, a pair of small openings in a wall of a immiscible-fluid-discrete-volume-carrying conduit can allow an electrical current to be conducted through an aqueous immiscible-fluid-discrete-volume in the immiscible-fluid-discrete-volume-carrying conduit, and negatively charged molecules can migrate from the immiscible-fluid-discrete-volume toward a positively charged electrode. In some embodiments, the field can enable the fluid to wet an electrode surface as occurs in electrowetting, providing at least an initial electrical contact.

According to various embodiments, multiple wells can be provided, each well with an electrode that can be switched on and off independently of the electrodes in the other wells. According to such embodiments in one regard, DNA can be transferred from a conduit to a selected well by switching on the electrode at that particular well. In some embodiments the electrodes can all be switched on and off together to permit simultaneous injection into a set of analyzer injectors. Spacing fluid can be added between volumes or slugs so that they can be made to line-up with holes.

FIG. 19 is a schematic illustration of an electrokinetic sample collection system 1900 according to various embodiments. System 1900 can comprise a conduit 1902 in the form of a conduit that contains spacing fluid 1908 and aqueous immiscible-fluid-discrete-volumes 1910. Each aqueous immiscible-fluid-discrete-volume 1910 can comprise DNA molecules or other charged molecules that are capable of migration in an electric field. Conduit 1902 can comprise pairs of holes and electrodes at various locations there along. In some embodiments a single hole is provided and an electrode is inserted through the wall of the conduit and can be flush with, set-back from, or protruding from, the inside of the conduit and a single analyte collection chamber.

As shown in FIG. 19, the pairs of holes formed in conduit 1902 can be in fluid communication with a single or with multiple charged analyte collection chambers or compartments, for example, in fluid communication with a plurality of wells. The chambers and compartments house or are comprised of electrodes and are also referred to herein as electrode housing chambers. Different pairs of electrodes, holes, and/or wells can be located at different positions along the length of conduit 1902. According to various embodiments, each of the pairs of electrodes can be switched on and off independently, such that one can transfer DNA or other charged analytes to a selected well by switching on an electrode pair comprising at least one electrode at that particular well. In various embodiments, a single position along the conduit 1902 can be the only position comprising a pair of holes and electrodes for charged analyte collection.

DNA samples can be collected from the aqueous immiscible-fluid-discrete-volumes 1910 in conduit 1902 by, for example, electrokinetic migration, electroosmotic migration, and/or electrophoretic migration, of negatively-charged DNA molecules. As shown at the left side of FIG. 19, according to various embodiments, two openings or holes 1916 and 1918 can be created through opposite sides of the wall of conduit 1902. Electrodes 1904 and 1906 can be placed in respective charged analyte collection chambers 1912 and 1914 aligned with openings 1916 and 1918, respectively. One or more of the aqueous immiscible-fluid-discrete-volumes 1910 can be brought into conduit section 1920 and aligned with openings 1916 and 1918. In various embodiments, flow through conduit 1902 can be stopped to allow electrophoresis of the desired materials out of the desired aqueous immiscible-fluid-discrete-volumes 1910. In other various embodiments, flow through conduit 1902 can be maintained at, or reduced to, a sufficiently slow velocity or flow rate to permit movement of a desired analyte from conduit 1902 into charged analyte collection chambers 1912 and/or 1914 when voltage is applied to the respective electrodes. Application of an electric field formed from electrodes 1904 and 1906 can cause charged molecules 1926 to migrate from the aqueous immiscible-fluid-discrete-volume 1910 toward the electrode with opposite potential 1904 or 1906. In some embodiments, and as shown, electrodes 1904 and/or 1906 can be disposed outside of conduit 1902. In various embodiments, only one of electrodes 1904 and 1906 can be placed outside conduit 1902, and the opposite electrode can be integrated into the inner sidewall of conduit 1902. In embodiments where electrode 1904 has a positive potential, negatively charged DNA molecules in one or more of aqueous immiscible-fluid-discrete-volumes 1910 can move toward electrode 1904 and migrate into charged analyte collection chamber 1912. When electrode 1906 is negatively charged, positively charged molecules can migrate to charged analyte collection chamber 1914. Such an arrangement can allow for DNA or other charged analyte sample collection while otherwise preserving the integrity of the aqueous immiscible-fluid-discrete-volumes 1910.

According to various embodiments, multiple electrokinetic migrations can be performed from the same immiscible-fluid-discrete-volume. Since the amount of charged analyte that migrates generally correlates with the applied electric field strength and time, the process can be controlled so that portions of sample in a immiscible-fluid-discrete-volume can be collected into different collection chambers or compartments, or different portions can be collected at different times during sample migration in the conduit or an adjoining chamber or channel, by controlling the application of the applied electric fields. In various embodiments, a sample from one chamber or compartment can be migrated into another chamber or compartment.

According to various embodiments, a high degree of serialism or parallelism in sample extraction from multiple immiscible-fluid-discrete-volumes can be achieved, as, for example, illustrated in FIG. 20. Given information pertaining to the spacing between aqueous immiscible-fluid-discrete-volumes in a conduit, the pairs of holes formed in the conduit can be fabricated at appropriate distances apart such that multiple immiscible-fluid-discrete-volumes can be subjected to electrokinetic migration simultaneously, offering a high level of multiplexed sample collection. FIG. 20 illustrates a system for such a multiplexing scheme using electrokinetic sample collection from aqueous immiscible-fluid-discrete-volumes 2010 in a conduit 2002. Spacing fluid 2008 is also illustrated and can be used to space-apart the aqueous immiscible-fluid-discrete-volumes. Migration of DNA molecules 2026 can be targeted to at least one of chambers 2012a, 2012b, 2012c, 2012d, 2012e, and 2012f by providing current to at least one of corresponding electrodes 2004a, 2004b, 2004c, 2004d, 2004e, and 2004f, respectively. A common electrode 2006 can be provided to complete a circuit from any one or more of corresponding electrodes 2004a, 2004b, 2004c, 2004d, 2004e, and 2004f DNA 2026 from sample chamber 2012 can migrate through opening 2016 in conduit 2002 into chamber 2012 and then be further migrated into at least one of chambers 2012a, 2012b, 2012c, 2012d, 2012e, or 2012f. In some embodiments, different potentials can be applied to the different electrodes 2004a-2004f, and/or the electrophoretic separation channels leading to chambers 2012a-2012f can be different from one another, for example, so that different analytes can be collected in the different chambers. In some embodiments, the separation channels leading to chambers 2012a-2012f can have different lengths from one another, can contain different separation media from one another, and/or can otherwise be different from one another. In some embodiments, the electrodes 2004a-2004f can be powered individually, in combination with electrode 2006, for example, such that analytes from six different aqueous immiscible-fluid-discrete-volumes can be collected respectively in the six different chambers or wells 2012a-2012f. In various embodiments, DNA 2026 can migrate toward electrode 2006 and into chamber 2014 from conduit 2002, if the current is reversed.

The electrokinetic sample collection from immiscible-fluid-discrete-volume 2010 in conduit 2002 can result in migration of DNA molecules into corresponding chambers serially, simultaneously, or in any other desired spatial or temporal order.

In the embodiments shown at least in FIGS. 19 and 20, a plurality of holes or openings can be used for simultaneous injection into a plurality of injectors, for example, 16 holes, openings, or locations, for electrokinetic migration can be spaced apart in a two by eight array spaced at a pitch equal to the pitch of a 16-capillary injector of a 16-capillary capillary electrophoresis apparatus. As such, the injector can interface with the migration holes, openings, or locations.

According to various embodiments and as illustrated in FIG. 21, conduit 2102 can contain spacing fluid 2110 and aqueous immiscible-fluid-discrete-volumes 2108. According to various embodiments, charged molecules 2126 can be transferred, for example, by causing negatively charged DNA molecules to migrate through openings 2112 and 2114 from lower conduit 2102 into upper conduit 2104. If two conduits are lined-up next to one another, it is possible to transfer charged molecules from one conduit to the other by exploitation of sample stacking characteristics, for example, as shown in FIG. 21. By providing the solution in one of the conduits with a high ion concentration, for example, as shown in top conduit 2104, charged molecules in the lower conduit can accumulate or stack-up at the interface of the two conduits and be migrated into the top conduit.

According to various embodiments and as illustrated in FIGS. 22A and 22B, a system and method similar to that shown in FIGS. 17 and 16, respectively, is provided. A sample in a conduit can comprise components useful for Sanger sequencing with dye terminators, for instance, using neutrally charged dye-ddNTPs. Using methods and apparatus described herein, including a system 2200 as shown, minimal or no sequencing clean-up is necessary during the sequencing protocol. In various embodiments as illustrated in FIG. 22A, upon application of a current selectively delivered to one or more capillaries via switches 2230, 2232, and the like, which in-turn are connected to an electrical power source, charged molecules 2226 can be made to migrate from the conduit 2202 into a injector 2212 at a junction 2216. Junction 2216 is defined by the intersection of wall 2213 of injector 2212 and top wall 2208 of conduit 2202. The bottom wall 2206 of conduit 2202 can serve as a negative electrode as shown in FIG. 22A. The charged molecules 2226 can comprise DNA fragments comprising one or more dyes in an aqueous immiscible-fluid-discrete-volume 2210. Aqueous immiscible-fluid-discrete-volumes 2210 can be spaced apart from one another by spacing fluid 2208, as shown. Any remaining neutrally charged dye molecules can remain in the conduit 2202 and not migrate into the injectors 2212. In other embodiments, a charged dye molecule can be used and both the dye and DNA fragments comprising the dye can migrate into one or more injectors 2212 or other chambers or compartments for further separation, purification, detection, or other processing, as desired.

According to various embodiments, controllable valves can be used for permitting, interrupting, or otherwise controlling, fluid flow through one or more of the capillaries, tubes, orifices, through holes, and the like conduits described herein. Exemplary controllable valves can include, but are not limited to, valves comprising a stator (or body) and rotor (or plug) structure, for example, any of the structures shown in FIGS. 23-28. Out-putting schemes to collect desired discrete-volumes and remove undesired discrete-volumes can use one or more rotary valves as shown in FIGS. 23-28, according to various embodiments.

Figure 23:
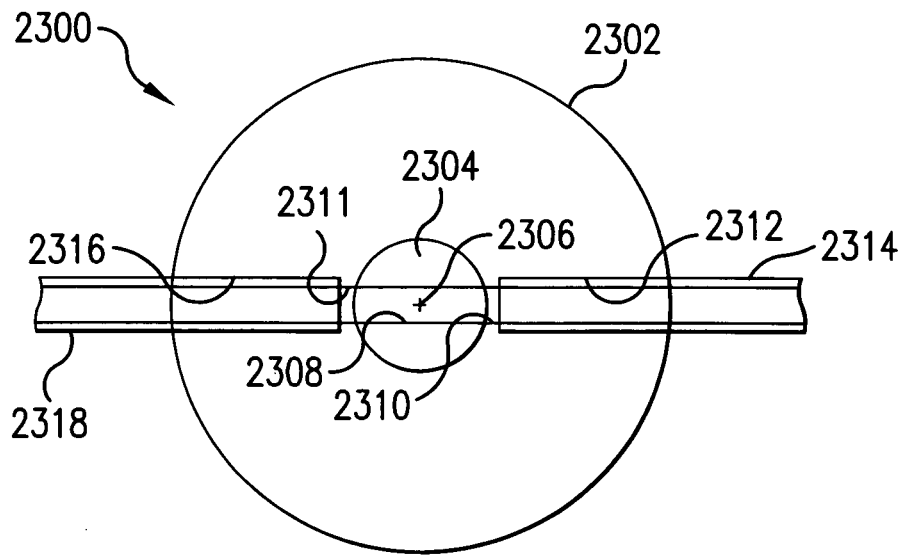
Figure 25:
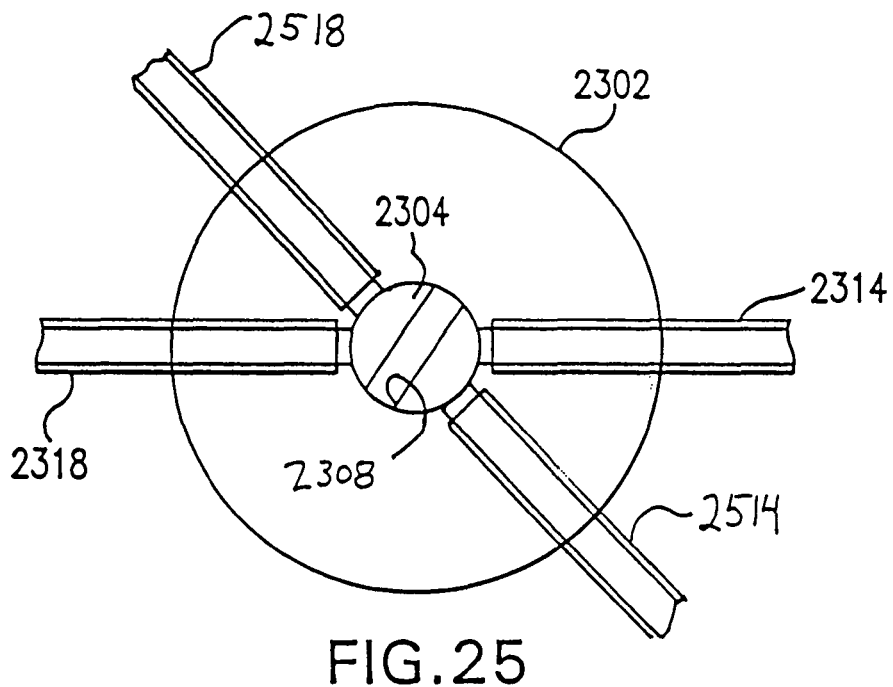

As shown in FIG. 23, valve 2300 can comprise a stator 2302, and a rotor 2304. Rotor 2304 can rotate, for example, about a central axis of rotation 2306, to orient the rotor such that valve 2300 is in an open state (as shown in FIG. 23), in a closed state (as shown in FIG. 25), or in an intermediate state. In the open state shown in FIG. 23, a central bore or through hole 2308 through rotor 2304 is aligned with bores or through holes 2310 and 2311 formed in stator 2302. Through hole 2310 in stator 2302 can be aligned with a larger recess 2312 in stator 2302, in which recess 2312 and first conduit 2314, for example, a tube, can snugly fit and/or be adhered or otherwise connected. Likewise, through hole 2311 can be aligned with and in fluid communication with a larger recess 2316 also in stator 2302. Recess 2316 can accommodate a second conduit 2318 fit, adhered, or otherwise connected to stator 2302. In some embodiments, each of through holes 2308, 2310, and 2311, and each of recesses 2312 and 2316, has a circular cross-section although other cross-sections can be used.

As shown in FIG. 25, rotation of rotor 2304 can interrupt fluid communication between conduits 2314 and 2318 and rotation of rotor 2304 can form a fluid communication through two different conduits 2514 and 2518. A programmable drive unit can be provided to actuate rotation of rotor 2308. By filling through hole 2308 with a first fluid, for example, flowing through conduits 2314 and 2318, and then rotating rotor 2304, with a portion of the first fluid captured in through-hole 2308, to form a communication with conduits 2514 and 2518, the portion of first fluid captured in through-hole 2308 can be disposed into a flow of a second fluid through conduits 2514 and 2518, for example, wherein the second fluid is immiscible with the first fluid. Repeated operations of such action can result in the formation of a plurality of immiscible-fluid-discrete-volumes spaced apart from another by an immiscible spacing fluid, similar to the methods of formation described in connection with the slider system shown in FIGS. 21A-21F herein. Similarly, a slug can be chopped or divided into two or more portions, using such a method, and the two or more portions can then be output for separate further processing.

Figure 24:
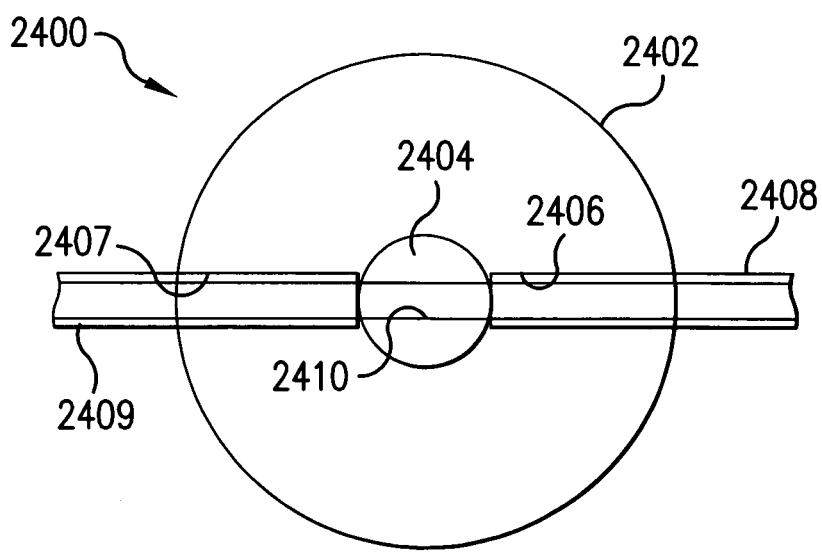

In valve 2400 shown in FIG. 24, the combination of a smaller diameter through hole and a larger diameter recess in each side (left and right as shown) of a stator 2402 has been replaced with single through holes 2406 and 2407 on opposing sides of a rotor 2404. In the embodiments shown in FIG. 24, conduits 2408 and 2409 are accommodated, respectively, and fit snugly within, through holes 2406 and 2407, for example, adhered, such that the ends of conduits 2408 and 2409 closest to rotor 2404 abut rotor 2404. Valve 2400 is shown in an open position with through hole 2410 of rotor 2404 being aligned with and sharing the same cross-sectional dimensions and shape as the interiors of conduits 2408 and 2409.

Figure 26:
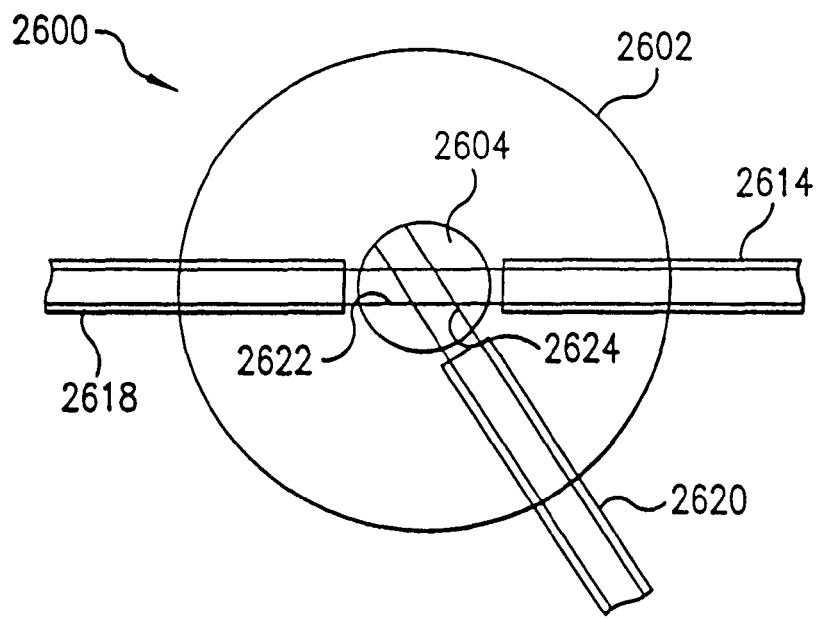

In the valve embodiment shown in FIG. 26, a valve 2600 comprises three through passages in stator 2602, which accommodate conduits 2614, 2618, and 2620. Rotor 2604 is provided with two intersecting through holes 2622 and 2624. Depending upon the orientation of rotor 2604, for example, determined by rotation about a central axis of rotation, valve 2600 can assume a closed position, a straight-line open position, or the Y-intersection position shown. When utilized in a Y-intersection position such as shown in FIG. 26, one or more fluids entering the intersection in the middle of rotor 2604 from conduit 2614 can merge with one or more miscible and/or immiscible fluids entering the intersection from conduit 2620, such that a resulting combined flow of fluid can be made to move inside conduit 2618 in a direction away from the intersection.

In some embodiments, a first fluid to be divided into immiscible-fluid-discrete-volumes, for example, an aqueous slug fluid, can enter the intersection from either of conduits 2614 or 2620, and an immiscible spacing fluid can enter the intersection through the other of conduits 2614 and 2620, to generate immiscible-fluid-discrete-volumes of the first fluid spaced by the spacing fluid. In some embodiments, reagents or additional components can be merged into existing fluids or aqueous immiscible-fluid-discrete-volumes entering the intersection, for example, such that the size and/or number of reagents in an immiscible-fluid-discrete-volume can be increased at the intersection. By turning rotor 2604 about 45° counterclockwise, a fluid communication can be provided between only conduit 2614 and 2618, and fluid communication with conduit 2620 can be interrupted.

Figure 27:
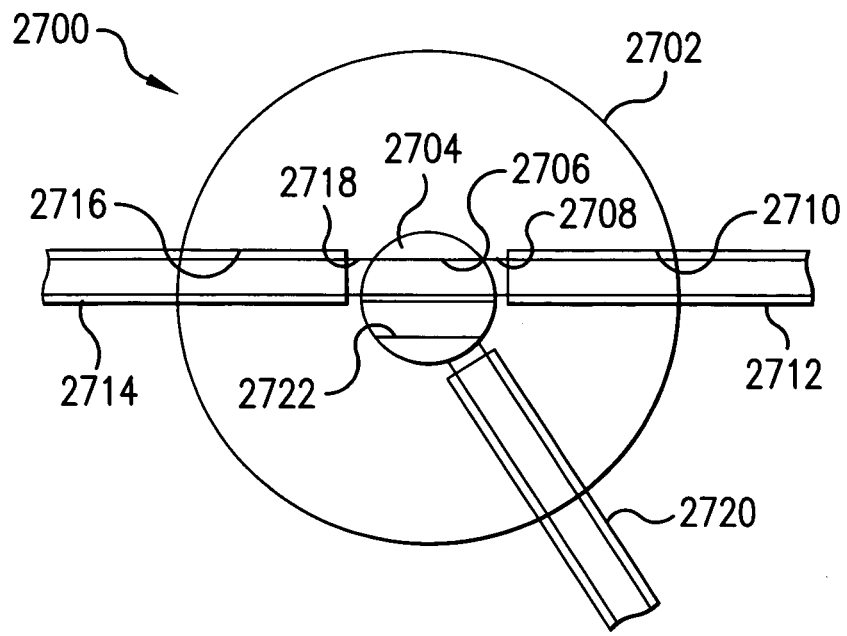
Figure 28:
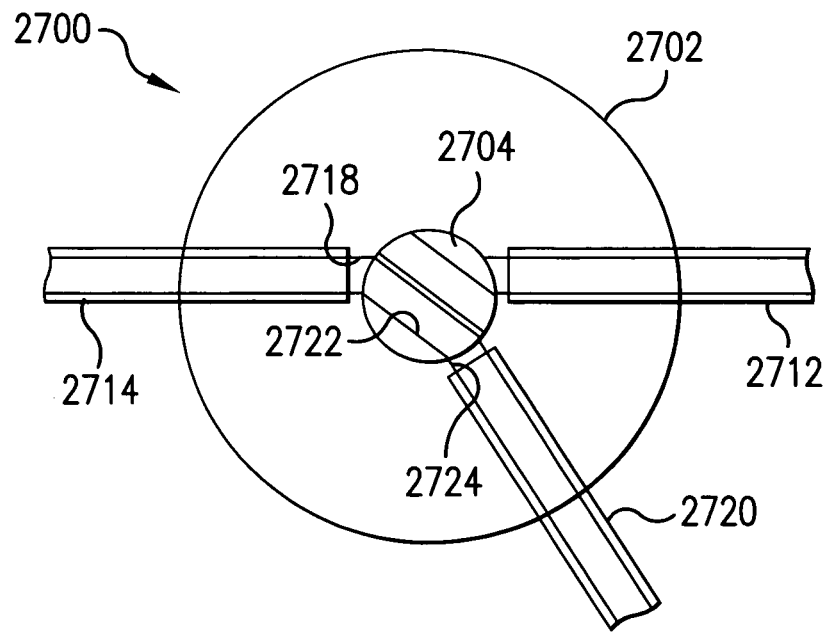

Another controllable valve that can be implemented in many of the systems and methods described herein, is the valve shown in FIGS. 27 and 28. Valve 2700 comprises a stator 2702 and a rotor 2704 that comprises two through holes 2706 and 2722. In a first orientation of rotor 2704, as shown in FIG. 27, through hole 2706 is aligned with through holes 2708 and 2718 of stator 2702 and provides a fluid communication between conduit 2712 and conduit 2714. In FIG. 27, through hole 2722 in rotor 2704 is in a closed, non-operative, position.

As shown in FIG. 28, by rotating rotor 2704, through hole 2722 can be aligned with through hole 2718 and through hole 2724 in stator 2702 such that conduit 2714 is in fluid communication with conduit 2720 and fluid communication to conduit 2712 is interrupted.

As can be seen from FIGS. 23-28, a method is provided that comprises merging together at an intersection of a first conduit and a second conduit a first fluid and a second fluid, the first fluid comprising a spacing fluid and the second fluid comprising an immiscible-discrete-volume-forming fluid that is immiscible with the first fluid, such that a set of immiscible-fluid-discrete-volumes of the second fluid are formed in a third conduit in fluid communication with the first conduit and the second conduit, wherein each immiscible-fluid-discrete-volume of the set is spaced apart from other immiscible-fluid-discrete-volumes by the first fluid, and at least one of the first fluid, the second fluid, and the set of immiscible-fluid-discrete-volumes flows through a rotary valve comprising a stator and a rotor. In some embodiments, at least a portion of each of the first conduit, the second conduit, and the third conduit is disposed in the rotor, and the intersection comprises an intersection of the three portions in the rotor. In some embodiments, the rotor can comprise at least two independent, non-intersecting through holes formed therein, wherein one of the at least two through holes is in fluid communication with the first conduit, and another of the at least two through holes is in fluid communication with the second conduit.

As shown in FIG. 29, according to various embodiments a valve can be provided that has a slider 2908 in a housing 2910 that moves to either form a three-way intersection between three conduits 2902, 2904, and 2906, or to interrupt fluid communication between conduits 2902 and 2904, and thus, to interrupt fluid communication between either conduit 2902 or conduit 2904, and conduit 2906.

Through the use of various combinations of the valves shown in FIGS. 23-29, any of a variety of fluid processing pathways can be effectuated in a multi-pathway system such as the multi-pathway systems described herein. Selected pathways for collection versus waste removal can be provided by appropriate control of rotary or other valves in such pathways.

According to various embodiments, the present teaching can comprise the placement of processed immiscible-fluid-discrete-volumes in a sample tray, for example, a multi-well plate. The immiscible-fluid-discrete-volumes placed on the sample tray can be subjected to further analysis, for example, capillary electrophoresis. It can be desirable to select only certain immiscible-fluid-discrete-volumes, from a set of immiscible-fluid-discrete-volumes, for analysis. The present teachings can comprise a selection process whereby only immiscible-fluid-discrete-volumes containing analytes of interest are selected for placement on the sample plate. For example, only immiscible-fluid-discrete-volumes that have successfully undergone a nucleic acid amplification reaction can be selected for placement on the sample tray. A nucleic acid amplification reaction can fail for a number of reasons, for example, the lack of a suitable template, improper temperature control, or improper/missing reactants.

According to some embodiments, and as illustrated in FIG. 30, the present teachings can comprise a system 3000 for separating selected immiscible-fluid-discrete-volumes from a set of immiscible-fluid-discrete-volumes. System 3000 can comprise a dispensing conduit 3002, for dispensing immiscible-fluid-discrete-volumes 3001. Dispensing conduit 3002 can have a consistent diameter. In some embodiments, dispensing conduit 3002 can have a diameter that is gradually reduced towards a discharge tip 3004, and conduit 3002 can further comprise a lip around discharge tip 3004 (not shown). System 3000 can comprise a positioning unit 3006 for positioning dispensing conduit 3002. For example, dispensing conduit can be moved in X, Y, and/or Z directions.

According to various embodiments, system 3000 can comprise a detector 3008. Detector 3008 can comprise an infrared slotted optical switch, a photodiode, a fluorescence detector, a PMT, a photodiode, or any other suitable detector. Detector 3008 can comprise a lens 3010, a beam splitter 3012, a light source 3014, and/or a photo-detector 3016. Detector 3008 can be a refractive detector capable of detecting the presence, size, and/or speed of an immiscible-fluid-discrete-volume present in dispensing conduit 3002. Detector 3008 can detect the differences between volumes of, for example, air, water, and/or oil. In some embodiments, system 3000 can comprise multiple detectors (not shown). The multiple detectors can be a known distance apart along dispensing conduit 3002. The detectors can be used to determine the speed of an immiscible-fluid-discrete-volume by measuring the time it takes for the immiscible-fluid-discrete-volume to pass from one detector to the next. A signal from one or more detectors can be sent to positioning unit 3026 to appropriately position discharge tip 3004 for either discrete-volume collection or waste removal.

According to some embodiments, system 3000 can comprise a waste removal block 3018. Waste removal block 3018 can comprise a through-hole 3020. Waste removal block 3018 can comprise a waste removal conduit 3022. Waste removal conduit 3022 can be in fluid communication with through-hole 3020. Waste removal conduit 3022 can further comprise an aperture 3021. Aperture 3021 can be in fluid communication with through-hole 3020. Aperture 3021 can be used to visually inspect discharge tip 3004 through through-hole 3020. System 3000 can comprise a vacuum source 3030. Vacuum source 3030 can be in fluid communication with waste removal conduit 3022. System 3000 can comprise a sample tray 3024. Sample tray can comprise a positioning unit 3026. Positioning unit 3026 can move sample tray 3024, for example, in X, Y, and/or Z directions, or can move waste removal block 3018, or both. Sample tray 3024 can be disposed below waste removal block 3018. In some embodiments, the sample tray can be in the form of a tray as illustrated in FIG. 2, 12, or 18, herein.

System 3000 can comprise a control unit 3028. Control unit 3028 can be connected, for example, electrically connected, to positioning unit 3006, detector 3008, positioning unit 3026, and/or vacuum source 3030. Control unit 3028 can comprise a microprocessor or the like. Control unit 3028 can function to control the elements connected thereto.

According to various embodiments, system 3000 can be used in conjunction with a method of selecting and depositing specific immiscible-fluid-discrete-volumes. For the following selection method, all elements can be controlled by control unit 3028. In some embodiments the method comprises lowering dispending conduit 3002 into through-hole 3020, of waste removal block 3018. A vacuum can be applied to waste removal conduit 3022. Immiscible-fluid-discrete-volumes can be moved toward discharge tip 3004. Non-selected immiscible-fluid-discrete-volumes, and any associated oil spacing fluid, can be sucked out of discharge tip 3004, into waste removal conduit 3022, and discarded. The vacuum can be applied (with appropriate delays as required) until an immiscible-fluid-discrete-volume of interest is detected by detector 3008.

According to some embodiments, the selection method comprises detecting an immiscible-fluid-discrete-volume of interest, then waiting an amount of time before removing the vacuum from waste removal conduit 3022. The amount of time can be sufficient for the immiscible-fluid-discrete-volume of interest to move into discharge tip 3004. As depicted in FIG. 31, dispensing conduit 3002 can be moved such that discharge tip is disposed in or directly above sample tray 3024. An immiscible-fluid-discrete-volume of interest can then be expelled from dispensing conduit 3002, into a well of sample tray 3024.

According to various embodiments, sample tray 3024 can be positioned such that an empty well is directly below dispensing tip 3004. Sample tray 3024 can be moved, for example, shortly before an immiscible-fluid-discrete-volume is expelled, shortly thereafter, or at any time in between such that an empty well is disposed in the proper position before an immiscible-fluid-discrete-volumes is expelled therein.

After an immiscible-fluid-discrete-volume has been expelled, the dispensing conduit 3002 can be moved back into its original position shown in FIG. 30, and the process can begin again.

In some embodiments, a liquid flow can be induced in waste removal conduit 3022 rather than an air vacuum. The liquid flow can function to rinse and/or wash discharge tip 3004, and thereby prevent cross contamination.

What is claimed is:
1. A method comprising:
diluting a sample into sample portions wherein at least one sample portion contains a single fragment of target analyte;
forming in a conduit a plurality of aqueous sample slugs spaced apart from one another by slugs of spacing fluid, and at least one of the aqueous sample slugs comprising at least one target analyte, wherein the forming includes:
flowing the sample portions and the spacing fluid from an aqueous sample injection unit and a spacing fluid injection unit, respectively, and
injecting volumes of the sample portions and the spacing fluid respectively to form the aqueous sample slugs in the conduit;
amplifying a target analyte located in at least one aqueous sample slug;
dispensing the aqueous sample slugs one-at-a-time from the conduit onto a substrate to form a pattern of spaced apart aqueous samples on the substrate, the substrate comprising an electrically conductive surface and an immersion fluid configured to have the dispensed aqueous sample slugs immersed therein, and the dispensing onto the substrate comprising dispensing the aqueous sample slugs directly onto the electrically conductive surface of said substrate;
reacting the at least one target analyte with a reagent mixture to form at least one target analyte product;
imaging the electrically conductive surface to differentiate a target analyte product from non-target analyte products;
positioning a collection device comprising a capillary of a capillary electrophoretic analyzer, adjacent the at least one target analyte product on the substrate;
injecting at least a portion of the at least one target analyte product into the collection device, wherein the injecting comprises applying a potential to the electrically conductive surface and the capillary; and
performing nucleic acid sequencing on the at least one target analyte product with the capillary electrophoretic analyzer.
2. The method of claim 1, wherein the electrically conductive surface comprises at least one linker moiety bound thereto, wherein the at least one linker moiety is adapted to bind the at least one target analyte.

3. The method of claim 2, further comprising:
capturing the at least one target analyte with the at least one linker moiety to form at least one bound target analyte; and
solubilizing the bound target analyte or a reaction product thereof prior to injection.

4. The method of claim 2, further comprising contacting the electrically conductive surface with a mixture of sequencing reaction components.

5. The method of claim 1, wherein the electrically conductive surface comprises a gold-coated surface.

6. The method of claim 2, wherein the at least one target analyte comprises at least one target nucleic acid sequence.

7. The method of claim 1, further comprising:
binding the at least one target analyte to the substrate to form at least one bound target analyte;
reacting the at least one bound target analyte with a reagent mixture to form at least one target analyte product; and
solubilizing the target analyte product prior to injection.

8. The method of claim 3, further comprising reacting the at least one bound target analyte with a reagent mixture to form at least one target analyte product.

9. The method of claim 1, wherein forming the pattern of spaced apart aqueous samples comprises forming a plurality of rows of aqueous samples.

10. A method comprising:
diluting a sample into sample portions wherein at least one sample portion contains a single fragment of target analyte;
forming in a conduit a plurality of spaced apart aqueous sample slugs comprising at least one target analyte comprising at least one respective linkage group, wherein the forming includes:
flowing the sample portions and the spacing fluid from an aqueous sample injection unit and a spacing fluid injection unit, respectively, and
injecting volumes of the sample portions and the spacing fluid respectively to form the aqueous sample slugs in the conduit;
amplifying a target analyte located in at least one aqueous sample slug;
dispensing the aqueous sample slugs one-at-a-time from the conduit onto a substrate to form a pattern of aqueous samples on the substrate, the substrate comprising an electrically conductive surface adapted to bind the at least one respective linkage group to form an attached analyte and an immersion fluid configured to have the dispensed aqueous sample slugs immersed therein, and the dispensing onto the substrate comprising dispensing the aqueous sample slugs directly onto the electrically conductive surface of said substrate;
reacting the at least one target analyte with a reagent mixture to form at least one target analyte product;
imaging the electrically conductive surface to differentiate a target analyte product from non-target analyte products;
positioning a collection device comprising a capillary of a capillary electrophoretic analyzer, adjacent the at least one target analyte product;
injecting at least a portion of the at least one target analyte product into the collection device wherein the injecting comprises applying a potential to the electrically conductive surface and the capillary; and
performing nucleic acid sequencing on the at least one target analyte product with the capillary electrophoretic analyzer.

11. The method of claim 10, further comprising:
bonding the at least one linkage group to the electrically conductive surface to form at least one captured target analyte; and
solubilizing the bound target analyte or a reaction product thereof prior to injection.

12. The method of claim 11, further comprising contacting the electrically conductive surface with a mixture of sequencing reaction components after the bonding.

13. The method of claim 10, wherein the electrically conductive surface comprises a metal coated surface.

14. The method of claim 10, wherein the electrically conductive surface comprises a goldcoated surface.

15. The method of claim 10, wherein the at least one target analyte comprises at least one target nucleic acid sequence.

16. The method of claim 10, wherein forming the pattern of aqueous samples comprises forming a plurality of rows of aqueous samples.

17. A method comprising:
diluting a sample into sample portions wherein at least one sample portion contains a single fragment of target analyte;
flowing the sample portions and the spacing fluid from an aqueous sample injection unit and a spacing fluid injection unit, respectively, and
injecting volumes of the sample portions and the spacing fluid respectively to form aqueous sample slugs in the conduit;
amplifying target analyte in a plurality of aqueous sample slugs in a conduit to form amplicons, each aqueous slug separated from an adjacent aqueous slug by at least one oil slug;
depositing the amplicons from the conduit onto the substrate, the substrate comprising an electrically conductive surface and an immersion fluid configured to have the deposited amplicons immersed therein, and the depositing comprising depositing the amplicons directly onto the electrically conductive substrate;
attaching the amplicons to the electrically conductive surface;
contacting the substrate with a sequencing reaction mixture to form at least one dye-labeled spot;
imaging the electrically conductive surface to differentiate a target analyte product from non-target analyte products;
positioning a capillary of a capillary electrophoretic analyzer over the at least one dye-labeled spot; electrically contacting the dye-labeled spot with the capillary;
injecting one or more components from the dye-labeled spot into the capillary wherein the injecting comprises applying a potential to the electrically conductive surface and the capillary; and
performing nucleic acid sequencing on the at least one target analyte product with the capillary electrophoretic analyzer.

18. The method of claim 17, wherein the amplifying comprises incorporating a 5'-sulfhydryl group into a DNA molecule.

19. The method of claim 17, wherein the surface comprises an electrically conductive surface.

20. The method of claim 19, wherein the electrically conductive surface comprises a gold surface.

21. The method of claim 17, wherein the surface comprises a binding moiety.

22. The method of claim 17, further comprising washing the electrically conductive surface with a denaturing solution after depositing the amplicons from the conduit onto the electrically conductive surface.

23. The method of claim 17, wherein the sequencing reaction mixture comprises a primer and a dye-labeled terminator and the method comprises reacting the amplicons with the primer and the dye-labeled terminator to form the dye-labeled spot.

24. The method of claim 17, further comprising imaging the electrically conductive surface and determining a location of the dye-labeled spot.

25. The method of claim 17, further comprising analyzing the one or more components in the capillary electrophoretic analyzer.

26. The method of claim 17, wherein the electrically conductive surface comprises reactive groups.

27. The method of claim 26, wherein the reactive groups comprise one or more of carboxy groups, amino groups, and hydroxyl groups.

28. A method comprising:
diluting a sample into sample portions wherein at least one sample portion contains a single fragment of target analyte;
flowing the sample portions and the spacing fluid from an aqueous sample injection unit and a spacing fluid injection unit, respectively, and
injecting volumes of the sample portions and the spacing fluid respectively to form aqueous sample slugs in a conduit, each aqueous slug separated from an adjacent aqueous slug by at least one non-aqueous slug;
moving the conduit comprising the target analyte over a substrate and depositing the target analyte from the conduit onto the substrate, the substrate comprising an electrically conductive surface and an immersion fluid configured to have the dispensed aqueous sample slugs immersed therein, and the depositing comprising depositing the aqueous sample slugs directly onto the electrically conductive substrate;
attaching the target analyte to the electrically conductive surface;
contacting the electrically conductive surface with a reaction mixture;
imaging the electrically conductive surface to differentiate a target analyte product from non-target analyte products;
positioning a second conduit of a capillary electrophoretic analyzer over the target analyte product;
electrically contacting the target analyte product with the second conduit;
injecting the target analyte product into the second conduit wherein the injecting comprises applying a potential to the electrically conductive surface and the second conduit; and
performing nucleic acid sequencing on the at least one target analyte product with the capillary electrophoretic analyzer.

29. The method of claim 1, wherein the electrically conductive surface is in electrical communication with a voltage source for application of an electrical potential to the electrically conductive surface.

30. The method of claim 1, wherein the conduit comprises tubing.

31. The method of claim 10, wherein the conduit comprises tubing.

32. The method of claim 17, wherein the electrically conductive surface is in electrical communication with a voltage source for application of an electrical potential to the electrically conductive surface.

33. The method of claim 28, wherein the electrically conductive surface is in electrical communication with a voltage source for application of an electrical potential to the electrically conductive surface.

34. The method of claim 1, further comprising flowing the plurality of spaced apart aqueous sample plugs containing the at least one nucleic acid and the at least one target analyte through the conduit to the substrate where said dispensing occurs, through or by one or more intervening sample processors selected from the group consisting of an amplification thermo-cycler, an excitation source, a spectrophotometric detector, and a discriminating/waste collector device.

35. The method of claim 10, further comprising flowing the plurality of spaced apart aqueous sample plugs containing the at least one nucleic acid and the at least one target analyte through the conduit to the substrate where said dispensing occurs, through or by one or more intervening sample processors selected from the group consisting of an amplification thermocycler, an excitation source, a spectrophotometric detector, and a discriminating/waste collector device.

36. The method of claim 1, wherein the substrate includes a plurality of hydrophilic regions corresponding to the pattern, and each aqueous sample slug is dispensed onto a hydrophilic region of the plurality of hydrophilic regions.

37. The method of claim 36, wherein each hydrophilic region includes an electrically conductive surface.

* * * * *